United States Patent [19]

Imaki et al.

[11] Patent Number: 4,935,446

[45] Date of Patent: Jun. 19, 1990

[54] PROSTAGLANDIN ANALOGUES, PROCESS FOR THEIR PREPARATION AND PHARMACEUTICAL COMPOSITIONS CONTAINING THEM

[75] Inventors: Katsuhiro Imaki, Tsuzuki; Hajimu Miyake, Takatsuki; Tadao Okegawa, Yawata, all of Japan

[73] Assignee: Ono Pharmaceutical Co., Ltd., Osaka, Japan

[21] Appl. No.: 331,011

[22] Filed: Mar. 30, 1989

Related U.S. Application Data

[63] Continuation of Ser. No. 757,305, Jul. 22, 1985, abandoned.

[30] Foreign Application Priority Data

Jul. 23, 1984 [JP] Japan .................................. 59-151369

[51] Int. Cl.$^5$ .................. C07C 177/00; A61K 31/557
[52] U.S. Cl. .................................... 514/530; 514/573; 560/118; 562/500; 536/46
[58] Field of Search ....................... 560/118; 562/500; 514/530, 573; 536/46

[56] References Cited

U.S. PATENT DOCUMENTS

| | | | |
|---|---|---|---|
| 4,180,675 | 12/1979 | Hayashi | 560/118 |
| 4,220,795 | 9/1980 | Kluendes | 560/118 |
| 4,275,075 | 6/1981 | Kurono | 560/118 |
| 4,278,688 | 7/1981 | Hayashi | 560/118 |
| 4,562,207 | 12/1985 | Imaaki | 560/118 |

FOREIGN PATENT DOCUMENTS

| | | | |
|---|---|---|---|
| 0013955 | 8/1980 | European Pat. Off. | 560/118 |
| 0034778 | 9/1981 | European Pat. Off. | 560/118 |
| 0122019 | 10/1984 | European Pat. Off. | 560/118 |
| 2381043 | 2/1978 | France | 560/118 |
| 2017699 | 10/1979 | United Kingdom | 560/118 |

*Primary Examiner*—Robert Gerstl
*Attorney, Agent, or Firm*—Stevens, Davis, Miller & Mosher

[57] ABSTRACT

The present invention relates to novel isomers of PGAs, PGDs, PGEs, PGFs, 6-keto-PGE$_1$s, 6-keto-PGF$_1$s, PGI$_2$s, 6,9α-nitrilo-PGI$_1$s and 6,9α-methano-PGI$_2$s, having a specific steric configuration, which are replaced by an alkyl (C$_1$ to C$_8$)-substituted cycloalkyl (C$_4$ to C$_7$) group in 1S,S) form, in 1S,R) form or in cis form at the 15-, 16- or 17-position of the PG skeleton, and, alkyl esters thereof, non-toxic salts thereof, non-toxic acid addition salts thereof and cyclodextrin clathrates thereof, possessing more potent PG-like pharmacological activity than other isomers.

15 Claims, No Drawings

PROSTAGLANDIN ANALOGUES, PROCESS FOR THEIR PREPARATION AND PHARMACEUTICAL COMPOSITIONS CONTAINING THEM

This application is a continuation of application Ser. No. 757,305, filed July 22, 1985, now abandoned.

The present invention relates to novel isomers of prostaglandin (abbreviated to PG hereafter) analogues having a specific steric configuration. More particularly, the present invention relates to novel isomers of PG analogues which comprise an alkyl-substituted cycloalkyl group in the grouping attached to the 15-position.

PGs are derivatives of prostanoic acid having the following structure:

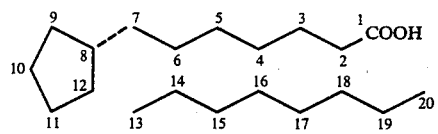

Various types of PGs are known, and their types depend on the structure of the alicyclic ring and the substituents. For example, the alicyclic rings of PGA, PGD, PGE, PGF, $PGI_2$, $6,9\alpha$-nitrilo-PGI and $6,9\alpha$-methano-$PGI_2$ have the following structures, respectively:

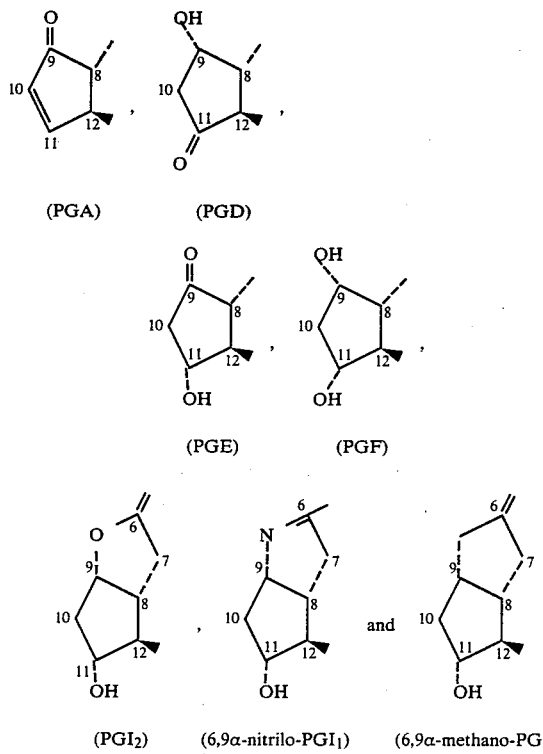

In the above structural formulae or in the other structural fomulae in this specification, according to the generally accepted nomenclature, the broken line indicates that the substituent attached thereto is behind the ring plane, i.e. is of the α-configuration, the bold line indicates that the substituent attached thereto is in front of the ring plane, i.e. is of the β-configuration, and the wavy line indicates that the substituent attached thereto is of the α-configuration or the β-configuration.

These compounds are sub-classified according to the positions of the double bonds in the side chains attached to the alicyclic ring at the 8-position and the 12-position. The PG-1 compound has a trans double bond (trans-$\Delta^{13}$) between $C_{13}$-$C_{14}$ and the PG-2 compound has a cis double bond between $C_5$-$C_6$ and a trans double bond between $C_{13}$-$C_{14}$ (cis-$\Delta^5$, trans-$\Delta^{13}$).

Further, when one or more methylene groups are removed from the aliphatic group attached at the 12-position of the alicyclic ring of a prostaglandin, said compound is known as a nor-prostaglandin according to the general rule of the organic nomenclature, and the number of the removed methylene groups is indicated by adding di-, tri- etc. before the prefix "nor".

The PGs generally have pharmacological properties. For example, they exert various effects, including the stimulation of contraction of smooth muscles, a hypotensive effect, a diuretic effect, a bronchial dilation effect, the inhibition of lypolysis, the inhibition of platelet aggregation and the inhibition of gastric acid secretion. Therefore, they are useful in treatments of hypertension, thrombosis, asthma and gastric and intestinal ulcers, in the induction of labor and abortion in pregnant mammals, in the prevention of arteriosclerosis and also as diuretics. They are liposoluble substances present in extremely small quantities in the tissues which secrete PGs in vivo in animals.

The following patents and published applications describe PG analogues which comprise an alkyl-substituted cycloalkyl group in the grouping attached to the 15-position of the PG skeleton:
1. U.S. Pat. No. 4,087,620, GBP-1545213 (PGA, PGE and PGF compounds),
2. U.S. Pat. No. 4,178,367, GBP-1598953 ($PGI_2$ compounds),
3. U.S. Pat. No. 4,215,142, GBP-2079268 (6-keto-PGE compounds),
4. U.S. Pat. No. 4,234,597, GBP-2016456 ($6,9\alpha$-nitrilo-$PGI_1$ compounds),
5. U.S. Pat. No. 4,479,966, GBP-2017699 ($6,9\alpha$-methano-$PGI_2$ compounds) and
6. EP-97023, (PGD compounds)

"USP" indicates "United States Patent No."
"GBP" indicates "British Patent No."
"EP" indicates "European Patent Publication No."

The cycloalkyl moiety of an alkyl-substituted cycloalkyl group leads to the existence of steric isomers. That is, four optical isomers may occur when two asymmetric carbon atoms (i.e. the carbon atom by which the cycloalkyl group is attached to the PG skeleton, and that bonded to the alkyl substituent) exist, or two geometrical isomers in cis form and trans form may occur when no asymmetric carbon atoms exist (see the following structures, with the proviso that these structures do not limit the present invention).

(i) When asymmetric carbon atoms exist:
(a) when the cycloalkyl group is of the formula:

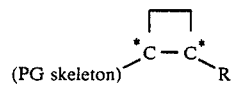

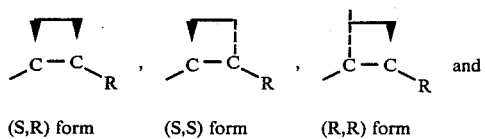

(S,R) form    (S,S) form    (R,R) form

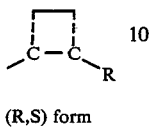

(R,S) form (b) when the cycloalkyl group is of the formula:

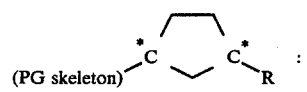

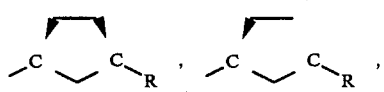

(S,R) form    (S,S) form (R,R) form    (R,S) form (c) when the cycloalkyl group is of the formula:

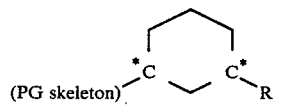

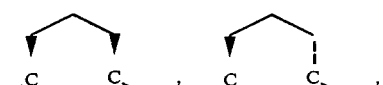

(S,R) form    (S,S) form (R,R) form    (R,S) form (ii) when no asymmetric carbon atoms exist:
(a) when the cycloalkyl group is of the formula:

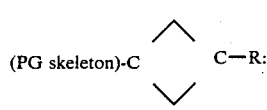

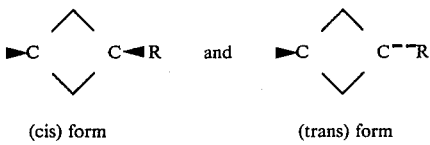

(cis) form    (trans) form (b) when the cycloalkyl group is of the formula:

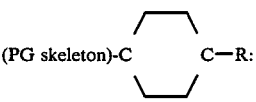

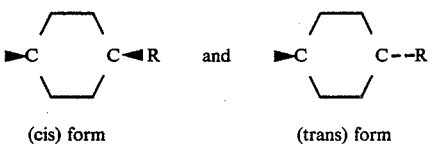

(cis) form    (trans) form wherein R represents an alkyl substituent and *C represents an asymmetric carbon atom.

However, in the specifications of the patents and published applications listed above there is no specific description of the existence of the isomers just described and there is no preparative example which shows that the separation of such isomers has been carried out in practice. Furthermore, the difference in pharmacological activity between each isomer has never been investigated before.

As a result of research and experimentation the isomeric forms depicted above have been synthesised for the first time. Investigation of the pharmacological activity of each of the isomers thus obtained has revealed that there is a great difference in pharmacological activity between the isomeric forms.

Detailed investigations have shown that:

(i) when two asymmetric carbon atoms exist, the isomers having the carbon atom bonded to the PG skeleton in S-configuration (i.e. isomers in (S,R) form and in (S,S) form) generally show stronger PG-like pharmacological activities than those having the carbon atom bonded to the PG skeleton in R-configuration (i.e. isomers in (R,R) form and in (R,S) form), and (ii) when isomers in cis form and trans form exist, the isomer in cis form generally shows stronger PG-like pharmacological activites than that in trans form.

Generally speaking, it is entirely impossible to foresee whether or not a difference in steric configuration will affect the pharmacological activity of a chemical compound, and which isomer has the strongest activity, if the activity is affected. These questions cannot be answered until the pharmacological effect is confirmed following synthesis of the individual isomers. Similar considerations apply to PG analogues which comprise an alkyl-substituted cycloalkyl group in the grouping attached to the 15-position. The fact that the isomers in (S,R) form, in (S,S) form and in cis form, have stronger pharmacological activity than the other isomers, has been discovered following synthesis of the isomers and testing thereof.

Prior to preparation of the isomers it was entirely impossible to foresee that the above fact can be generally applied to PG analogues having any fundamental PG skeleton (defined as the moiety (A) hereafter).

Furthermore, it is not preferable to formulate pharmaceutical compositions using a mixture of isomers. The component ratio of each isomer in a mixture sometimes changes greatly according to slight differences in reaction conditions (e.g., reaction temperature, reaction time, solvents, conditions for purification) when a mixture of isomers is prepared. However, taking account of the strict quality standards required when preparing materials relating to human health, such as the standards established for the preparation of pharmaceuticals, it is undesirable to change the component ratio of a mixture among each lot. Bearing this in mind the significance of the present invention which permits the preparation of individual isomers can be readily appreciated.

Accordingly, the present invention provides PG analogues of the general formula:

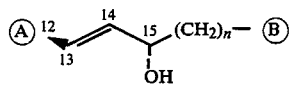
(I)

(wherein Ⓐ represents a group of the general formula:

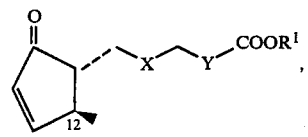
(IIa)

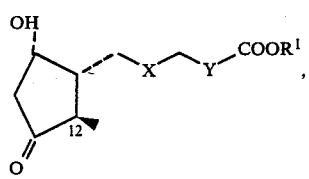
(IIb)

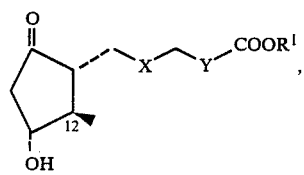
(IIc)

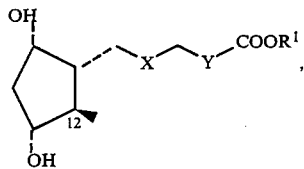
(IId)

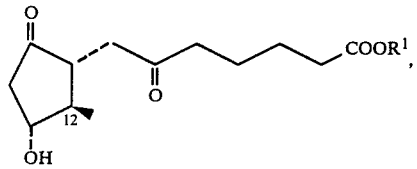
(IIe)

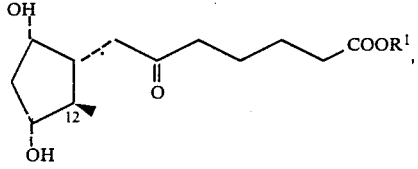
(IIf)

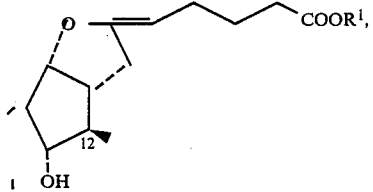
(IIg)

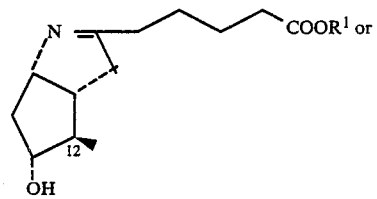
(IIh)

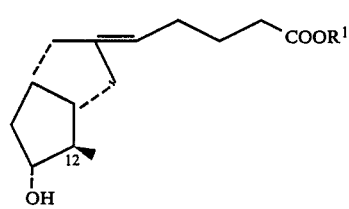
(IIi)

(wherein X represents a cis-vinylene group or an ethylene group, Y represents an ethylene group or a trans-vinylene group, $R^1$ represents a hydrogen atom or a straight- or branched-chain alkyl group of 1 to 4 carbon atoms and the double bond between $C_5$ and $C_6$ in the formulae (IIg) and (IIi) are Z and E, respectively), Ⓑ represents a group of the general formula:

 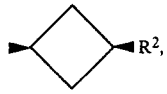
(IIIa) (IIIb)

 
(IIIc) (IIId)

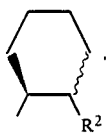 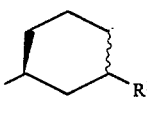 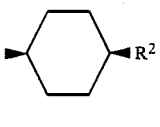
(IIIe) (IIIf) (IIIg)

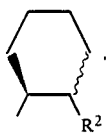 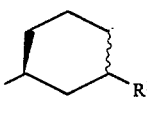 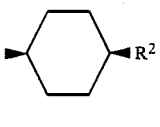
(IIIh) (IIIi) (IIIj)

(wherein $R^2$ represents a straight- or branched-chain alkyl group of 1 to 8 carbon atoms), n represents zero, or an integer of 1 or 2 and the double bond between $C_{13}$ and $C_{14}$ in the formula (I) is E; with the exclusion of the compound wherein Ⓐ represents a group of the formula (IIe) in which R¹ represents a hydrogen atom, Ⓑ represents a group of the formula:

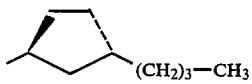

and n is zero), and non-toxic salts thereof when R¹ represents a hydrogen atom, and non-toxic acid addition salts thereof when Ⓐ represents a group of the formula (IIh), and cyclodextrin clathrates thereof.

In the above structural formulae or in the other structural formulae in this specification,

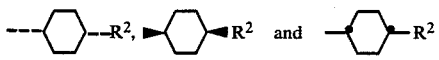

mean the same configuration, and indicate that two substituents are attached to the cyclohexyl group in cis configuration to each other, and

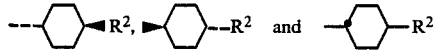

mean the same configuration, and indicate that two substituents are attached to the cyclohexyl group in trans configurations to each other. The cyclobutyl group is shown in a similar manner.

Compounds of the general formula (I) wherein Ⓐ represents a group of the formula: (IIa), (IIb), (IIc), (IId), (IIe), (IIf), (IIg), (IIh) and (IIi) can be called PGA, PGD, PGE, PGF, 6-keto-PGE₁, 6-keto-PGF$_{1\alpha}$, PGI₂, 6,9α-nitrilo-PGI₁ and 6,9α-methano-PGI₂ derivatives, and compounds wherein Y represents a trans-vinylene group can be called trans-Δ² compounds.

Furthermore, the compounds of the present invention can be named as derivatives of a prostanoic acid. For example, the compound of the formula:

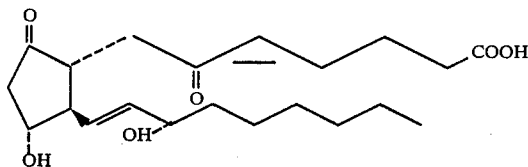

can be called (13E)-(11α,15α)-6,9-dioxo-11,15-dihydroxy-15-[(1S,3R)-3-propylcyclopentyl]-16,17,18,19,20-pentanorprost-13-enoic acid, and the compound of the general formula:

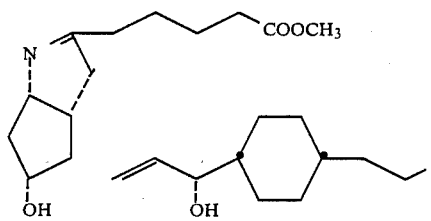

can be called (13E)-(9α,11α,15α)-6,9-nitrilo-11,15-dihydroxy-15-(cis-4-propylcyclohexyl)-16,17,18,19,20-pentanorprost-13-enoic acid methyl ester.

The PG skeleton represented by Ⓐ in the general formula I is preferably a group of the formula (IIc), (IId), (IIe), (IIf), (IIg), (IIh) or (IIi), and more preferably a group of the formula (IId), (IIe), (IIh) or (IIi).

In the group of the formula Ⓐ, as the alkyl group represented by R¹, there may be mentioned methyl, ethyl, propyl, butyl and isomers thereof. R¹ is preferably a hydrogen atom. More preferably R¹ is a hydrogen atom or a methyl group.

In the general formula (I) the alkyl-substituted cycloalkyl group represented by Ⓑ is preferably a cyclopentyl group of the formula (IIIc) or (IIId) or a cyclohexyl group of the fromula (IIIe), (IIIf) or (IIIg), and more preferably a group of the formula (IIId), (IIIf) or (IIIg).

In the group of the formula Ⓑ, as the alkyl group represented by R², there may be mentioned methyl, ethyl, propyl, butyl, pentyl, hexyl, heptyl, octyl and isomers thereof; a straight-or branched-chain alkyl group of 1 to 4 carbon atoms is preferred.

As a preferred group represented by the formula Ⓑ, there may be mentioned:

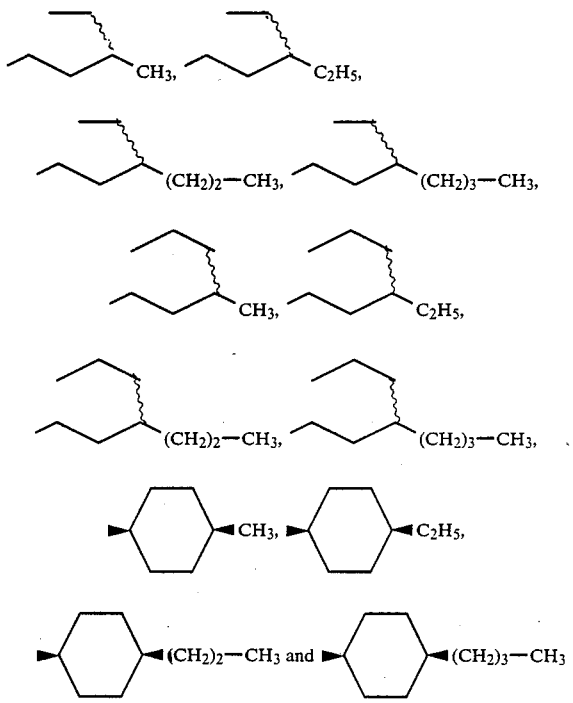

In the general formula (I), n is preferably zero, 1 or 2, and more preferably zero.

Accordingly, as a preferred group of compounds of the present invention, there may be mentioned PG analogues of the general formula:

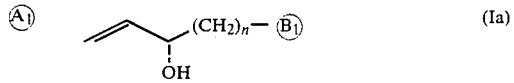

(wherein Ⓐ₁ represents a group of the general formula IIc, IId, IIe, IIf, IIg, IIh or IIi, (wherein X, Y and R¹ are as hereinbefore defined, Ⓑ₁ represents a group of the general formula IIIc, IIId, IIIe, IIIf or IIIg in each of which R² represents a group $R^{2a}$ which represents a straight- or branched-chain alkyl group of 1 to 4 carbon atoms) and n is as hereinbefore defined, or non-toxic salts thereof, or non-toxic acid addition salts thereof, or cyclodextrin clathrates thereof.

As a more preferred group of compounds of the present invention, there may be mentioned PG analogues of the general formula:

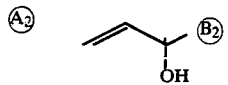 (Ib)

(wherein $A_2$ represents a group of the general formula IId, IIe, IIh or IIi (wherein X and Y are as hereinbefore defined, and R¹ represents a group $R^{1a}$ which represents a hydrogen atom or a methyl group), and $B_2$ represents a group of the general formula IIId, IIIf or IIIg (wherein R² represents a group $R^{2a}$ which represents a straight- or branched-chain alkyl group of 1 to 4 carbon atoms)), or non-toxic salts thereof, or non-toxic acid addition salts thereof, or cyclodextrin clathrates thereof.

The compounds of the general formula (I) may be prepared by methods known per se. By the expression "methods known per se" as used in this specification is meant methods heretofore used or described in the literature.

Compounds of the general formula (I) may be prepared by synthetic routes starting from compounds of the general formula:

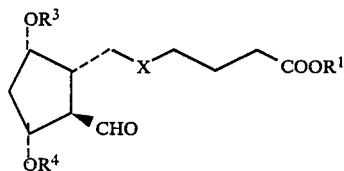 (IV)

(wherein R³ represents a hydrogen atom or an acyl group, R⁴ represents a hydrogen atom or a hydroxy-protecting group which is eliminated under an acidic condition, e.g., a tetrahydropyran-2-yl group, and the other symbols are as hereinbefore defined) or compounds of the general formula:

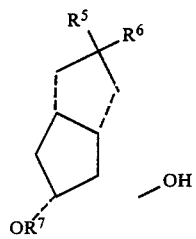 (V)

(wherein one of R⁵ and R⁶ represents an acetyl group and the other represents a hydrogen atom, or R⁵ and R⁶ together represent an oxo group, and R⁷ represents a hydroxy-protecting group which is eliminated under an acidic or alkaline condition, e.g. tetrahydropyran-2-yl, tert-butyldimethylsilyl or benzoyl group, and a dialkyl phosphonate of the general formula:

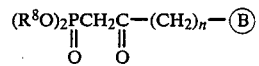 (VI)

(wherein R⁸ represents an alkyl group of 1 to 4 carbon atoms, preferably a methyl or ethyl group, and the other symbols are as hereinbefore defined), by the methods described in the following patent specifications, or obvious modifications thereof:

(1) when Ⓐ represents a group of the formula (IIa), (IIc) and (IId), as described in Japanese Patent Kokai No. 52-27753 and British Patent Specification No. 1545213;

(2) when Ⓐ represents a group of the formula (IIb), as described in Japanese Patent Kokai Nos. 58-216155 and 59-5154, and European Patent Publication Nos. 97023 and 99672;

(3) when Ⓐ represents a group of the formula (IIe), as described in Japanese Patent Kokai No. 54-44639 and British Patent Specification No. 2079268;

(4) when Ⓐ represents a group of the formula (IIf), as described in Japanese Patent Kokai No. 53-127441 (Derwent Abstract No. 90273A);

(5) when Ⓐ represents a group of the formula (IIg), as described in Japanese Patent Kokai No. 53-103464 and British Patent Specification No. 1598953;

(6) when Ⓐ represents a group of the formula (IIh), as described in Japanese Patent Kokai No. 54-125653 and British Patent Specification No. 2016456;

(7) when Ⓐ represents a group of the formula (IIi), as described in Japanese Patent Kokai Nos. 54-130543, 55-64541 and 59-51276, British Patent Specification No. 2017699, and European Patent Publication No. 105651.

Optical isomers and geometric isomers which occur in the group represented by Ⓑ, may be resolved and separated to a desired isomer at the stage of a phosphonate of the general formula (VI), and then, by using the obtained isomer, the subsequent reactions for synthesizing PGs may be carried out; or the reactions for synthesizing PGs may be carried out by using a phosphonate containing a mixture of each isomer, and resolution and separation may be conducted at an appropriate step during reactions; or the two methods described above may be appropriately combined.

Methods for the resolution of optical isomers or methods for the separation of geometric isomers are well known per se. For example, they may be carried out by conventional means, e.g., by high pressure liquid, thin layer or column chromatography on silica gel or on magnesium silicate, or by known methods for optical resolution (cf. Tables of resolving agents and optical resolutions, University of Notre dame press (1972)).

Starting materials of the general formula (IV) may be prepared by the methods described in Japanese Patent Kokai No. 50-137961 and British Patent Specification No. 1482928, or obvious modifications thereof.

Starting materials of the general formula (V) may be prepared by the methods described in Japanese Patent Kokai Nos. 54-130543, 55-64541 and 59-51276, British Patent Specification No. 2017699, and European Patent Publication No. 105651, or obvious modifications thereof.

Dialkyl phosphonates of the general formula (VI) may be prepared by reacting a compound of the general formula:

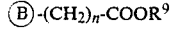 (VII)

(wherein $R^9$ represents an alkyl group of 1 to 4 carbon atoms, preferably a methyl or ethyl group, and (B) and n are as hereinbefore defined) with a dialkyl methylphosphonate of the formula:

$$(R^8O)_2\underset{\underset{O}{\|}}{P}-CH_3$$

(in which $R^8$ is as hereinbefore defined), in an organic solvent such as tetrahydrofuran, in the presence of a base such as n-butyllithium, at a temperature from $-78°$ C. to room temperature.

Carboxylic esters of the general formula (VII) in which n is an integer of 1 may be prepared from the carboxylic ester of the general formula (VII) in which n is zero, by the sequence of reaction steps illustrated in the following Scheme 1. In Scheme 1, LAH means the reduction by using lithium aluminium hydride, and $R^{10}$ represents a tosyl or mesyl group and the other symbols are as hereinbefore defined.

Scheme 1:

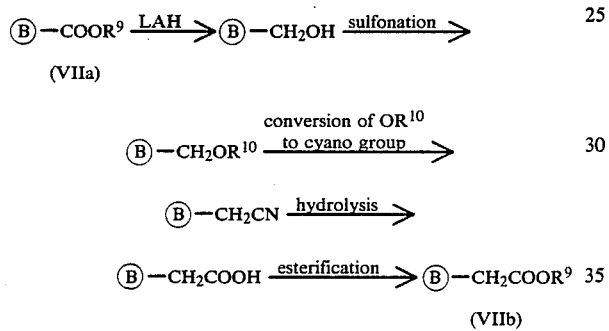

(VIIb)

Each step may be carried out by methods known per se.

Carboxylic esters of the general formula (VII) in which n is an integer of 2 may be prepared by repetition of the same procedure as illustrated in Scheme 1, by using a carboxylic ester of the general formula (VII) in which n is an integer of 1, i.e., a compound of the general formula (VIIb), as starting material.

Carboxylic esters of the general formula (VIIa) may be prepared by methods known per se, for example, by the sequence of reaction steps illustrated in the following Scheme 2 to 5, wherein $R^{11}$ represents an alkyl group of 1 to 4 carbon atoms (preferably methyl group), $R^{12}$ represents a hydroxy-protecting group which is eliminated under an acidic condition (preferably, tetrahydropyran-2-yl group), $R^{2b}$ represents a hydrogen atom or a straight- or branched-alkyl group of 1 to 7 carbon atoms, $R^{2c}$ represents a straight- or branched-chain alkyl group of 1 to 7 carbon atoms, LDA represents a lithium dialkylamide (for example, lithium diisopropylamide), X represents a halogen atom (for example, bromine or iodine atom), m represents an integer of 1 to 4, p represents an integer of 2 to 4, q represents an integer of 1 to 4, and the other symbols are as hereinbefore defined.

Scheme 2: 2-Substituted cycloalkanecarboxylic acid

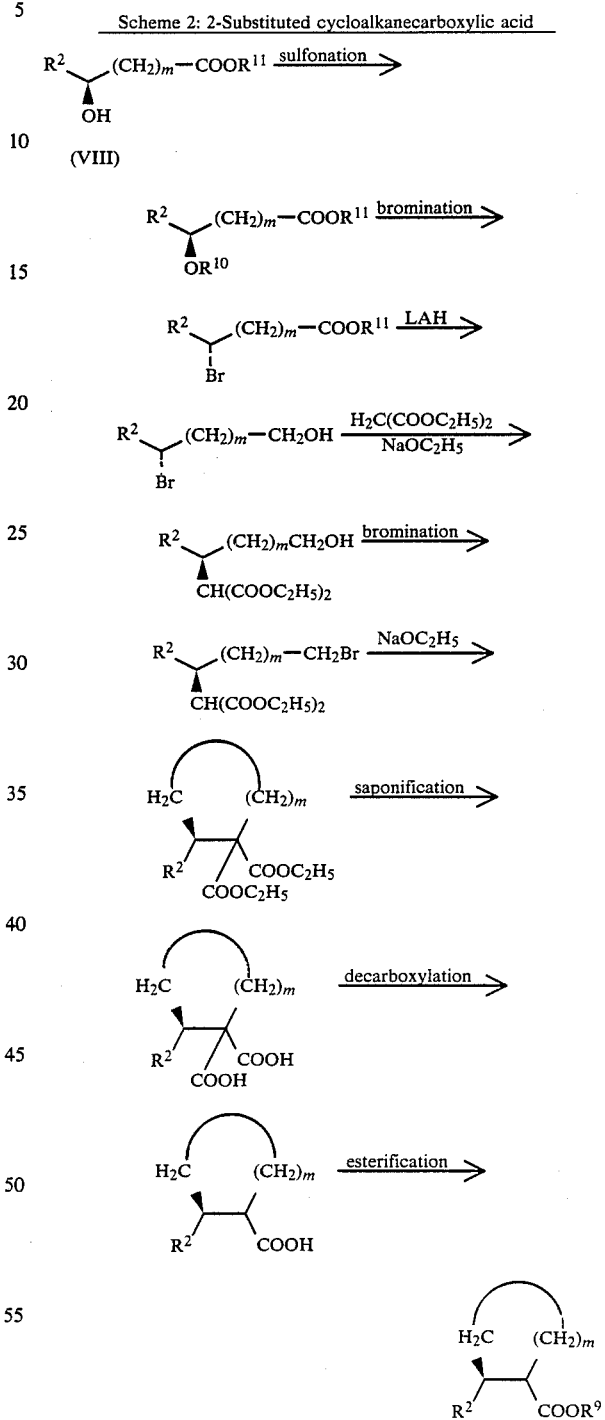

(VIII)

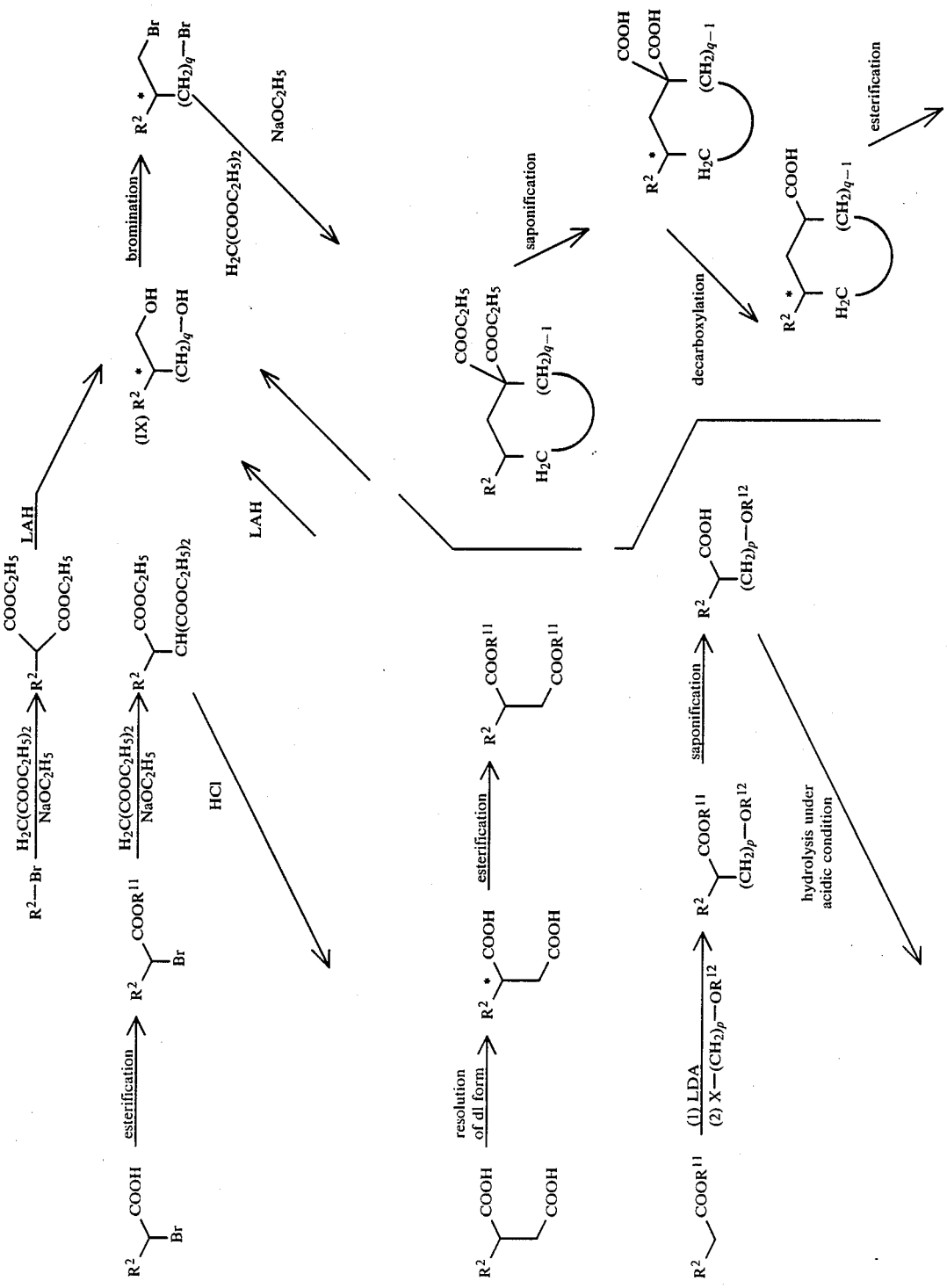

-continued
Scheme 3: 3-Substituted cycloalkanecarboxylic acid
$R^2 \underset{(CH_2)_p-OH}{\overset{COOH}{\diagup}}$ $\xrightarrow{\text{resolution of dl form}}$ $R^2 \underset{(CH_2)_p-OH}{\overset{*}{\diagup}} COOH$ $\xrightarrow{\text{esterification}}$ $R^2 \underset{(CH_2)_p-OH}{\overset{*}{\diagup}} COOR^{11}$ $\xrightarrow{\text{LAH}}$ (X)
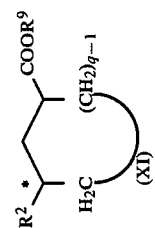
(XI)

Scheme 4: 4-Substituted cyclohexanecarboxylic acid
(Procedure 1)
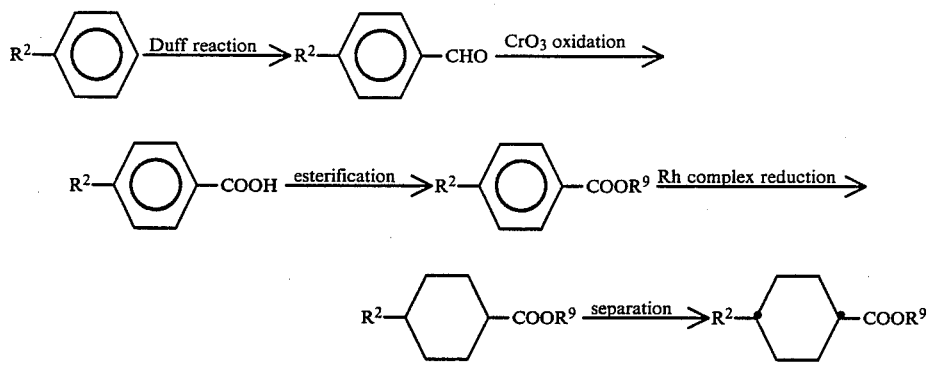
(Procedure 2)
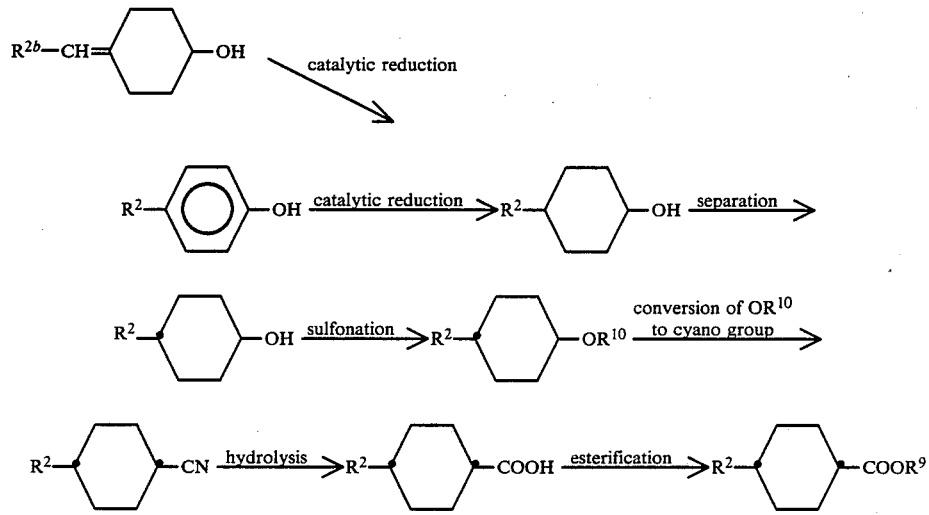
(Procedure 3)
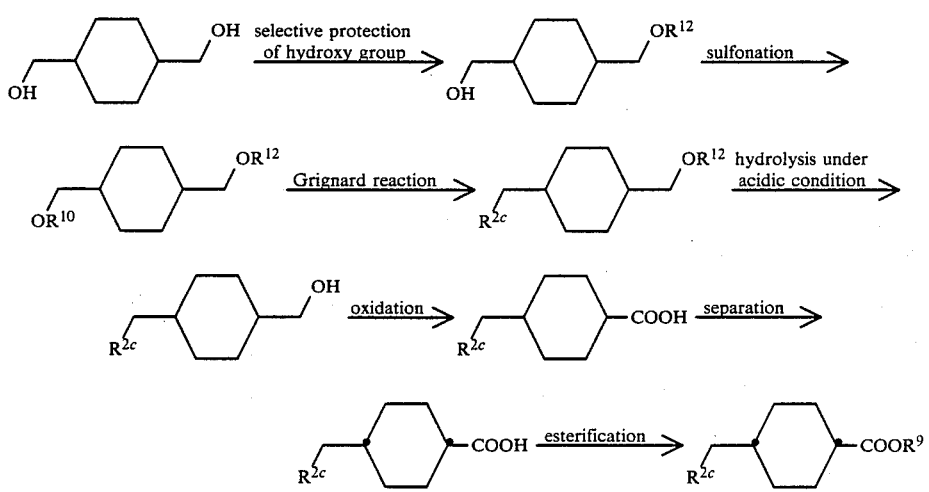
Scheme 5: 4-Substituted cycloheptanecarboxylic acid
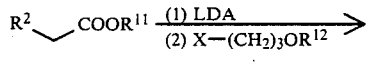
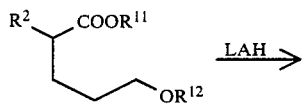
-continued
Scheme 5: 4-Substituted cycloheptanecarboxylic acid
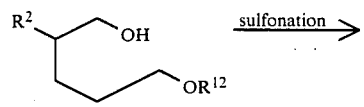

-continued
Scheme 5: 4-Substituted cycloheptanecarboxylic acid

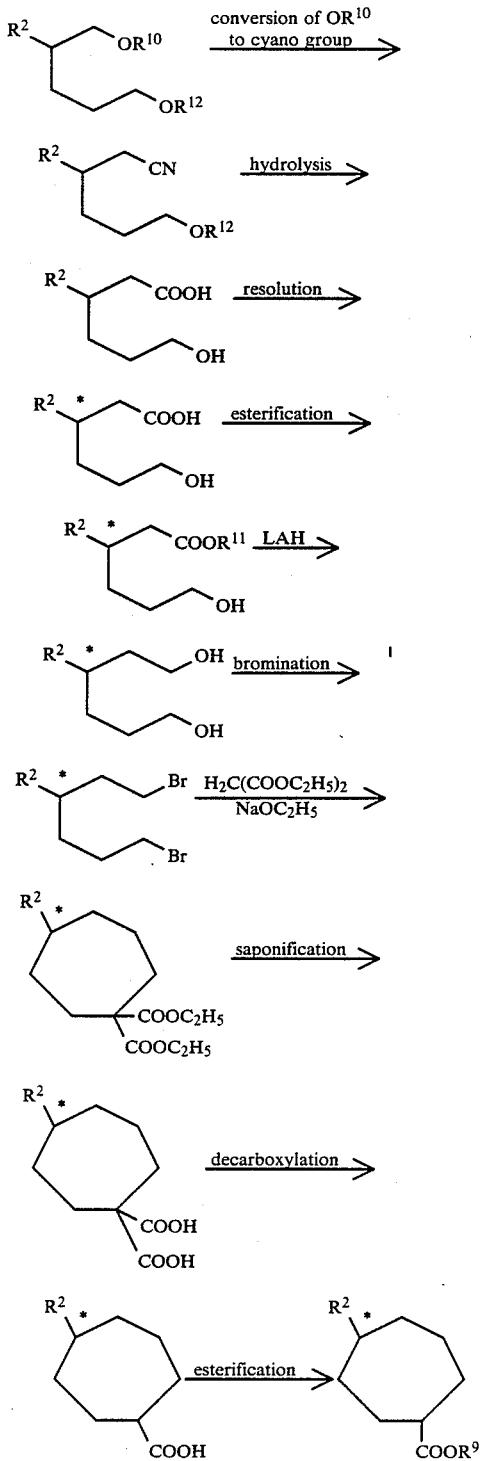

In Schemes 2 to 5, each reaction may be carried out by methods known per se. Compounds used as starting materials in each reaction are known per se, or may be easily prepared from known compounds by methods known per se.

The resolution of dl-compounds or the separation of the mixture of cis-form and trans-form may be carried out at the desired step. In the schemes, the preferred steps at which resolution or separation are effected are shown, but resolution or separation may be carried out at other steps.

In Scheme 2, the process for the preparation of 2S-alkyl-substituted cycloalkanecarboxylic acids is illustrated, and 2R-alkyl-substituted cycloalkanecarboxylic acids may be prepared by the same procedure as described in Scheme 2 by using the corresponding compound of the general formula (VIII) as starting material.

Compounds of the general formula (VIII) in which m represents an integer of 2, 3 or 4, may be prepared by repetition of the same procedure as illustrated in Scheme 1, by using a compound of the general formula (VIII) in which m represents an integer of 1.

In Scheme 3, there is no asymmetric carbon atom in the compound of the general formula (IX) in which q represents an integer of 1. In the case of the compound in which q is an integer of 1, the separation of cis-form from trans-from is preferably carried out on the compound of the general forula (X) or (XI).

According to a feature of the present invention compounds of general formula I may be prepared as follows:

(I) when Ⓐ represents a group of the formula (IIa), (IIc) or (IId), by the hydrolysis of a compound of the general formula:

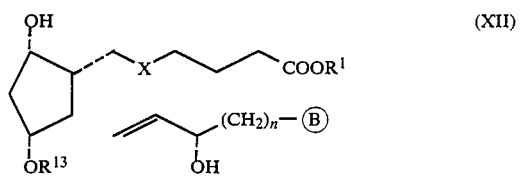

(XII)

(wherein $R^{13}$ represents a hydroxy-protecting group which is eliminated under acidic conditions, and the other symbols are as hereinbefore defined), or by the hydrolysis of a compound of the general formula:

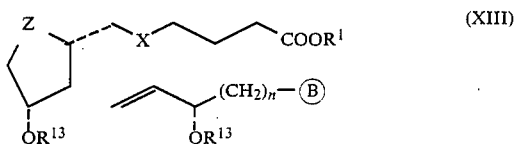

(XIII)

(wherein Z represents

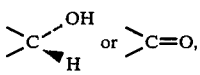

and the other symbols are as hereinbefore defined), or by the hydrolysis of a compound of the general formula:

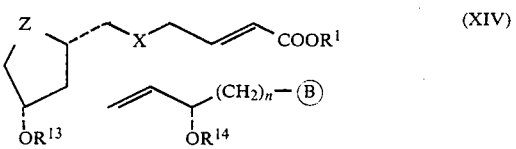

(XIV)

(wherein $R^{14}$ represents a hydrogen atom or a hydroxy-protecting group which is eliminated under acidic conditions, and the other symbols are as hereinbefore defined), followed optionally by esterification, by saponification or by the conversion of a PGE compound wherein (A) represents a group of the formula (IIc) to a PGA compound of general formula (I) wherein (A) represents a group of the formula (IIa) by methods known per se;

(II) when (A) represents a group of the formula (IIb), by the hydrolysis of a compound of the general formula:

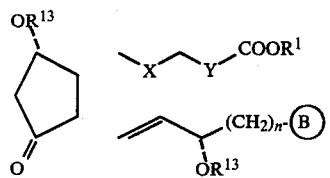
(XV)

(wherein the various symbols are as hereinbefore defined), followed optionally by esterification;

(III) when (A) represents a group of the formula (IIe) or (IIf), by the hydrolysis of a compound of the general formula:

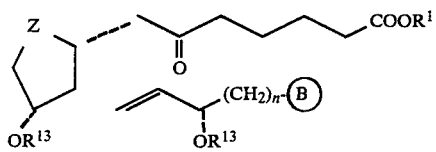
(XVI)

(wherein the various symbols are as hereinbefore defined), or by the hydrolysis of a compound of the general formula:

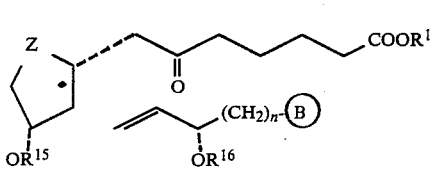
(XVII)

(wherein $R^{15}$ and $R^{16}$, which may be the same or different, each represent a hydroxy-protecting group which is eliminated under acidic conditions, or a trimethylsilyl group, with the proviso that at least one of the symbols $R^{15}$ and $R^{16}$ represents a trimethylsilyl group, and the other symbols are as hereinbefore defined), followed optionally by esterification;

(IV) when (A) represents a group of the formula (IIg), by the dehydrohalogenation of a compound of the general formula:

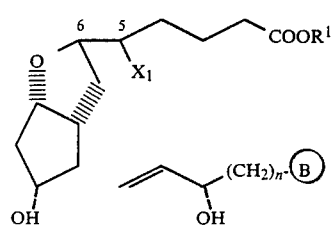
(XVIII)

(wherein $X_1$ represents a bromine or iodine atom, the absolute configuration of $C_5$ and $C_6$ are (5R, 6R) or (5S, 6S) or a mixture thereof, and the other symbols are as hereinbefore defined), followed optionally by esterification;

(V) when (A) represents a group of the formula (IIh), by the cyclisation of a compound of the general formula:

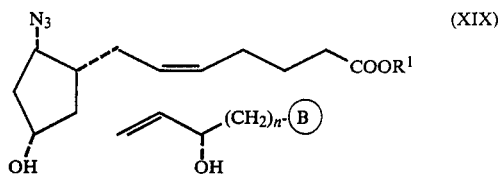
(XIX)

(wherein the various symbols are as hereinbefore defined), followed optionally by esterification or saponification;

(VI) when (A) represents a group of the formula (IIi), by the hydrolysis of a compound of the general formula:

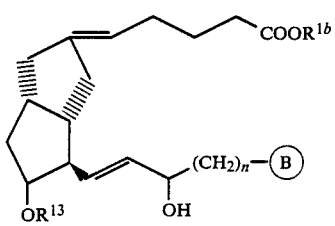
(XX)

(wherein $R^{1b}$ represents a straight- or branched-chain alkyl group of 1 to 4 carbon atoms, and the other symbols are as hereinbefore defined), or by the hydrolysis of a compound of the general formula:

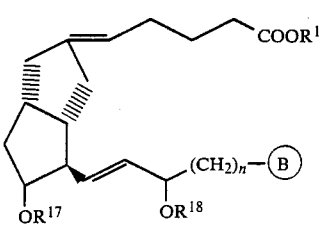
(XXI)

(wherein $R^{17}$ represents a hydrogen atom or a hydroxy-protecting group which is eliminated under acidic conditions, $R^{18}$ represents a hydroxy-protecting group which is eliminated under acidic conditions, and the other symbols are as hereinbefore defined), or by the hydrolysis of a compound of the general formula:

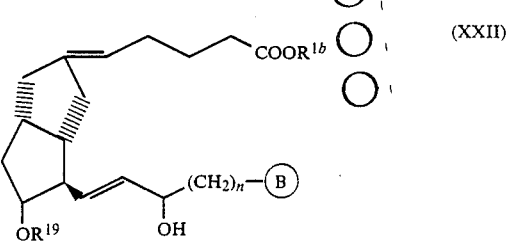
(XXII)

(wherein $R^{19}$ represents a hydroxy-protecting group which is eliminated under alkaline conditions, and the other symbols are as hereinbefore defined), or by the reduction of a compound of the general formula:

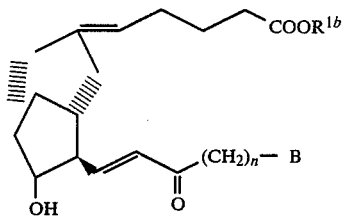

(XXIII)

(wherein the various symbols are as hereinbefore defined), followed optionally by esterification or saponification.

The hydroxy-protecting group represented by $R^{13}$, $R^{14}$, $R^{15}$, $R^{16}$ and $R^{18}$ is preferably tetrahydropyran-2-yl. The hydroxy-protecting group represented by $R^{17}$ is preferably tetrahydropyran-2-yl or tert-butyldimethylsilyl. The hydroxy-protecting group represented by $R^{19}$ is preferably benzoyl.

Compounds of the general formulae (XII) to (XXIII) are prepared by the synthetic routes hereinbefore referred to, starting from compounds of general formulae IV, V and VI.

The hydrolysis under acidic conditions of the groups $OR^{13}$, $OR^{14}$ (when $R^{14}$ is other than a hydrogen atom), $OR^{15}$, $OR^{16}$, the trimethylsilyl group, $OR^{17}$ (when $OR^{17}$ is other than a hydrogen atom), and $OR^{18}$, may be carried out by mild hydrolysis with (1) an aqueous solution of an organic acid such as acetic acid, propionic acid, oxalic acid or p-toluenesulphonic acid, or an aqueous solution of an inorganic acid such as hydrochloric acid, sulphuric acid or phosphoric acid, advantageously in the presence of an inert organic solvent miscible with water, e.g. a lower alkanol such as methanol or ethanol, preferably methanol, or an ether such as 1,2-dimethoxyethane, dioxan or tetrahydrofuran, preferably tetrahydrofuran, at a temperature from ambient to 75° C., or (2) an anhydrous solution of an organic acid such as p-toluenesulphonic acid or trifluoroacetic acid in a lower alkanol such as methanol or ethanol at a temperature from 10° C. to 45° C., or (3) an anhydrous solution of p-toluenesulphonic acid-pyridine complex in a lower alkanol such as methanol or ethanol at a temperature from 10° to 60° C. Advantageously the mild hydrolysis under acidic conditions may be carried out with a mixture of dilute hydrochloric acid and tetrahydrofuran, a mixture of dilute hydrochloric acid and methanol, a mixture of acetic acid, water and tetrahydrofuran, a mixture of phosphoric acid, water and tetrahydrofuran, a mixture of p-toluenesulphonic acid and methanol or a mixture of p-toluenesulphonic acid-pyridine complex and methanol.

The hydrolysis under alkaline conditions of the group $OR^{19}$ may be carried out by reaction with an aqueous solution of an alkali metal, e.g. sodium or potassium, or an alkaline earth metal, e.g. calcium or barium, hydroxide or carbonate in the presence of a water-miscible solvent, e.g. an ether such as dioxan or tetrahydrofuran or an alkanol containing 1 to 4 carbon atoms, such as methanol or ethanol, at a temperature from −10° C. to 70° C., preferably at ambient temperature.

The dehydrohalogenation of a compound of the general formula (XVIII) may be carried out with a known dehydrohalogenation reagent, for example, (1) when $X_1$ represents a bromine atom, a bicycloamine such as DBU (i.e. 1,5-diazabicyclo[5.4.0]undecene-5), DBN (i.e. 1,5-diazabicyclo[4.3.0]nonene-5) or DABCO (i.e. 1,4-diazabicyclo[2.2.2]octane), or an alkali metal, e.g. sodium or potassium, alcoholate containing from 1 to 4 carbon atoms, or (2) when $X_1$ represents an iodine atom, a bicycloamine such as DBN, DBU or DABCO, or an alkali metal, e.g. sodium or potassium, alcoholate containing from 1 to 4 carbon atoms, superoxide, carbonate, hydroxide, benzoate, acetate, trifluoroacetate or bicarbonate, or silver acetate, or tetramethylammonium superoxide. The reaction may be carried out at a temperature from ambient to 110° C., preferably at a temperature from ambient to 80° C., and (1) when the reagent is a bicycloamine, optionally in the presence of an inert organic solvent, preferably in the absence of an inert organic solvent or in the presence of toluene or benzene, or (2) when the reagent is other than a bicycloamine, in the presence of an inert organic solvent, e.g. an alkanol containing from 1 to 4 carbon atoms, such as methanol or ethanol, or N,N-dimethylformamide.

When the reaction is carried out in the presence of a solvent, the reaction mixture may be concentrated under reduced pressure at a low temperature, e.g. at 0° C. to 5° C. after the reaction. The residue thus obtained or the reaction mixture obtained when the reaction is carried out in the absence of a solvent, may be adjusted, (1) when $R^1$ represents a hydrogen atom, to pH 5 to 7 or, (2) when $R^1$ represents an alkyl group, to pH 7 to 9 with an aqueous solution of an acid, e.g. dilute hydrochloric acid, and/or phosphate buffer, and extracted with an easily removable organic solvent such as diethyl ether. The extract, when $R^1$ represents a hydrogen atom, may be dried to give a solution of the desired $PGI_2$ analogue. The extract, when $R^1$ represents an alkyl group, may be dried and concentrated under reduced pressure to give the desired $PGI_2$ analogue. If desired, a product wherein $R^1$ represents an alkyl group, may be purified by thin layer or column chromatography on silica gel or magnesium silicate pretreated with triethylamine to give the pure $PGI_2$ analogue.

The cyclisation of a compound of the general formula (XIX) may be carried out in an inert organic solvent, e.g. toluene, benzene or acetonitrile, at a temperature from ambient to 110° C.

The reduction of a compound of the general formula (XXIII) may be carried out by using any suitable reducing reagent such as sodium borohydride, potassium borohydride, lithium borohydride, zinc borohydride, lithium tri-tert-butoxyaluminium hydride, lithium trimethoxyaluminium hydride, sodium cyanoborohydride, potassium tri-sec-butylborohydride, lithium aluminium hydride-quinine complex, (−)-isobornyloxymagnesium iodide in an inert organic solvent, e.g. an alkanol containing from 1 to 4 carbon atoms such as methanol, ethanol or isopropanol, or an ether such as tetrahydrofuran, dioxan or 1,2-dimethoxyethane, or a mixture of two or more such solvents, at a temperature from −78° C. to ambient. Preferably, the reduction is effected using diisobornyloxyaluminiumisopropoxide (described in our Japanese Patent Kokai No. 54-76552), or a diisobutyl(alkyl-substituted or unsubstituted) phenoxyaluminium [described in our Japanese Patent Kokai No. 54-154739 and J. Org. Chem., 44, 1363(1979)], or a lithium 1,1′-binaphthyl-2,2′-dioxyaluminium hydride [described in J. Amer. Chem. Soc., 101, 5843(1979)]. The product thus obtained is a mixture of isomers in which the 15-hydroxy group is in α- or β-configuration and the mixture may be separated by conventional means, for example, by thin layer, column or high-speed liquid chromatography on silica gel to give the desired 15α-hydroxy isomer.

The conversion of the PGE compound to a PGA compound may be carried out by subjecting the PGEs to dehydration using an aqueous solution of an organic or inorganic acid having a higher concentration than that employed for hydrolysing the $OR^{13}$ group of compounds of general formula XII, e.g. 1N hydrochloric acid, if desired in the presence of cupric chloride, or acetic acid, and heating at a temperature of 30° to 60° C. PGA compounds can be also obtained directly from compounds of general formula XIII and XIV, wherein Z represents

when such stronger acidic conditions are utilized to hydrolyze the $OR^{13}$ groups as the intermediate PGEs will then be dehydrated in situ to PGA compounds.

The esterification of the acids of the general formula (I) may be carried out by methods known per se, for example by reaction with (i) the appropriate diazoalkane in an inert organic solvent, e.g. diethyl ether, at a temperature of from −10° to 25° C. and preferably 0° C., (ii) the appropriate alcohol in the presence of dicyclohexylcarbodiimide as condensing agent, or (iii) the appropriate alcohol following formation of a mixed anhydride by adding a tertiary amine and pivaloyl halide or an alkylsulphonyl or arylsulphonyl halide (cf. British Patents Nos. 1362956 and 1364125).

The saponification of the esters of the general formula (I) wherein (A) represents a group of the formula (IId), (IIh) or (IIi), to the corresponding acids, may be carried out by reaction with an aqueous solution of an alkali metal, e.g. sodium or potassium, or an alkaline earth metal, e.g. calcium or barium, hydroxide or carbonate in the presence of a water-miscible solvent, e.g. an ether such as dioxane or tetrahydrofuran or a lower alkanol such as methanol or ethanol at a temperature from −10° to 70° C. preferably at ambient temperature.

The saponification of the esters of the general formula (I) wherein (A) represents a group of the formula (IIc) to the corresponding acid, may be carried out by using bakers' yeast [cf. C. J. Sih et al, J. Amer. Chem. Soc., 94, 3643–3644(1972)].

Cyclodextrin clatharates of PG analogues of the general formula (I) may be prepared by using α-, β-or γ-cyclodextrin, or a mixture thereof by methods described in the specifications of British Patent Nos. 1351238 and 1419221. Conversion into cyclodextrin clathrates serves to increase the stability and the solubility of PG analogues of the general formula (I), and therefore facilitates their use as pharmaceuticals.

The compounds of general formula (I) wherein $R^1$ represents a hydrogen atom may, if desired, be converted by known methods into salts. Preferably the salts are non-toxic salts and water-soluble. Suitable non-toxic salts include the alkali metal, e.g. sodium or potassium, salts, the alkaline earth metal, e.g. calcium or magnesium, salts and ammonium salts, and pharmaceutically acceptable, (i.e. non-toxic) amine salts. Amines suitable for forming such salts with a carboxylic acid are well known and include organic amine salts, for example, tetraalkylammonium, such as tetramethylammonium, salts, methylamine salts, dimethylamine salts, cyclopentylamine salts, benzylamine salts, phenethylamine salts, piperidine salts, monoethanolamine salts, diethanolamine salts, lysine salts, arginine salts or N-methylglucamine salts.

Salts may be prepared from the compounds of general formula (I) wherein $R^1$ represents a hydrogen atom, by known methods, for example by reaction of stoichiometric quantities of an acid of general formula (I) and the appropriate base, e.g. an alkali metal hydroxide or carbonate, ammonium hydroxide, ammonia or an organic amine, in a suitable solvent.

The compounds of general formula (I) wherein (A) represents a group of the formula (IIh) may, if desired, be converted by known methods into acid addition salts, which are preferably non-toxic salts and water-soluble.

Examples of suitable non-toxic acid addition salts are the salts with inorganic acids, such as hydrochloric acid, hydrobromic acid, hydroiodic acid, sulphuric acid, phosphoric acid and nitric acid, and the salts with organic acids such as acetic acid, propionic acid, lactic acid, tartaric acid, citric acid, benzoic acid, methanesulphonic acid, ethanesulphonic acid, benzenesulphonic acid, toluenesulphonic acid, isethionic acid, glucuronic acid and gluconic acid.

Acid addition salts may be prepared from the compounds of general formula (I) wherein (A) represents a group of the formula (IIh), by known methods, for example by reaction of stoichiometric quantities of a compound of the general formula (I) wherein (A) represents a group of the formula (IIh) and the appropriate acid in a suitable solvent.

The PG analogues of the general formula (I), non-toxic salts thereof, non-toxic acid-addition salts thereof and cyclodextrin clathrates thereof having a specific steric configuration show stronger pharmacological activity than the corresponding isomers which are not embraced by the present invention. Furthermore, the strong activity extends to all of the pharmacological properties typical of the PGs.

The PG analogues of the general formula (I), non-toxic salts thereof, non-toxic acid addition salts thereof and cyclodextrin clathrates thereof have advantages in hypotensive effect and inhibitory effect on blood platelet aggregation, and, therefore, are particularly useful as hypotensive agents for the treatment of hypertension, and as inhibitory agents of blood platelet aggregation for the treatment of disorders of the peripheral circulation and for the prevention and treatment of thrombosis, cardiostenosis, myocardial infarction and arteriosclerosis.

For example, the results of standard laboratory tests (i) inhibitory effect on adenosine diphosphate (ADP)-induced blood platelet aggregation in platelet-rich plasma of rats (in vitro) and (ii) hypotensive effect by intraveneous administration to the allobarbital-anaesthetized dog (in vivo), of the compounds of the present invention (isomers in the SR-form, SS-form and cis-form) and the compounds for comparison (isomers in the RR-form, RS-form and trans-form), are shown in the following tables. Furthermore, the effects of mixtures of each isomer are also shown in the tables for reference. In the tables, all the activities are indicated relative to the activity of $PGE_1$, taken as 1.

TABLE 1

Comparison of the activities in the compound of the formula:

| Productive Example or Reference Example | | Inhibitory Effect on Blood Platelet Aggregation (Rats) (PGE$_1$ = 1) | Hypotensive Effect (Dogs) (PGE$_1$ = 1) |
|---|---|---|---|
| <br>(Present Invention) | Example 2 | 128 | 21 |
| 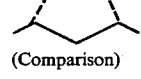<br>(Comparison) | Reference Example 15 | 36.4 | 12 |
| 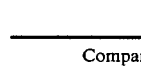<br>(Present Invention) | Example 3(a) | 230 | 43 |
| <br>(Comparison) | Example 3(b) | 29.4 | 11 |
|  (1)<br>(Reference) | Example 2(b) in British Patent No. 2079268 | 58 | 13 |

TABLE 2

Comparison of the activities in the compound of the formula:

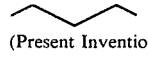

| Productive Example or Reference Example | | Inhibitory Effect on Blood Platelet Aggregation (Rats) (PGE$_1$ = 1) | Hypotensive Effect (Dogs) (PGE$_1$ = 1) |
|---|---|---|---|
| 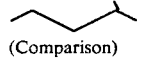<br>(Present Invention) | Example 5 | 28.4 | 8.0 |
| 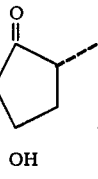<br>(Comparison) | Reference Example 26 | 21.3 | 4.6 |

TABLE 2-continued

Comparison of the activities in the compound of the formula:

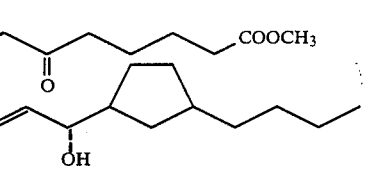

| Productive Example or Reference Example | | Inhibitory Effect on Blood Platelet Aggregation (Rats) (PGE$_1$ = 1) | Hypotensive Effect (Dogs) (PGE$_1$ = 1) |
|---|---|---|---|
| <br>(Present Invention) | Example 6(a) | 99.6 | 14.5 |
| <br>(Comparison) | Example 6(b) | 11.1 | 2.5 |
|  (1)<br>(Reference) | Example 2 in British Patent No. 2079268 | 25.8 | 7.1 |

TABLE 3

Comparison of the activities in the compound of the formula:

| Productive Example or Reference Example | | Inhibitory Effect on Blood Platelet Aggregation (Rats) (PGE$_1$ = 1) | Hypotensive Effect (Dogs) (PGE$_1$ = 1) |
|---|---|---|---|
| <br>(Present Invention) | Example 4 | 76.9 | 14.7 |
| <br>(Comparison) | Reference Example 25 | 26.3 | 5.1 |
| 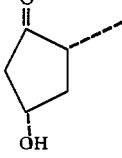 (1)(2)<br>(Reference) | Example 2 in British Patent No. 2079268 | 25.8 | 7.1 |

TABLE 4

Comparison of the activities in the compound of the formula:

| Productive Example or Reference Example | Inhibitory Effect on Blood Platelet Aggregation (Rats) ($PGE_1$ = 1) | Hypotensive Effect (Dogs) ($PGE_1$ = 1) |
|---|---|---|
| Example 7 or 8 (Present Invention) | 7.6 | 0.49 |
| Reference Example 34 (Comparison) | 3.4 | 0.079 |
| (3) Example 2(4) in British Patent No. 2016456 (Reference) | 3.6 | 0.098 |

TABLE 5

Comparison of the activities in the compound of the formula:

| Productive Example or Reference Example | Inhibitory Effect on Blood Platelet Aggregation (Rats) ($PGE_1$ = 1) | Hypotensive Effect (Dogs) ($PGE_1$ = 1) |
|---|---|---|
| Example 10 (Present Invention) | 13.6 | 1.9 |
| Reference Example 38 (Comparison) | 4.48 | 1.0 |
| Example 12 (Present Invention) | 24.1 | 7.2 |
| Reference Example 44 (Comparison) | 2.21 | 0.48 |
| (1) Example 3(2) in British Patent No. 2016456 (Reference) | 7.84 | 1.7 |

TABLE 6

Comparison of the activities in the compound of the formula:

| Productive Example or Reference Example | Inhibitory Effect on Blood Platelet Aggregation (Rats) ($PGE_1$ = 1) | Hypotensive Effect (Dogs) ($PGE_1$ = 1) |
|---|---|---|
| Example 9 (Present Invention) | 8.18 | 0.51 |
| Reference Example 37 (Comparison) | 2.6 | 0.18 |
| Example 11 (Present Invention) | 11.7 | 1.0 |
| Reference Example 43 (Comparison) | 1.35 | 0.14 |

TABLE 6-continued

Comparison of the activities in the compound of the formula:

| Productive Example or Reference Example | Inhibitory Effect on Blood Platelet Aggregation (Rats) ($PGE_1$ = 1) | Hypotensive Effect (Dogs) ($PGE_1$ = 1) |
|---|---|---|
| Example 2(5) in British Patent No. 2016456 (Reference) | 2.82 | 0.35 |

TABLE 7

Comparison of the activities in the compound of the formula:

| Productive Example or Reference Example | Inhibitory Effect on Blood Platelet Aggregation (Rats) ($PGE_1$ = 1) | Hypotensive Effect (Dogs) ($PGE_1$ = 1) |
|---|---|---|
| Example 16 (Present Invention) | 5.83 | 0.54 |
| Reference Example 49 (Comparison) | 2.21 | 0.20 |
| Example 14 (Present Invention) | 9.44 | 0.91 |
| Reference Example 47 (Comparison) | 1.34 | 0.05 |
| Example 3(c) in British Patent No. 2017699 (Reference) | 1.94 | 0.4 |

(1) The formula:

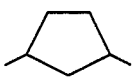

indicates the mixture of the above four isomers, its constitution ratio not being confirmed.

(2) The mixture of four isomers of 15-(3-butylcyclopentyl)-16,17,18,19,20-pentanor-6-keto-$PGE_1$ methyl ester was selected as the most similar compound in chemical structure, of the compounds specifically disclosed in the specification of the British Patent No. 2079268.

(3) The formula:

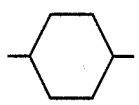

indicates the mixture of the above two isomers, its constitution ratio not being confirmed.

(4) The mixture of four isomers of (5EZ)-15-(3-propylcyclopentyl)-16,17,18,19,20-pentanor-6,9α-methano-$PGI_2$ was selected as the most similar compound in chemical structure, of the compounds specifically disclosed in the specification of the British Patent No. 2017699.

As will be seen from the tables, in the case of the compounds having an alkyl-substituted cyclopentyl group after the 15-position of the PG skeleton, both 16S-isomers have several times to more than ten times stronger an inhibitory effect on blood platelet aggregation and hypotensive effect than the corresponding 16R-isomer, and in the case of the compounds having an alkyl-substituted cyclohexyl group after the 15-position of the PG skeleton, the isomer in cis-form has several times stronger an inhibitory effect on blood platelet aggregation and hypotensive effect than the isomer in trans-form. Furthermore, the compounds of the present invention are generally more potent as compared with the mixtures of each isomer, and, therefore, are understood to be useful enough as pharmaceuticals.

Further, the compounds of the present invention have very weak toxicity, and, therefore, were confirmed to be sufficiently safe and suitable for medical use.

Preferred compounds of the general formula (I) of the present invention are, for example, as follows:

15-[(1S,3R)-3-methylcyclopentyl]-16,17,18,19,20-pentanor-$PGF_{2\alpha}$,
15-[(1S,3R)-3-ethylcyclopentyl]-16,17,18,19,20-pentanor-$PGF_{2\alpha}$,
15-[(1S,3R)-3-propylcyclopentyl]-16,17,18,19,20-pentanor-$PGF_{2\alpha}$,
15-[(1S,3R)-3-butylcyclopentyl]-16,17,18,19,20-pentanor-$PGF_{2\alpha}$,
15-[(1S,3R)-3-methylcyclohexyl]-16,17,18,19,20-pentanor-$PGF_{2\alpha}$,
15-[(1S,3R)-3-ethylcyclohexyl]-16,17,18,19,20-pentanor-$PGF_{2\alpha}$,
15-[(1S,3R)-3-propylcyclohexyl]-16,17,18,19,20-pentanor-$PGF_{2\alpha}$,
15-[(1S,3R)-3-butylcyclohexyl]-16,17,18,19,20-pentanor-$PGF_{2\alpha}$,
15-(cis-4-methylcyclohexyl)-16,17,18,19,20-pentanor-$PGF_{2\alpha}$, 15-(cis-4-ethylcyclohexyl)-16,17,18,19,20-pentanor-PGF$_{2\alpha}$,
15-(cis-4-propylcyclohexyl)-16,17,18,19,20-pentanor-PGF$_{2\alpha}$,
15-(cis-4-butylcyclohexyl)-16,17,18,19,20-pentanor-PGF$_{2\alpha}$,
15-[(1S,3R)-3-methylcyclopentyl]-16,17,18,19,20-pentanor-6-keto-PGE$_1$,
15-[(1S,3R)-3-ethylcyclopentyl]-16,17,18,19,20-pentanor-6-keto-PGE$_1$,
15-[(1S,3R)-3-propylcyclopentyl]-16,17,18,19,20-pentanor-6-keto-PGE$_1$,
15-[(1S,3R)-3-butylcyclopentyl]-16,17,18,19,20-pentanor-6-keto-PGE$_1$,
15-[(1S,3R)-3-methylcyclohexyl]-16,17,18,19,20-pentanor-6-keto-PGE$_1$,
15-[(1S,3R)-3-ethylcyclohexyl]-16,17,18,19,20-pentanor-6-keto-PGE$_1$,
15-[(1S,3R)-3-propylcyclohexyl]-16,17,18,19,20-pentanor-6-keto-PGE$_1$,
15-[(1S,3R)-3-butylcyclohexyl]-16,17,18,19,20-pentanor-6-keto-PGE$_1$,
15-(cis-4-methylcyclohexyl)-16,17,18,19,20-pentanor-6-keto-PGE$_1$,
15-(cis-4-ethylcyclohexyl)-16,17,18,19,20-pentanor-6-keto-PGE$_1$,
15-(cis-4-propylcyclohexyl)-16,17,18,19,20-pentanor-6-keto-PGE$_1$,
15-(cis-4-butylcyclohexyl)-16,17,18,19,20-pentanor-6-keto-PGE$_1$,
15-[(1S,3R)-3-methylcyclopentyl]-16,17,18,19,20-pentanor-6,9α-nitrilo-PGI$_1$,
15-[(1S,3R)-3-ethylcyclopentyl]-16,17,18,19,20-pentanor-6,9α-nitrilo-PGI$_1$,
15-[(1S,3R)-3-propylcyclopentyl]-16,17,18,19,20-pentanor-6,9α-nitrilo-PGI$_1$,
15-[(1S,3R)-3-butylcyclopentyl]-16,17,18,19,20-pentanor-6,9α-nitrilo-PGI$_1$,
15-[(1S,3R)-3-methylcyclohexyl]-16,17,18,19,20-pentanor-6,9α-nitrilo-PGI$_1$,
15-[(1S,3R)-3-ethylcyclohexyl]-16,17,18,19,20-pentanor-6,9α-nitrilo-PGI$_1$,
15-[(1S,3R)-3-propylcyclohexyl]-16,17,18,19,20-pentanor-6,9α-nitrilo-PGI$_1$,
15-[(1S,3R)-3-butylcyclohexyl]-16,17,18,19,20-pentanor-6,9α-nitrilo-PGI$_1$,
15-(cis-4-methylcyclohexyl)-16,17,18,19,20-pentanor-6,9α-nitrilo-PGI$_1$,
15-(cis-4-ethylcyclohexyl)-16,17,18,19,20-pentanor-6,9α-nitrilo-PGI$_1$,
15-(cis-4-propylcyclohexyl)-16,17,18,19,20-pentanor-6,9α-nitrilo-PGI$_1$,
15-(cis-4-butylcyclohexyl)-16,17,18,19,20-pentanor-6,9α-nitrilo-PGI$_1$,
15-[(1S,3R)-3-methylcyclopentyl]-16,17,18,19,20-pentanor-6,9α-methano-PGI$_2$,
15-[(1S,3R)-3-ethylcyclopentyl]-16,17,18,19,20-pentanor-6,9α-methano-PGI$_2$,
15-[(1S,3R)-3-propylcyclopentyl]-16,17,18,19,20-pentanor-6,9α-methano-PGI$_2$,
15-[(1S,3R)-3-butylcyclopentyl]-16,17,18,19,20-pentanor-6,9α-methano-PGI$_2$,
15-[(1S,3R)-3-methylcyclohexyl]-16,17,18,19,20-pentanor-6,9α-methano-PGI$_2$,
15-[(1S,3R)-3-ethylcyclohexyl]-16,17,18,19,20-pentanor-6,9α-methano-PGI$_2$,
15-[(1S,3R)-3-propylcyclohexyl]-16,17,18,19,20-pentanor-6,9α-methano-PGI$_2$,
15-[(1S,3R)-3-butylcyclohexyl]-16,17,18,19,20-pentanor-6,9α-methano-PGI$_2$,
15-(cis-4-methylcyclohexyl)-16,17,18,19,20-pentanor-6,9α-methano-PGI$_2$,
15-(cis-4-ethylcyclohexyl)-16,17,18,19,20-pentanor-6,9α-methano-PGI$_2$,
15-(cis-4-propylcyclohexyl)-16,17,18,19,20-pentanor-6,9α-methano-PGI$_2$,
15-(cis-4-butylcyclohexyl)-16,17,18,19,20-pentanor-6,9α-methano-PGI$_2$,
and 15-[(1S,3S)-3-alkylcyclopentyl] compounds corresponding thereto and 15-[(1S,3S)-3-alkylcyclohexyl] compounds corresponding thereto; and their methyl ester; and non-toxic salts thereof, non-toxic acid-addition salts thereof and cyclodextrin clathrates thereof.

EXAMPLES

The following Reference Examples and Examples illustrate, the preparation of compounds of the present invention. In the Reference Examples and Examples, 'bp', 'mp', 'TLC', 'IR', 'NMR', 'MS' and 'HPLC' represent 'boiling point', 'melting point', 'Thin layer chromatography', 'Infrared absorption spectrum', 'Nuclear magnetic resonance spectrum', 'Mass spectrum' and 'High pressure liquid chromatography', respectively.

In structural formulae, 'Ac', 'THP', 'Ts', 'BMS' and 'φ' represent 'acetyl group', 'tetrahydropyran-2-yl group', 'tosyl (p-toluenesulfonyl) group', 'tert-butyldimethylsilyl group' and 'phenyl group', respectively. The group of the formula:

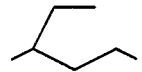

indicates the mixture of the groups of the formulae

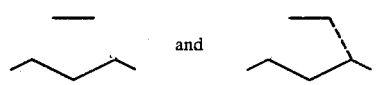

and the group of the formula

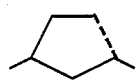

indicates the mixture of the groups of the formulae

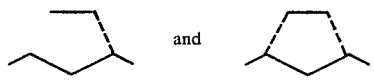

The solvents in parentheses specified in chromatographic separations show the eluents or the developing solvents used: ratios are by volume. Except when specified otherwise, infrared absorption spectra were recorded by the liquid film method and nuclear magnetic resonance spectra were recorded in deuterochloroform (CDCl$_3$) solution.

Reference Example 1

Synthesis of

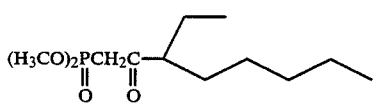

(1) Synthesis of

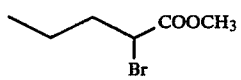

To a solution of 200 g of 2RS-bromopentanoic acid in 445 ml of methanol was added dropwise 160 ml of thionyl chloride over 1.2 hours, being kept a temperature of the reaction mixture at 10° C. to 15° C., and the reaction mixture was stirred for one hour at 10° C. and then for one hour at 20° C. After methanol was removed under reduced pressure, one liter of petroleum ether and 200 ml of water were added to the residue. The organic layer of the solution thus obtained was washed with a saturated aqueous solution of sodium bicarbonate, water and a saturated aqueous solution of sodium chloride, successively, dried over anhydrous magnesium sulfate and concentrated under reduced pressure. The residue was distilled under reduced pressure to give 207.8 g of the title compound having the following physical data:

bp: 75° C.-80° C./18-20 mmHg.

NMR: $\delta$ 4.25 (1H, t), 3.78 (3H, s). 2.14~1.90 (2H, m), 1.65~1.30 (2H, m), 0.95 (3H, t).

(2) Synthesis of

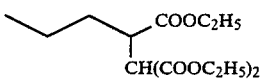

26 g of sodium in limited amounts was added to 700 ml of ethanol over 1.5 hours under cooling with ice. After complete dissolution of sodium, 181 g of diethyl malonate was added dropwise thereto over 30 minutes and the mixture was stirred for 30 minutes. To the solution thus obtained was added dropwise 207 g of the bromo compound (prepared in the above (1)) over 30 minutes at 20° C., and the mixture was stirred for two hours at 35° C. to 45° C. To the reaction mixture was added 400 ml of petroleum ether and the mixture was filtered. After the filtrate was concentrated under reduced pressure, the residue was diluted with one liter of petroleum ether, and was washed with 1N hydrochloric acid, water and a saturated aqueous solution of sodium chloride, successively, dried over anhydrous magnesium sulfate and concentrated under reduced pressure to give 313 g of the crude title compound having the following physical data:

NMR: $\delta$ 4.3 8~4.05 (6H, m), 3.9~3.6 (1H, m), 3.3~3.0 (1H, m), 0.9 (3H, t).

(3) Synthesis of

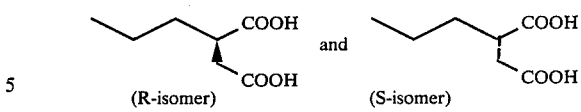

A mixture of 313 g of the tricarboxylic acid ester (prepared in the above (2)), 950 ml of conc. hydrochloric acid and 450 ml of water was mildly refluxed for 22 hours with stirring. The reaction mixture was allowed to stand overnight at room temperature to precipitate crystals. Crystals thus obtained were filtered and the filtrate was concentrated under reduced pressure. To the residue (solid) thus obtained was added 100 ml of water and the solid was then ground and crystals obtained were filtered. Crystals thus obtained were combined with those before obtained, and dried in vacuo to give 134 g of the title compound (mixture of R-isomer and S-isomer) as white solid.

26.4 g of the mixture of R-isomer and S-isomer was dissolved in 1.58 liters of water and allowed to warm till 90° C. 110 g of strychnine in limited amounts was added thereto and the mixture was stirred for 6 hours at the same temperature. After cooling over 3 hours till room temperature, the mixture was allowed to stand overnight at 4° C. Crystals which precipitated were filtered and dissolved in 5.3 liters of water at 80° C. To the solution was added ca. 400 ml of 20% aqueous ammonia to precipitate strychnine. After cooling to room temperature, the precipitates were filtered off and the filtrate was concentrated until its volume became about 100 ml. The residual solution was adjusted to pH 2 with adding conc. hydrochloric acid, and then extracted with ethyl acetate. The extract was washed with a saturated aqueous solution of sodium chloride, dried over anhydrous magnesium sulfate, treated with active carbon and then concentrated under reduced pressure to give crude R-isomer. The resolution and purification were duplicated by using strychnine for the crude compound thus obtained, to give 10.9 g of the title compound (R-isomer) having the following physical data.

Next, to mother liquor obtained in the resolution of R-isomer, was added a 20% aqueous solution of ammonia and the precipitated strychnine was filtered off and the filtrate was concentrated under reduced pressure till its volume became about ¼ of the total amount. The residual solution was adjusted to pH 2 with adding conc. hydrochloric acid and extracted with ethyl acetate. The extract was washed with a saturated aqueous solution of sodium chloride, dried over anhydrous magnesium sulfate and concentrated under reduced pressure to give 15 g of dicarboxylic acid being rich in S-isomer. The dicarboxylic acid thus obtained and 19.89 g of D-(-)-threo-1-p-nitrophenyl-2-amino-1,3-propandiol were dissolved in 900 ml of ethanol and crystallized as salt and recrystallized from ethanol. To a suspension of 21 g of the crystals thus obtained in 200 ml of ethyl acetate was added 100 ml of 2N hydrochloric acid and the mixture was separated. The organic layer was washed with water and a saturated aqueous solution of sodium chloride, successively, dried over anhydrous magnesium sulfate and concentrated under reduced pressure to give 7.94 g of the title compound (S-isomer) having the following physical data:

(a) R-isomer

Optical rotation: $[\alpha]_D^{23}$ +20.7° (c=1.8, water).

NMR: δ 10.3~10.0 (2H, m), 3.0~2.3 (3H, m), 1.9~1.2 (4H, m), 0.94 (3H, t).
(b) S-isomer
Optical rotation: [α]$_D^{23}$ −27.2° (c=1.92, water).
NMR: δ 10.3~10.0 (2H, m), 3.0~2.3 (3H, m), 1.9~1.2 (4H, m), 0.94 (3H, t).
IR (KBr method): ν 2900, 2600, 1710, 1680 cm$^{-1}$.
(4) Synthesis of

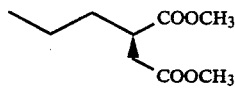

By the same procedure as described in the above (1), the title compound having the following physical data was obtained by using the dicarboxylic acid (R-isomer) prepared in the above (3).
NMR: δ 3.70(3H, s), 3.67(3H, s) 2.93~2.65 (2H, m), 2.50~2.36 (1H, m), 1.70~1.23 (4H, m), 0.91 (3H, t).
(5) Synthesis of

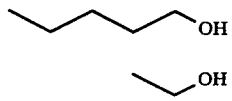

To a suspension of 6.04 g of lithium aluminium hydride in 70 ml of tetrahydrofuran, a solution of 13 g of the dicarboxylic acid ester (prepared in the above (4)) in 70 ml of tetrahydrofuran was added dropwise over 50 minutes, being kept a temperature of the reaction mixture at 55° C. to 60° C., and then the reaction mixture was mildly refluxed for three hours. To the reaction mixture was slowly added dropwise ca. 35 ml of a saturated aqueous solution of sodium sulfate over 1.5 hours, being kept a temperature of the mixture not more than 10° C. and the resulting white precipitates were filtered off. The filtrate was dried over anhydrous magnesium sulfate and concentrated under reduced pressure to give 9.66 g of the crude title compound having the following physical data:
NMR: δ 3.75~3.42 (4H, m), 2.56 (2H, b s), 1.80~1.48 (3H, m), 1.46~1.15 (4H, m), 0.91 (3H, t).
(6) Synthesis of

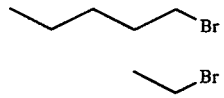

Under an atmosphere of argon, to a suspension of 36.7 g of triphenylphosphine in 120 ml of dry acetonitrile, 7.07 ml of bromine was added dropwise over 15 minutes under cooling with water and the mixture was stirred for 30 minutes at room temperature. Thereto was added dropwise a solution of 9.66 g of the diol compound (prepared in the above (5)) in 15 ml of dry acetonitrile over 10 minutes at a temperature not more than 28° C. and the mixture was stirred for two hours at the same temperature. The reaction mixture was concentrated under reduced pressure and then to the residual solid thus obtained was added 250 ml of n-pentane. The solid was ground enough and dried over anhydrous magnesium sulfate and filtered off. The filtrate was concentrated under reduced pressure to give 17.0 g of the crude title compound having the following physical data:
NMR: δ 3.56~3.35 (4H, m), 2.07~1.81 (3H, m), 1.50~1.20 (4H, m), 0.93 (3H, m).
MS: m/e 256 (M+), 177, 176.
(7) Synthesis of

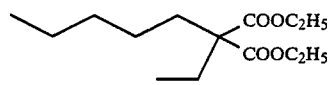

3.22 g of sodium in limited amounts was added to 150 ml of ethanol. After complete dissolution of sodium, 10.9 g of diethyl malonate was added thereto and the mixture was stirred for 20 minutes at 30° C. to 40° C. to give anion of diethyl malonate.
Under an atmosphere of argon, the obtained anion was added dropwise to a solution of 17 g of the dibromo compound (prepared in the above (6)) in 4 ml of ethanol over 30 minutes at 80° C. with stirring and the mixture was stirred for two hours at the same temperature. After cooling to room temperature, the reaction mixture was quenched by adding 30 ml of a saturated aqueous solution of ammonium chloride and concentrated under reduced pressure. To the residue were added ethyl acetate and water and separated. The organic layer was washed with water and a saturated aqueous solution of sodium chloride, successively, dried over anhydrous magnesium sulfate and concentrated under reduced pressure to give 14.6 g of the crude title compound having the following physical data:
NMR: δ 4.16 (4H, q), 2.50~1.54 (7H, m), 1.40~1.15 (10H, m), 1.34 (6H, t), 0.88 (3H, m).
MS: m/e 256(M+), 211, 182, 173.
(8) Synthesis of

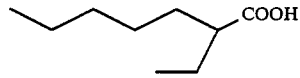

A mixture of 14.6 g of the diester (prepared in the above (7)), 11.5 g of potassium hydroxide, 15 ml of water and 8 ml of ethanol was stirred for two hours at 80° C. and then ethanol was removed under reduced pressure. To the residue was added 90 ml of water and the mixture was extracted with diethyl ether to remove the neutral substance. The aqueous layer was adjusted to pH 2 by adding conc. hydrochloric acid and extracted with diethyl ether. The extract was washed with a saturated aqueous solution of sodium chloride, dried over anhydrous magnesium sulfate and concentrated under reduced pressure to give ca. 10.9 g of dicarboxylic acid as pale yellow solid. The solid thus obtained was subjected to decarboxylation by heating for 30 minutes at 100° C. and then for 30 minutes at 180° C. and the obtained crude compound was distilled under reduced pressure to give 5.9 g of the title compound having the following physical data:
bp: 70° C.-95° C./1 mmHg.
NMR: δ 2.80(1H, m), 0.89(3H, m).
MS: m/e 156(M+), 138, 113, 84.
The title compound thus obtained was identified as a mixture of cis compound and trans compound (about 1:1) by analysis of $^{13}$C-NMR.
(9) Synthesis of

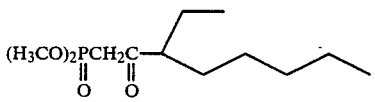

A solution of 3.6 g of the carboxylic acid (prepared in the above (8)) in 20 ml of ethyl acetate was cooled to 0° C. and thereto was added dropwise an ethereal solution of diazomethane until the reaction solution turned to pale yellow and then the reaction mixture was concentrated under reduced pressure to give 3.8 g of the corresponding methyl ester.

Under an atmosphere of argon, a solution of 6.09 g of dimethyl methylphosphonate in 55 ml of tetrahydrofuran was cooled to −78° C. and thereto was added dropwise 31 ml of a 1.5M solution of n-butyllithium in n-hexane and the mixture was stirred for 40 minutes at the same temperature. To the obtained solution was added dropwise a solution of 3.8 g of the methyl ester previously prepared, in 10 ml of tetrahydrofuran at −78° C. and the mixture was stirred for one hour at the same temperature. The reaction mixture was allowed to warm to 0° C. over one hour and then allowed to stand overnight at 4° C. After adding 3 ml of acetic acid, the reaction mixture was diluted with chloroform, washed with water, dried over anhydrous magnesium sulfate and concentrated under reduced pressure. From the residue, excess dimethyl methylphosphonate was removed under reduced pressure (2 mmHg). The residue thus obtained was purified by column chromatography on silica gel (ethyl acetate: n-hexane=1:1→2:1→ethyl acetate) to give 5.08 g of the title compound having the following physical data:

NMR: δ 3.78 (6H, d), 3.11 (2H, d), 0.88 (3H, t).
MS: m/e 262 (M+), 219, 179, 151.

Reference Example 2

Synthesis of

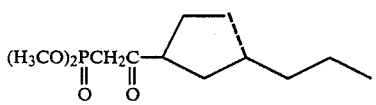

By the same procedures as described in Reference Example 1-(4) to 1-(9), the title compound having the following physical data was obtained by using (S)-2-propylsuccinic acid prepared in Reference Example 1-(3) as a starting material.

NMR: δ 3.78 (6H, d), 3.12 (2H, d), 0.91 (3H, t);
IR: ν 1730, 1700, 1240 cm$^{-1}$;
MS: m/e 262.

Reference Example 3

Synthesis of

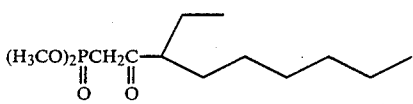

(1) Synthesis of

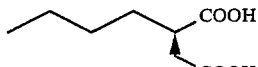

(R-isomer)

and

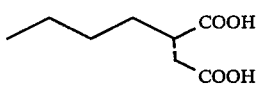

(S-isomer)

By the same procedures as described in Reference Example 1-(1) to 1-(3), the title compound (mixture of R-isomer and S-isomer) was obtained by using 2RS-bromocaproic acid.

801.4 g of the said mixture of R-isomer and S-isomer (solid) and 1.54 kg of (1S, 2S)-(+)-2-amino-1-phenyl-1,3-propandiol were dissolved in 3.3 liters of ethanol to crystallize as salt and the obtained crystals were recrystallized from ethanol. Crystals thus obtained were dissolved in a proper amount of water and the solution was acidified with 6N hydrochloric acid and then extracted with diethyl ether. The extract was dried over anhydrous magnesium sulfate and concentrated under reduced pressure to give 299.9 g of the title compound (R-isomer) having the following physical data.

Next, mother liquor obtained in the resolution of R-isomer was concentrated under reduced pressure and to the residue was added a proper amount of water, and the solution was acidified with 6N hydrochloric acid and then extracted with diethyl ether. The extract was dried over anhydrous magnesium sulfate and concentrated under reduced pressure to give 700 g of the residue being rich in S-isomer. The said residue and 1.7 kg of D-(−)-threo-1-p-nitrophenyl-2-amino-1,3-propandiol were dissolved in 21 liters of ethanol to crystallize as salt and the obtained crystals were recrystallized from ethanol twice. Crystals thus obtained were dissolved in 2.5 liters of water and the solution was acidified with 600 ml of 6N hydrochloric acid and then extracted with diethyl ether. The extract was dried over anhydrous magnesium sulfate and concentrated under reduced pressure to give 286.5 g of the title compound (S-isomer) having the following physical data.

(a) R-isomer
Optical rotation: $[\alpha]_D^{24}$ +19.5° (c=1.61, water).
NMR: δ 3.1~2.3 (3H, m), 2.0~1.1 (6H, m), 0.90 (3H, t).

(b) S-isomer
Optical rotation: $[\alpha]_D^{23}$ −21.1° (c=1.1, water).
NMR: δ 3.1~2.3 (3H, m), 2.0~1.1 (6H, m), 0.90 (3H, t).

(2) Synthesis of

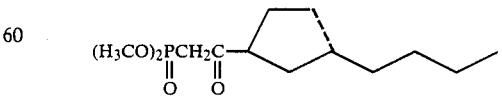

By the same procedures as described in Reference Example 1-(4) to 1-(9), the title compound having the following physical data was obtained by using the dicarboxylic acid (R-isomer) prepared in the above (1).

NMR: δ 3.80 (6H, d), 3.13 (2H, d), 0.86 (3H, t).

IR: ν 3800~3200, 2960, 2925, 2850, 1710, 1460, 1400, 1380, 1360, 1260, 1180, 1050, 1030 cm$^{-1}$.

MS: m/e 276 (M+), 258, 219, 208, 201, 192, 179, 166, 151, 124, 109.

Reference Example 4

Synthesis of

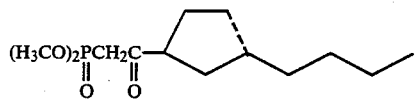

By the same procedures as described in Reference Example 1-(4) to 1-(9), the title compound having the following physical data was obtained by using (S)-2-butylsuccinic acid prepared in Reference Example 3-(1) as starting material.

NMR (CCl$_4$ solution): δ 3.7(6H, d), 3.1(2H, d), 0.88(3H, t).

IR: ν 3650–3200, 2950, 2920, 2850, 1700, 1450, 1250, 1180, 1050, 1020 cm$^{-1}$.

MS: m/e 276 (M+), 258, 247, 245, 235, 234, 219, 209, 179, 151.

Reference Example 5

Synthesis of

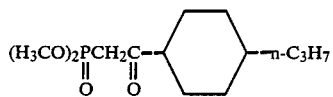

(1) Synthesis of

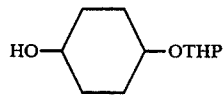

A suspension of 30 g of 1,4-cyclohexanediol (mixture of trans form and cis form) in 2.5 liters of methylene chloride was stirred at 0° C. A catalytic amount of p-toluenesulfonic acid was added thereto and then a solution of 21.7 g of 2,3-dihydropyran in 100 ml of methylene chloride was added thereto over 30 minutes. The mixture was stirred for 15 minutes at 0° C. and then for 30 minutes at room temperature. After addition of 10 drops of triethylamine thereto, the mixture was further stirred for two to three minutes. The reaction mixture was concentrated under reduced pressure and the obtained residue was purified by column chromatography on silica gel (n-hexane: ethyl acetate=2:1→1:1) to give 28 g of the title compound having the following physical data:

NMR: δ 4.75 (1H, m), 4.00~3.83 (1H, m), 3.83~3.66 (2H, m), 3.57~3.42 (1H, m).

(2) Synthesis of

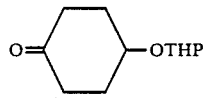

Under an atmosphere of argon, a solution of 46.6 ml of dimethyl sulfoxide in 100 ml of methylene chloride was slowly added dropwise to a solution of 24.4 ml of oxalyl chloride in 2.5 liters of methylene chloride at −78° C. and the mixture was stirred for 20 minutes at the same temperature. To the obtained solution was added dropwise a solution of 28 g of the alcohol compound (prepared in the above (1)) in 70 ml of methylene chloride at a temperature not more than −60° C. and the mixture was stirred for one hour at −78° C. After slowly adding 105 ml of triethylamine, the reaction mixture was stirred for 20 minutes at −78° C. and then allowed to warm to room temperature by removal of refrigerant. In the course of warming, the reaction mixture was vigorously stirred for 30 minutes after addition of 400 ml of water at a temperature in the vicinity of 0° C. The organic layer of the reaction mixture was concentrated under reduced pressure and the aqueous layer thereof was extracted with diethyl ether. The extract and the residue previously obtained by concentrating were combined and the mixture was washed with water and a saturated aqueous solution of sodium chloride, successively, dried over anhydrous magnesium sulfate and concentrated under reduced pressure. The residue was purified by column chromatography on silica gel (n-hexane: ethyl acetate=4:1→1:1) to give 27.4 g of the title compound having the following physical data.

NMR: δ 4.76 (1H, q), 4.15~4.03 (1H, m), 4.00~3.85 (1H, m), 3.63~3.45 (1H, m);

MS: m/e 198 (M+).

(3) Synthesis of

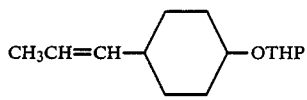

Under an atmosphere of argon, 115 ml of a 1.5M solution of n-butyllithium in n-hexane was added slowly to a solution of 66.6 g of propyltriphenylphosphonium bromide in 500 ml of dry tetrahydrofuran at 0° C. and the mixture was stirred for seven minutes at the same temperature. To the obtained solution was slowly added dropwise a solution of 27.4 g of the ketone compound (prepared in the above (2)) in 50 ml of tetrahydrofuran and the mixture was stirred for 30 minutes at the same temperature and then for 30 minutes at room temperature. After addition of 50 ml of water the reaction mixture was concentrated under reduced pressure. The residue was purified by column chromatography on silica gel (methylene chloride: n-hexane=2:1) to give 24.65 g of the title compound having the following physical data:

NMR: δ 5.10 (1H, t), 4.80~4.65 (1H, m), 4.10~3.62 (2H, m), 3.62~3.30 (1H, m), 0.90 (3H, t);

MS: m/e 224 (M+), 139, 122.

(4) Synthesis of

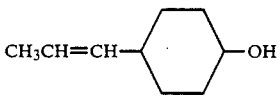

A mixture of 24.6 g of the (tetrahydropyran-2-yloxy) compound (prepared in the above (3)), 0.5 g of p-toluenesulfonic acid monohydrate and 250 ml of methanol was stirred for one hour at room temperature. After addition of several drops of triethylamine thereto, the reaction mixture was concentrated under reduced pressure. The residue was distilled to give 13.9 g of the title compound having the following physical data:
bp: 78° C./4 mmHg.
NMR: δ 5.12 (1H, t), 3.98~3.62 (1H, m), 0.92 (3H, t).
MS: m/e 140 (M+), 122.
(5) Synthesis of

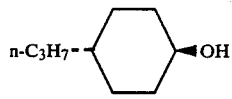

and the corresponding cis form

To a solution of 13.9 g of the olefin compound (prepared in the above (4)) in 140 ml of methanol was added 1.4 g of palladium on carbon (content: 5%) and the mixture was stirred for 14 hours at room temperature under an atmosphere of hydrogen. The reaction mixture was filtered through a layer of celite and the filtrate was concentrated under reduced pressure. The residue was purified by column chromatography on silica gel (n-hexane: ethyl acetate=4:1) to give 8.42 g of the title compound (mixture of cis form and trans form).

8.4 g of the mixture of cis form and trans form was purified by chromatography on a Lobar® column ("Lobar" is a registered Trade Mark of Merck & Co., Inc.) (n-hexane: ethyl acetate=9:1→8.5:1.5) to give 5.55 g of trans form and 1.96 g of cis form, having the following physical data:
(a) trans form
NMR: δ 3.64~3.45 (1H, t t), 2.04~1.88 (2H, m), 1.83~1.65 (2H, m), 1.57 (1H, br), 1.03~0.86 (5H, m+t).
MS: m/e 142 (M+), 124.
(b) cis form
NMR: δ 4.00~3.89 (1H, m), 0.89 (3H, t).
MS: m/e 142 (M+), 124.
(6) Synthesis of

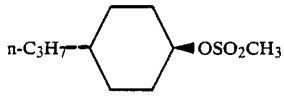

Under an atmosphere of argon, a solution of 5.45 g of the trans-alcohol (prepared in the above (5)) in 50 ml of methylene chloride was allowed to cool to −20° C. and thereto were added 8.50 μl of triethylamine and then 4.44 ml of mesyl chloride. The mixture was stirred for 20 minutes at the same temperature. The reaction mixture was diluted with 200 ml of ethyl acetate, and washed with a saturated aqueous solution of sodium bicarbonate and a saturated aqueous solution of sodium chloride, successively, dried over anhydrous magnesium sulfate and concentrated under reduced pressure. The residue was purified by column chromatography on silica gel (n-hexane: ethyl acetate=4:1) to give 8.78 g of the title compound having the following physical data:
NMR: δ 4.58 (1H, t t), 3.00 (3H, s), 2.20~2.05 (2H, m), 0.88 (3H, t).
MS: m/e 124.
(7) Synthesis of

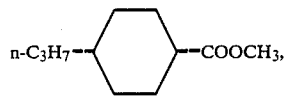

Under an atmosphere of argon, 5.34 g of sodium cyanide was dissolved in 40 ml of dimethyl sulfoxide with heating, and to the solution thus obtained was added a solution of 8.00 g of the mesylate (prepared in the above (6)) in 10 ml of dimethyl sulfoxide at 70° C. to 80° C., and then the mixture was stirred for four hours at 100° C. to 110° C. After cooling to room temperature, the reaction mixture was poured into 250 ml of ice-water and extracted with a mixture of diethyl ether and n-pentane (1:1). The extract was washed with water and a saturated aqueous solution of sodium chloride, successively, and concentrated at atmospheric pressure to give 5.17 g of cis-4-propylcyclohexanecarbonitrile as crude product having the following physical data:
IR (chloroform solution): ν 2225 cm−1.

To 5.17 g of the nitrile previously prepared was added 30 ml of a mixture of water and conc. sulfuric acid (1:1) and the mixture was stirred for three hours at 110° C. to 130° C. After cooling to room temperature, the reaction mixture was poured into 60 ml of water and extracted with ethyl acetate, and then the extract was concentrated under reduced pressure. To the residue was added 30 ml of 1N aqueous solution of sodium hydroxide and the mixture was stirred for five minutes at room temperature. The alkaline aqueous solution was extracted with diethyl ether to remove the neutral substance, and the remaining aqueous solution was adjusted again to pH 3 with 3N hydrochloric acid and extracted with ethyl acetate. The extract was washed with water and a saturated aqueous solution of sodium chloride, successively, dried over anhydrous magnesium sulfate and concentrated under reduced pressure to give 1.91 g of cis-4-propylcyclohexanecarboxylic acid as crude product having the following physical data:
NMR: δ 7.00–5.00(1H, br), 2.56(1H, m), 0.88(3H, t).
IR (chloroform solution): ν −2650, 1690 cm−1.

1.91 g of the carboxylic acid previously prepared was dissolved in 20 ml of diethyl ether and allowed to cool to 0° C. To the solution was added dropwise an ethereal solution of diazomethane until the reaction mixture turned to pale yellow and then the reaction mixture was concentrated under reduced pressure. The residue was purified by column chromatography on silica gel (n-hexane: ethyl acetate=9:1) to give 1.73 g of the title compound having the following physical data:
NMR: δ 3.67(3H, s), 2.65–2.40(1H, m), 0.87(3H, t).
IR (chloroform solution): ν 1720 cm−1.
MS: m/e 184(M+), 153, 152.
(8) Synthesis of

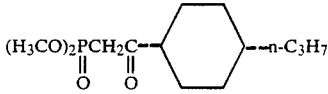

A solution of 1.347 g of dimethyl methylphosphonate in 30 ml of dry tetrahydrofuran was allowed to cool to −78° C. To the solution was added dropwise slowly 7.44 ml of a 1.45M solution of n-butyllithium in n-hexane at a temperature not more than −60° C. and the mixture was stirred for 15 minutes at the same temperature. To the mixture thus obtained was added dropwise slowly a solution of 1.00 g of the ester (prepared in the above (7)) in two ml of dry tetrahydrofuran at a temperature not more than −60° C., and the mixture was stirred for 2.5 hours at −78° C. and adjusted to pH 3 to 4 with acetic acid and then allowed to warm to room temperature. The reaction mixture was diluted with 200 ml of ethyl acetate, washed with a small amount of water, dried over anhydrous magnesium sulfate and concentrated under reduced pressure. The residue was purified by column chromatography on silica gel (ethyl acetate) to give 1.25 g of the title compound having the following physical data:

NMR: δ 3.77 (6H, d), 3.13 (2H, d), 2.75~2.62 (1H, m), 0.86 (3H, t).

MS: m/e 276 (M+), 151, 123.

Reference Example 6

Synthesis of

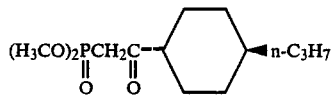

By the same procedures as described in Reference Example 5-(6) to 5-(8), the title compound having the following physical data was obtained by using cis-4-n-propylcyclohexanol prepared in Reference Example 5-(5) as a starting material.

NMR: δ 3.77 (6H, d), 3.13 (2H, d), 2.50 (1H, t t), 0.87 (3H, t).

MS: m/e 276 (M+). 151, 123.

Reference Example 7

Synthesis of

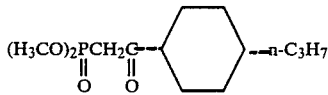

by another processes (1) Synthesis of

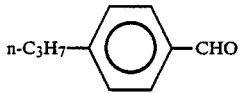

A mixture of 50 g of n-propylbenzene, 58.2 g of hexamethylenetetraamine and 340 ml of trifluoroacetic acid was stirred overnight at 80° C. to 90° C. Trifluoroacetic acid was removed from the reaction mixture under reduced pressure, and the obtained residue was poured into one liter of ice-water and stirred for 30 minutes. Sodium carbonate in limited amounts was added thereto to make it mild alkaline and the mixture was extracted with diethyl ether. The extract was washed with water and a saturated aqueous solution of sodium chloride, successively, dried over anhydrous magnesium sulfate and concentrated under reduced pressure. The residue was distilled under reduced pressure to give 32.7 g of the title compound having the following physical data:

bp: 122° C.-127° C./24 mmHg.

NMR: δ 9.96 (1H, s), 7.8 (2H, d), 7.3 (2H, d), 2.68 (2H, t), 1.7 (2H, m), 0.95 (3H, t).

(2) Synthesis of

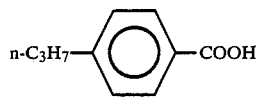

To a solution of 1.2 g of the aldehyde (prepared in the above (1)) in 12 ml of acetone was added dropwise 6 ml of Jones' reagent under cooling with ice and the mixture was stirred for one hour. The reaction mixture was diluted with 50 ml of water and extracted with diethyl ether. The ethereal layer was washed enough with water and then extracted again with a 5% aqueous solution of potassium hydroxide. The aqueous layer was acidified with 6N hydrochloric acid and precipitated crystals were extracted with ethyl acetate. The extract was washed with water and a saturated aqueous solution of sodium chloride, successively, dried over anhydrous sodium sulfate and concentrated under reduced pressure to give 1.2 g of the title compound as crude crystals having the following physical data:

mp: 135° C.-137° C.

IR (KBr method): ν 2950, 2630, 2520, 1680, 1605, 1565, 1418, 1285 cm$^{-1}$.

NMR: δ 8.1 (2H, d), 7.2 (2H, d) 2.68 (2H, t), 1.7 (2H, m), 0.95 (3H, t).

(3) Synthesis of

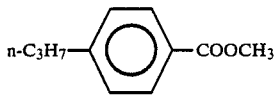

To a solution of 9.4 g of the carboxylic acid (prepared in the above (2)) in 50 ml of methanol was added five ml of conc. sulfuric acid and the mixture was refluxed for four hours. After cooling, the reaction mixture was diluted with water and extracted with ethyl acetate. The extract was washed with water and a saturated aqueous solution of sodium bicarbonate, successively, dried over anhydrous sodium sulfate and concentrated under reduced pressure. The residue was distilled under reduced pressure to give 8.0 g of the title compound having the following physical data: bp: 102° C.-105° C./6mmHg;

NMR: δ 7.95 (2H, d), 7.2 (2H, d), 3.90 (3H, s), 2.65 (2H, t), 1.65 (2H, m), 0.95 (3H, t).

IR: ν 2950, 1720, 1607, 1430, 1275, 1105 cm$^{-1}$.

(4) Synthesis of

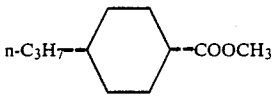

and the corresponding trans form

To a solution of 5.6 g of the methyl benzoate compound (prepared in the above (3)) in 75 ml of n-hexane were added 50 ml of phosphate buffer solution (pH 7.6), 850 mg of tetra-n-butylammonium bisulfate ([CH$_3$(CH$_2$)$_3$]$_4$NHSO$_4$) and 280 mg of the dimer of chloro (1,5-hexadiene) rhodium ([RhCl(CH$_2$=CH—CH$_2$—CH$_2$—CH=CH$_2$)]$_2$, prepared as described hereinafter), successively with vigorous stirring to dissolve completely.

The mixture thus obtained was reacted for 7 to 8 hours at room temperature at 10 to 50 atmospheric pressure of hydrogen in autoclave and the reaction mixture was extracted with ethyl acetate. The extract was washed with water and a saturated aqueous solution of sodium chloride, successively, dried over anhydrous magnesium sulfate and concentrated under reduced pressure to give 5.63 g of the title compound (mixture of cis form and trans form).

The obtained mixture was purified by column chromatography on a Kiesel ® gel 60 ("Kiesel" is a registered Trade Mark of Merck & Co., Inc.) (n-hexane: ethyl acetate=40:1) to give 3.53 g of the title compound (cis form) and 0.95 g of the corresponding trans form, having the following physical data, and 1.03 g of mixture thereof.

(a) cis form
NMR: δ 3.67(3H, s), 2.65–2.40(1H, m), 0.87(3H, t).
IR (chloroform solution): ν 1720 cm$^{-1}$.
MS: m/e 184(M+), 153, 152.

(b) trans form
NMR: δ 3.65(3H, s), 2.23(1H, tt), 0.87(3H, t).
IR (chloroform solution): ν 1720 cm$^{-1}$.
MS: m/e 184(M+), 153, 152.

The dimer of chloro (1,5-hexadiene) rhodium, used in the above procedure, was prepared as follows:

Under an atmosphere of argon, to a mixture of one g of rhodium trichloride trihydrate and 410 mg of sodium carbonate, were added 10 ml of a mixture of ethanol and water (5:1) (both being degassed), and 1.5 ml of 1,5-hexadiene, successively, at room temperature with stirring and then the mixture was stirred for 24 hours at 40° C. under heating with oil bath. After cooling the reaction mixture with ice-water, it was filtered. Crystals thus obtained were washed with n-pentane and a mixture of water and methanol (5:1), successively and dried in vacuo to give 665 mg of the dimer of chloro (1,5-hexadiene) rhodium as brown crystals.

(5) Synthesis of

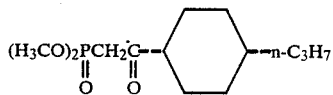

By the same procedure as described in Reference Example 5(8), the title compound having the same physical data as those of the product prepared in Reference Example 5 was obtained by using the ester (cis form) prepared in the above (4).

Reference Example 8

Synthesis of

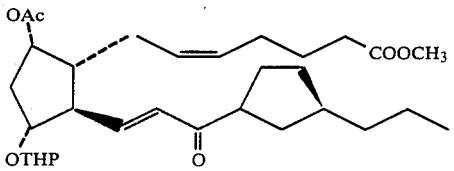

Under an atmosphere of argon, a solution of 5.8 g of the phosphonate (prepared in Reference Example 1) in 15 ml of tetrahydrofuran was added dropwise to a suspension of 765 mg of sodium hydride (content: 63%) in 150 ml of tetrahydrofuran under cooling with water, and the mixture was stirred for 20 minutes at room temperature. Thereto was added dropwise a solution of 7.92 g of 1α-acetoxy-2α-(6-methoxycarbonylhex-cis-2-enyl)-3β-formyl-4α-(tetrahydropyran-2-yloxy)cyclopentane (prepared as described in the specification of the British Patent No. 1,482,928) in 20 ml of tetrahydrofuran at room temperature and the mixture was stirred for 20 minutes at the same temperature. To the reaction mixture was added 50 ml of a saturated aqueous solution of ammonium chloride and the mixture was extracted with ethyl acetate. The extract was washed with water and a saturated aqueous solution of sodium chloride, successively, dried over anhydrous magnesium sulfate and concentrated under reduced pressure. The residue was purified by column chromatography on silica gel (ethyl acetate: n-hexane=1:6→1:4) to give 8.65 g of the title compound having the following physical data:
TLC (ethyl acetate: n-hexane=1:1): Rf=0.55.
NMR: δ 6.9~6.4 (1H, m), 6.1 (1H, d d), 5.5~5.2 (2H, m), 5.2~4.9 (1H, m), 3.6 (3H, s), 2.0 (3H, s), 0.85 (3H, m).
IR: ν 1735, 1690, 1665, 1620 cm$^{-1}$.

Reference Example 9

Synthesis of

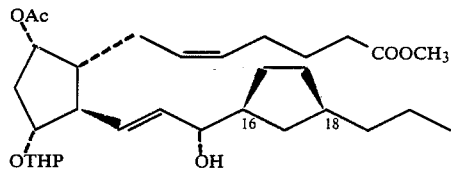

and

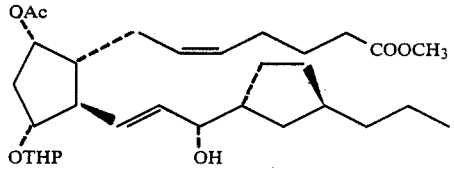

Under an atmosphere of argon, a mixture of 5 ml of ethanol and 35 ml of dry tetrahydrofuran was added dropwise to a suspension of 3.95 g of lithium aluminium hydride in 190 ml of dry tetrahydrofuran over 10 minutes under cooling with water and the mixture was stirred for 10 minutes at the same temperature. To the solution thus obtained was added dropwise a solution of 24.5 g of S-2,2'-dihydroxy-1,1'-binaphthyl (SBN) in 93 ml of dry tetrahydrofuran over 25 minutes and the mixture was stirred for 20 minutes. After cooling the reaction mixture to −78° C., a solution of 7.59 g of the 15-oxo compound (prepared in Reference Example 8) in 50 ml of dry tetrahydrofuran was added dropwise thereto over 10 minutes and the mixture was stirred for two hours at −78° C. To the reaction mixture was added dropwise slowly 10 ml of methanol at −78° C. and the reaction mixture was allowed to warm gradually. In the course of warming, 100 ml of 1N hydrochloric acid was added thereto at a temperature in the vicinity of −40° C. and the reaction mixture was stirred for 20 minutes at 0° C. and allowed to warm finally to room temperature. To the reaction mixture were added 35 g of celite and 300 ml of ethyl acetate and the mixture was filtered. The filtrate was washed with water and a saturated aqueous solution of sodium chloride, successively, dried over anhydrous magnesium sulfate and concentrated under reduced pressure. In the course of concentrting, precipitated SBN was ground enough after adding benzene, and was filtered off and the filtrate was concentrated under reduced pressure again. The residue was purified by column chromatography on silica gel (methylene chloride→methylene chloride: ethyl acetate=10:1→5:1→ethyl acetate: cyclohexane=1:4→1:2→1:1) to give 6.45 g of the title compound (mixture of (16S, 18 R) isomer and (16R, 18R) isomer) having the following physical data.

4 g of the mixture was purified by column chromatography on a Kiesel ® gel 60 ("Kiesel" is a registered Trade Mark of Merck & Co., Inc.) (ethyl acetate: cyclohexane=1:4→1:2→1:1) to give 1.094 g of (16S, 18R) isomer and 0.636 g of (16R, 18R) isomer, having the following physical data:

(a) (16S, 18R) isomer

TLC (methylene chloride: ethyl acetate=4:1): Rf=0.29.

NMR: δ 5.75~5.5 (2H, m), 5.5~5.2 (2H, m), 5.15~5.0 (1H, m), 3.67 (3H, s), 2.05 (3H, s), 0.88 (3H, m).

(b) (16R, 18R) isomer

TLC (methylene chloride: ethyl acetate=4:1): Rf=0.26.

NMR: δ 5.75~5.45 (2H, m), 5.45~5.2 (2H, m), 5.15~5.0 (1H, m), 3.66 (3H, s), 0.87 (3H, m).

Reference Example 10

Synthesis of

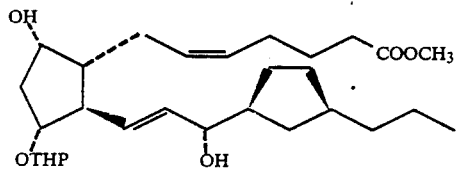

Under an atmosphere of argon, a mixture of 2.0 g of the 9-acetoxy compound ((16S, 18R) isomer prepared in Reference Example 9), 552 mg of potassium carbonate and 20 ml of methanol was stirred for two hours at room temperature, and further for two hours at 40° C. After cooling to room temperature, the reaction mixture was poured into 100 ml of cold 0.1N hydrochloric acid and extracted with ethyl acetate. The extract was washed with water and a saturated aqueous solution of sodium chloride, successively, dried over anhydrous magnesium sulfate and concentrated under reduced pressure to give 1.88 g of the crude title compound having the following physical data:

TLC (ethyl acetate: n-hexane=1:1): Rf=0.29 and 0.27.

EXAMPLE 1

Synthesis of

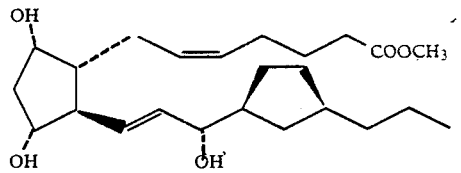

A mixture of 1.88 g of the 11-(tetrahydropyran-2-yloxy) compound (prepared in Reference Example 10), 20 mg of p-toluenesulfonic acid monohydrate and 25 ml of methanol was stirred for 1.5 hours at room temperature. After adding one ml of triethylamine, the reaction mixture was concentrated under reduced pressure. The residue was purified by column chromatography on silica gel (ethyl acetate: n-hexane=1:2→1:1→2:1→ethyl acetate) to give 1.25 g of the title compound having the following physical data:

Optical rotation: $[\alpha]_D^{27}$ +36.8° (c=1.03, chloroform).

NMR: δ 5.65~5.30 (4H, m), 4.15 (1H, m), 4.00~3.89 (2H, m), 3.66 (3H, s), 0.87 (3H, m).

IR: ν 3400, 1735, 1435, 1240, 1200, 1165, 1080, 1050, 1020, 970 cm$^{-1}$:

MS: m/e 408 (M$^+$), 390, 372, 318, 297, 279, 261, 250.

Reference Example 11

Synthesis of

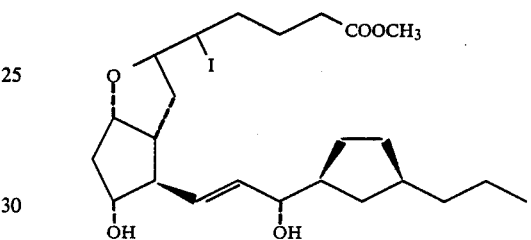

To a solution of 1.24 g of the PGF$_{2\alpha}$ compound (prepared in Example 1) in 80 ml of methylene chloride was added 80 ml of a saturated aqueous solution of sodium bicarbonate, and the mixture was stirred enough under cooling with ice. To the obtained solution was added dropwise a solution of 890 mg of iodine in 45 ml of methylene chloride over two hours at 3° C. to 4° C., and the mixture was stirred for one hour at the same temperature. The reaction mixture was quenched by adding a 20% aqueous solution of sodium thiosulfate to remove excess iodine, and diluted with diethyl ether. The obtained organic layer was washed with water and a saturated aqueous solution of sodium chloride, successively, dried over anhydrous magnesium sulfate and concentrated under reduced pressure to give ca. 1.7 g of the crude title compound having the following physical data:

TLC (ethyl acetate: n-hexane=3:1): Rf=0.35.

Reference Example 12

Synthesis of

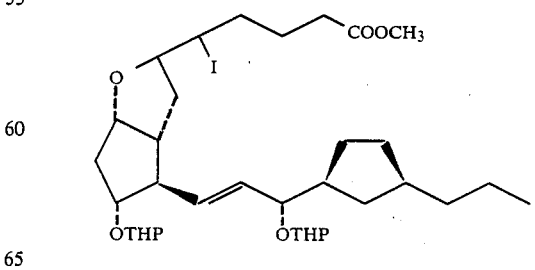

A mixture of ca. 1.7 g of the 11,15-dihydroxy compound (prepared in Reference Example 11), 0.64 ml of 2,3-dihydropyran, a catalytic amount of p-toluenesulfonic acid monohydrate and 20 ml of methylene chloride was stirred for 30 minutes at room temperature. After adding a saturated aqueous solution of sodium bicarbonate, the reaction mixture was diluted with ethyl acetate. The organic layer was washed with water and a saturated aqueous solution of sodium chloride, successively, dried over anhydrous magnesium sulfate and concentrated under reduced pressure to give 2.27 g of the crude title compound having the following physical data:

TLC (ethyl acetate: n-hexane=1:1): Rf=0.64.

Reference Example 13

Synthesis of

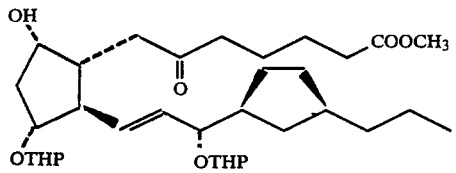

A mixture of ca. 2.27 g of the iodoether (prepared in Reference Example 12), 3.14 ml of 1,5-diazabicyclo[5.4.0]undec-5ene (DBU) and 20 ml of toluene was stirred for 16 hours at 40° C. After cooling to room temperature, the reaction mixture was diluted with 200 ml of ethyl acetate and washed with water. To the solution was added 50 ml of 1N hydrochloric acid and the mixture was shaken enough. The organic layer was washed with water and a saturated aqueous solution of sodium chloride, successively, dried over anhydrous magnesium sulfate and concentrated under reduced pressure. The residue was purified by column chromatography on silica gel (ethyl acetate: n-hexane=1:2→1:1→2:1) to give 1.6 g of the title compound having the following physical data:

TLC (ethyl acetate: n-hexane=1:1): Rf=0.31.
NMR: δ 5.36 (2H, m), 4.63 (2H, m), 3.66 (3H, s), 0.87 (3H, m).
IR: ν 3470, 2950, 2880, 1740, 980 cm$^{-1}$.

Reference Example 14

Synthesis of

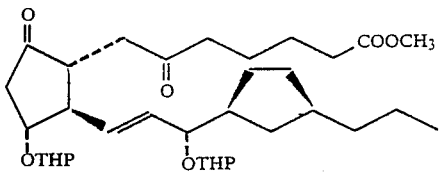

To a solution of 1.6 g of the 9-hydroxy compound (prepared in Reference Example 13) in 27 ml of acetone was added dropwise 2.6 ml of Jones' reagent (obtained from 9.7 g of chromium trioxide, 8 ml of conc. sulfuric acid and water to make up to 35 ml in total volume) over 20 minutes at −16° C. to −20° C. and the mixture was stirred for 40 minutes at the same temperature. After adding 0.7 ml of isopropyl alcohol, the reaction mixture was stirred for 20 minutes and then poured into an ice-cooled mixture of 200 ml of diethyl ether and 70 ml of water with vigorous stirring. The organic layer was washed with water and a saturated aqueous solution of sodium chloride, successively, dried over anhydrous magnesium sulfate and concentrated under reduced pressure. The residue was purified by column chromatography on silica gel (ethyl acetate: n-hexane=1:3→1:2→1:1) to give 1.36 g of the title compound having the following physical data:

TLC (ethyl acetate: n-hexane=1:1): Rf=0.46.
IR: ν 2940, 2870, 1740, 1720, 970 cm$^{-1}$.

EXAMPLE 2

Synthesis of

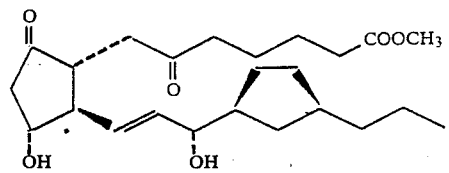

A mixture of 1.36 g of the 11,15-bis(tetrahydropyran-2-yloxy) compound (prepared in Reference Example 14), 20 ml of 65% aqueous acetic acid and 2 ml of tetrahydrofuran was stirred for 3.5 hours at 40° C. and the reaction mixture was diluted with 150 ml of ethyl acetate. After 80 ml of water was added thereto, the reaction solution was neutralized by carefully adding 35 g of sodium bicarbonate powder in limited amounts with vigorous stirring under cooling with ice. The organic layer was washed with an aqueous solution of sodium bicarbonate, water and a saturated aqueous solution of sodium chloride, successively, dried over anhydrous magnesium sulfate and concentrated under reduced pressure. The residue was purified by column chromatography on silica gel (ethyl acetate: n-hexane=1:2→1:1→3:1→ethyl acetate) to give 770 mg of white solid. The obtained solid was recrystallized from 6.5 ml of a mixture of ethyl acetate and n-hexane (4:9) to give 680 mg of the title compound as white powder, having the following physical data:

Optical rotation: [α]$_D^{23}$ −61.4° (c=1.0, chloroform).
mp: 85° C.-86.5° C.
NMR: δ 5.73~5.48 (2H, m), 4.12 (1H, m), 3.88 (1H, m), 3.67 (3H, s), 0.88 (3H, m).
IR (KBr method): ν 3470, 1745, 1725, 1705, 1455, 1430, 1400, 1375, 1355, 1300, 1250, 1195, 1160, 1100, 1080, 1020, 995, 970 cm$^{-1}$.
MS: m/e 404, 386, 373, 311, 293, 261, 243, 215, 213, 143, 115, 111, 69, 55.

Reference Example 15

Synthesis of

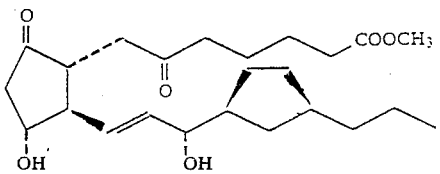

By the same procedures as described in Reference Example 10, Example 1, Reference Example 11 to 14 and Example 2, the title compound having the following physical data was obtained by using (16R, 18R) isomer prepared in Reference Example 9.

Optical rotation: [α]$_D^{20}$ −68.8° (c=0.75, chloroform).
NMR: δ 5.64 (1H, d d), 5.55 (1H, d d), 4.2~4.0 (1H, m), 3.88 (1H, d d), 3.66 (3H, s).

IR (KBr method): ν 3450, 2950, 2930, 2850, 1740, 1720, 1710 (shoulder) cm⁻¹.
MS: m/e 404, 386, 373, 355.

Reference Example 16

Synthesis of

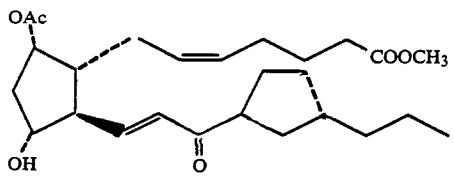

By the same procedures as described in Reference Example 8 and Example 1, the title compound having the following physical data was obtained by using the phosphonate prepared in Reference Example 2 and 1α-acetoxy-2α-(6-methoxycarbonylhex-cis-2-enyl)-3β-formyl-4α-(tetrahydropyran-2-yloxy)cyclopentane.

NMR: δ 6.69 (1H, d d), 6.28 (1H, d), 5.34 (2H, m), 5.15 (1H, m), 4.09 (1H, m), 3.67 (3H, s), 3.12 (1H, m), 4.56 (2H, m), 2.3 (2H, t), 2.09 (3H, s), 0.89 (3H, m).
IR: ν 3470, 1738, 1690, 1765, 1626, 1247 cm⁻¹.
MS: m/e 448 (M+), 430, 388, 370.

Reference Example 17

Synthesis of

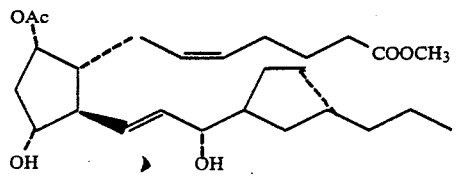

To a solution of 6.57 g of 2,6-di-tert-butyl-4-methylphenol in 62 ml of toluene was added dropwise 12.7 ml of a 1.75M solution of diisobutylaluminium hydride in toluene at 0° C. and the mixture was stirred for one hour at the same temperature. After cooling to −78° C., thereto was added dropwise a solution of ca. 900 mg of the 15-oxo compound (prepared in Reference Example 16) in 7 ml of toluene and the mixture was allowed to warm gradually to 5° C. with stirring. The reaction mixture was stirred vigorously at room temperature after adding 7.6 ml of water and then diluted with 120 ml of ethyl acetate. The obtained solution was filtered through a layer of celite and the filtrate was concentrated under reduced pressure. The residue was purified by column chromatography on silica gel (ethyl acetate: n-hexane=1:2→2:1→4:1) to give 0.42 g of the title compound having the following physical data and 0.21 g of the corresponding 15β-isomer.

NMR: δ 5.64 (1H, d d d), 5.46 (1H, d d), 5.33 (2H, m), 5.11 (1H, m), 3.9 (2H, m), 3.66 (3H, s), 2.51 (1H, m), 2.29 (2H, t), 2.07 (3H, s), 0.88 (3H, m).
IR: ν 3400, 1737, 1720 (shoulder), 1245, 970 cm⁻¹.
MS: m/e 450 (M+), 372, 354, 339, 321.

Reference Example 18

Synthesis of

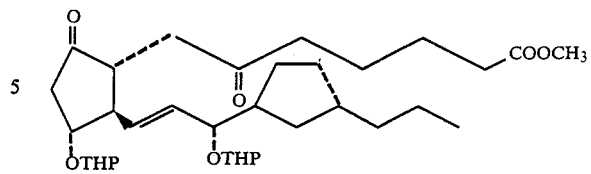

By the same procedures as described in Reference Example 10 to 14, the title compound having the following physical data was obtained by using the 9-acetoxy-PGF$_{2\alpha}$ compound prepared in Reference Example 17.

NMR: δ 5.7–5.25(2H, m), 4.8–4.55(2H, m), 4.3–3.9(1H, m), 3.83 (3H, m), 3.67 (3H, s), 3.5 (2H, m), 0.89 (3H, m).
IR: ν 1743, 1716, 972 cm⁻¹.
MS: m/e 488, 475, 457, 404, 386.

EXAMPLE 3

Synthesis of

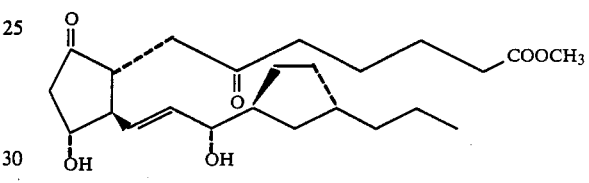

and

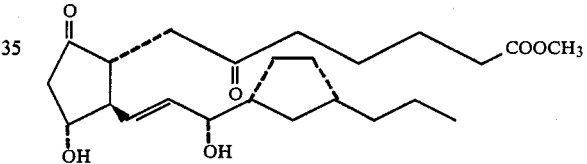

By the same procedure as described in Example 2, the title compound (mixture of (16S, 18S) isomer and (16R, 18S) isomer) was obtained by using the 11,15-bis(tetrahydropyran-2-yloxy) compound prepared in Reference Example 18.

The obtained mixture was purified by chromatography on a Lobar ® column (n-hexane: ethyl acetate=1:5→ethyl acetate) to give (16S, 18S) isomer (less polar) and (16R, 18S) isomer (more polar), both having the following physical data.

(a) (16S, 18S) isomer
NMR: δ 5.6 (2H, m), 4.13 (1H, m), 3.86 (1H, d d), 3.67 (3H, s), 2.8 (1H, d d), 2.68 (1H, b d), 2.02 (1H, m), 0.89 (3H, m).
IR (KBr method): ν 3470, 3400 (shoulder), 1745, 1727, 1710 (shoulder), 970 cm⁻¹.
MS: m/e 404, 386, 293, 261, 243, 215.

(b) (16R, 18S) isomer
NMR: δ 5.63 (2H, m), 4.15 (1H, m), 3.91 (1H, d d), 3.67 (3H, s), 2.8 (1H, d d), 2.68 (1H, m), 2.0 (1H, m), 0.89 (3H, m).
IR (KBr method): ν 3500, 3380, 1744, 1728, 1717 (shoulder) 975 cm⁻¹.
MS: m/e 404, 386, 293, 261, 243, 215.

Reference Example 19

Synthesis of

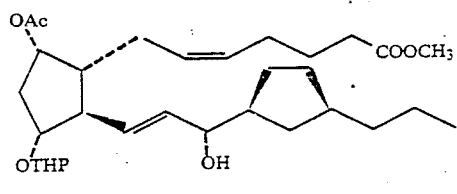

and

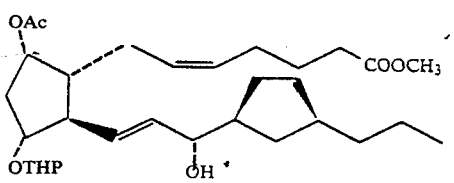

By the same procedures as described in Reference Example 8 and 9, the title compounds, i.e. (16S, 18R) isomer (less polar) and (16R, 18R) isomer (more polar), having the following physical data, were obtained by using the phosphonate prepared in Reference Example 3 and 1α-acetoxy-2α-(6-methoxycarbonylhex-cis-2-enyl)-3β-formyl-4α-(tetrahydropyran-2-yloxy)cyclopentane.

(a) (16S, 18R) isomer

NMR: δ 5.6(2H, m), 5.35(2H, m), 5.06(1H, m), 4.66 and 4.58 (1H, m), 3.9 (3H, m), 3.66 (3H, s), 3.44 (1H, m), 2.5 (1H, m), 2.29 (2H, t), 2.05 (3H, s), 0.88 (3H, m).

IR: ν 3480, 1735, 972 cm⁻¹.

MS: m/e 530, 517, 446, 428, 386, 368.

(b) (16R, 18R) isomer

NMR: δ 5.6(2H, m), 5.34(2H, m), 5.06(1H, m), 4.66 and 4.58 (1H, m), 3.9 (3H, m), 3.66 (3H, s), 3.45 (1H, m), 2.5 (1H, m), 2.29 (3H, t), 2.05 (3H, s), 0.87 (3H, m).

IR: ν 3480, 1734, 970 cm⁻¹.

MS: m/e 530, 517, 464, 446, 386, 368, 356.

Reference Example 20

Synthesis of

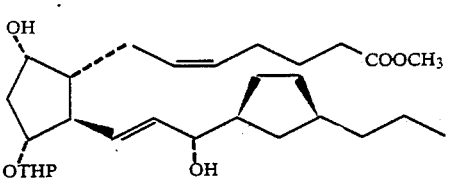

By the same procedure as described in Reference Example 10, the title compound having the following physical data was obtained by using the 9-acetoxy compound ((16S, 18R) isomer) prepared in Reference Example 19.

NMR: δ 5.56 (1H, m), 5.41 (1H, m), 4.67 (1H, m), 4.1 (2H, m), 3.86 (2H, m), 3.66 (3H, s), 3.46 (1H, m), 2.31 (2H, t), 0.87 (3H, m).

IR: ν 3470, 1736, 973 cm⁻¹.

MS: m/e 506 (M⁺), 488, 475, 470, 457, 422, 404, 386, 368, 360, 356, 322, 264.

Reference Example 21

Synthesis of

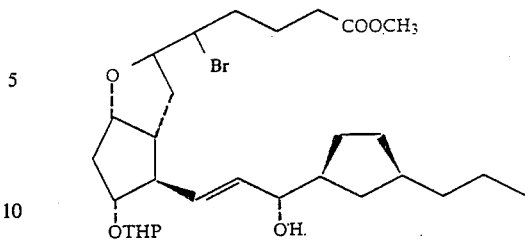

To a solution of 1.17 g of the 9-hydroxy compound (prepared in Reference Example 20) in a mixture of 17.7 ml of chloroform and 2.3 ml of tetrahydrofuran was added all at once 0.56 g of N-bromosuccinimide at room temperature and the mixture was stirred for one hour at the same temperature. The reaction mixture was diluted with diethyl ether, and the ethereal solution thus obtained was washed with a saturated aqueous solution of sodium bicarbonate and a saturated aqueous solution of sodium chloride, successively, dried over anhydrous magnesium sulfate and concentrated under reduced pressure to give 1.65 g of the crude title compound having the following physical data:

NMR: δ 5.6 (2H, m), 4.65 (1H, m), 4.54 (1H, m), 4.17 (1H, m), 4.05~3.6 (4H, m), 3.67 (3H, s), 3.46 (1H, m), 0.87 (3H, m).

Reference Example 22

Synthesis of

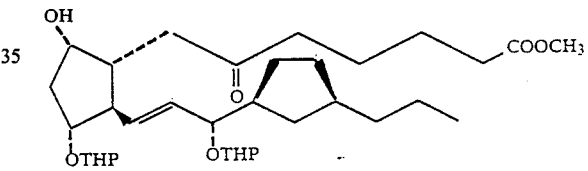

By the same procedures as described in Reference Example 12 and 13, the title compound having the following physical data was obtained by using the bromo ether prepared in Reference Example 21.

NMR: δ 5.6~5.2 (2H, m), 4.65 (2H, m), 4.19 (1H, m), 3.66 (3H, s×2), 3.46 (2H, m), 0.88 (3H, m).

IR: ν 3460, 1738, 980 cm⁻¹.

MS: m/e 588, 557, 503, 488, 486, 420, 403, 384.

Reference Example 23

Synthesis of

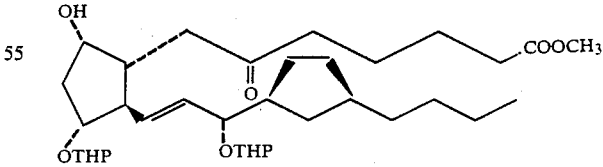

A mixture of 0.213 g of the ester (prepared in Reference Example 22), 0.7 ml of 1N aqueous solution of sodium hydroxide and 3 ml of methanol was stirred overnight at room temperature. After water was added to the reaction mixture, methanol was removed from it under reduced pressure. After adding diethyl ether to the residual solution, one ml of 1N hydrochloric acid was added to the ethereal solution with vigorous stirring and then the ethereal layer was separated. The organic layer was washed with a saturated aqueous solution of sodium chloride, dried over anhydrous magnesium sulfate and concentrated under reduced pressure to give 0.21 g of the crude title compound having the following physical data:

IR: ν 3600–2500, 1732 (shoulder), 1710, 980 cm⁻¹.
MS: m/e 574, 490, 474, 472, 406, 388, 370.

Reference Example 24

Synthesis of

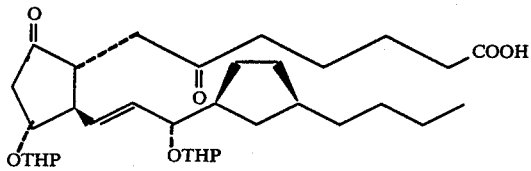

By the same procedure as described in Reference Example 14, the title compound having the following physical data was obtained by using the 9-hydroxy compound prepared in Reference Example 23.

NMR: δ 5.60 (1H, m), 5.51 (1H, m), 4.7 (2H, m), 0.88 (3H, m).
IR: ν 3600~2400, 1743, 1713, 975 cm⁻¹.
MS: m/e 488, 420, 404, 386, 279.

EXAMPLE 4

Synthesis of

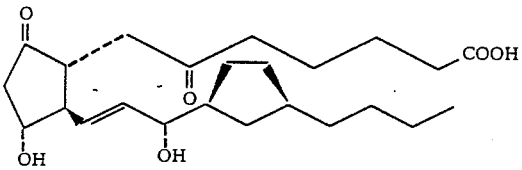

By the same procedure as described in Example 2, the title compound having the following physical data was obtained by using the 11,15-bis(2-tetrahydropyran-2-yloxy) compound prepared in Reference Example 24.

mp: 99° C. –102° C.
NMR: δ 5.57(2H, m), 4.09(1H, m), 3.85(1H, m), 2.78(1H, dd), 0.88(3H, m).
IR (KBr method): ν 3600–2400, 1748, 1728, 1708, 973 cm⁻¹.
MS: m/e 404, 386, 279.

EXAMPLE 5

Synthesis of

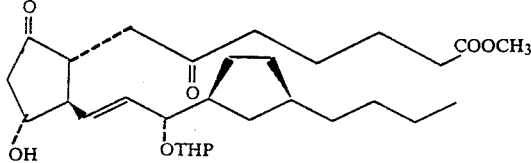

To a solution of 9.9 mg of the carboxylic acid (prepared in Example 4) in one ml of methanol was added dropwise an ethereal solution of diazomethane under cooling with ice till the reaction solution turned to pale yellow, and then the reaction mixture was concentrated under reduced pressure to give 11 mg of the title compound having the following physical data:

mp: 80° C.–82° C.
NMR: δ 5.6 (2H, m), 4.11 (1H, m), 3.86 (1H, m), 3.66 (3H, s), 2.78 (1H, d d), 0.87 (3H, m).
IR (KBr method): ν 3450, 1744, 1725, 1707, 972 cm⁻¹.
MS: m/e 418, 400, 311, 293.

Reference Example 25

Synthesis of

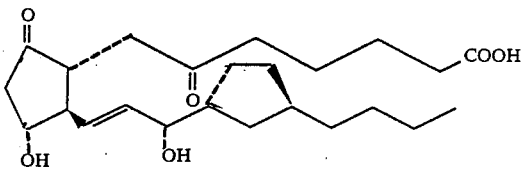

By the same procedures as described in Reference Example 20 to 24 and Example 4, the title compound having the following physical data was obtained by using (16R, 18R) isomer prepared in Reference Example 19.

mp: 118° C.–121° C.
NMR: δ 5.58 (2H, m), 4.09 (1H, m), 3.86 (1H, m), 2.78 (1H, d d), 2.70 (2H, m), 0.88 (3H, m).
IR (KBr method): ν 3600–2400, 1739, 1707, 972 cm⁻¹.
MS: m/e 404, 386, 279.

Reference Example 26

Synthesis of

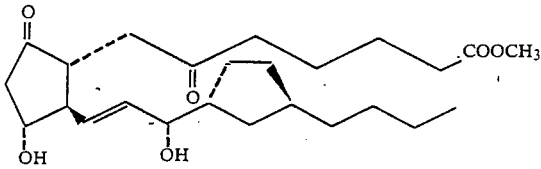

By the same procedure as described in Example 5, the title compound having the following physical data was obtained by using the carboxylic acid prepared in Reference Example 25.

mp: 92° C.–96° C.
NMR: δ 5.6 (2H, m), 4.12 (1H, m), 3.89 (1H, m), 3.66 (3H, s), 2.78 (1H, d d), 0.88 (3H, m).
IR (KBr method): ν 3440, 1741, 1725, 1716 (shoulder), 974 cm⁻¹.
MS: m/e 418, 400, 311, 293.

Reference Example 27

Synthesis of

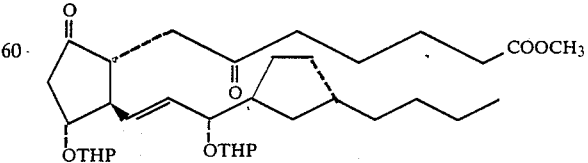

By the same procedures as described in Reference Example 8, 17 and 10 to 14, the title compound having the following physical data was obtained by using the phosphonate prepared in Reference Example 4 and 1α-acetoxy-2α-(6-methoxycarbonylhex-cis-2-enyl)-3α-formyl-4α-(tetrahydropyran-2-yloxy)cyclopentane.

IR: ν 2950, 2860, 1740, 1720, 1460, 1450, 1440, 1270, 1260, 1250, 1240, 1200, 1130, 1080, 1030, 1020 cm$^{-1}$.

MS: m/e 519, 502, 489, 471, 432, 418, 400.

EXAMPLE 6

Synthesis of

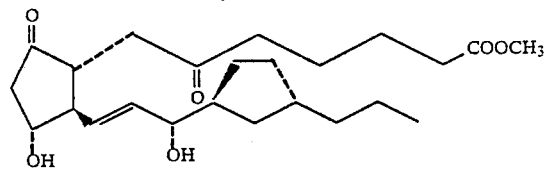

and

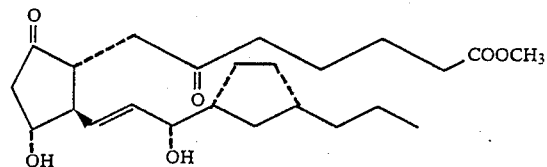

By the same procedure as described in Example 2, the title compound (mixture of (16S, 18S) isomer) was obtained by using the 11,15-bis(tetrahydropyran-2-yloxy) compound prepared in Reference Example 27.

The obtained mixture was purified by chromatography on a Lobar ® column (cyclohexane: ethyl acetate=1:2→1:3→ethyl acetate) to give (16S, 18S) isomer (less polar) and (16R, 18S) isomer (more polar), having the following physical data: (a) (16S, 18S) isomer mp: 67°–68° C.

NMR: δ 5.58 (2H, m), 4.1 (1H, m), 3.85 (1H, m), 3.66 (3H, s), 2.0 (1H, m), 0.88 (3H, t).

IR (KBr method): ν 3650–3200, 2950, 2860, 1640, 1630, 1610, 1460, 1440, 1380, 1360, 1260, 1180, 1080 cm$^{-1}$.

MS: m/e 418, 400, 387, 369, 311, 293, 261, 257, 243.

(b) (16R, 18S) isomer mp: 73° C.–74.5° C.;

NMR: δ 5.6 (2H, m), 4.1 (1H, m), 3.85 (1H, m), 3.66 (3H, s), 2.0 (1H, m), 0.88 (3H, t).

IR (KBr method): ν 3650–3200, 1640, 1630, 1610, 1460, 1440, 1410, 1400, 1380, 1350, 1250, 1200, 1170 cm$^{-1}$.

MS: m/e 418, 400, 387, 369, 311, 293, 261, 257, 243.

Reference Example 28

Synthesis of

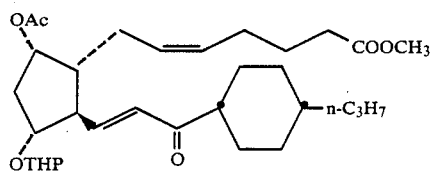

To a suspension of 0.152 g of sodium hydride (content: 64%) in 10 ml of dry tetrahydrofuran was added dropwise slowly a solution of 1.25 g of the phosphonate (prepared in Reference Example 5) in 5 ml of dry tetrahydrofuran under cooling with water and the mixture was stirred for 15 minutes at room temperature. Thereto was added all at once a solution of 1.55 g of 1α-acetoxy-2α-(6-methoxycarbonylhex-cis-2-enyl)-3β-formyl-4α-(tetrahydropyran-2-yloxy)cyclopentane (prepared as described in the specification of the British Patent No. 1482928) in 6 ml of dry tetrahydrofuran at room temperature and the mixture was stirred for one hour at room temperature. The reaction mixture was adjusted to pH 3 by adding acetic acid, and then filtered through a layer of celite. The filtrate was concentrated under reduced pressure (acetic acid was removed by concentrating with the addition of toluene). The residue was purified by column chromatography on silica gel (n-hexane=ethyl acetate=4:1) to give 1.79 g of the title compound having the following physical data:

NMR: δ 6.83~6.66 (1H, d d×2), 6.40 ~6.29 (1H, d×2), 5.45~5.22 (2H, m), 5.15~5.04 (1H, m), 4.61~4.48 (1H, m), 4.17~3.91 (1H, m), 3.67 (3H, s), 3.91~3.67 (3H, m), 3.53~3.32 (2H, m), 2.29 (2H, t), 1.05~0.91 (3H, t).

IR (chloroform solution): ν 2910, 2850, 1720, 1680, 1650, 1610, 1430, 1370, 1240, 1010, 960 cm$^{-1}$.

MS: m/e 546 (M+), 515, 462.

Reference Example 29

Synthesis of

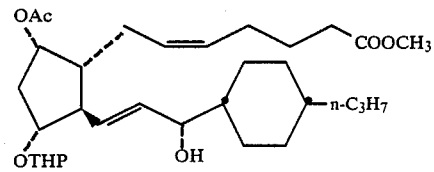

Under an atmosphere of argon, to a suspension of 0.915 g of lithium aluminium hydride in 44 ml of dry tetrahydrofuran were added dropwise slowly a mixture of 1.13 ml of ethanol and 8 ml of dry tetrahydrofuran at 5° C. and then added dropwise slowly a solution of 5.57 g of S-2,2'-dihydroxy-1,1'-binaphthyl (SBN) in 20 ml of dry tetrahydrofuran. The mixture thus obtained was stirred for 15 minutes at room temperature, and then allowed to cool to −78° C. Thereto was added dropwise slowly a solution of 1.78 g of the 15-oxo compound (prepared in Reference Example 28) in 9 ml of dry tetrahydrofuran and the mixture was stirred for 15 minutes at the same temperature. After adding carefully 20 ml of methanol to reaction mixture at −78° C., it was allowed to warm gradually. At −40° C., the reaction mixture was adjusted to pH 3 to 4 by adding 3N hydrochloric acid and then allowed to warm to room temperature. The reaction mixture thus obtained was diluted with ethyl acetate in five-fold volume of the reaction mixture, and the precipitated solid was filtered off. The filtrate was washed with a saturated aqueous solution of sodium bicarbonate and a saturated aqueous solution of sodium chloride; successively, dried over anhydrous magnesium sulfate and concentrated under reduced pressure. A large quantity of solid SBN precipitated in the course of concentration was ground enough with benzene and filtered off, and then the filtrate was again concentrated under reduced pressure. The obtained residue was purified by column chromatography on silica gel (methylene chloride→methylene chloride: ethyl acetate=4:1) to give 868 mg of the title compound having the following physical data and 132 mg of the corresponding 15β-hydroxy compound.

NMR: δ 5.75~5.43 (2H, m), 5.43~5.25 (2H, m), 5.13~5.00 (1H, m), 4.73~4.55 (1H, m), 4.06~3.75 (3H, m), 3.68 (3H, s) 3.53~3.34 (1H, m), 2.05 (3H, s).

IR (chloroform solution): ν 3500, 2900, 2850, 1720 cm⁻¹.

MS: m/e 464, 446.

Reference Example 30

Synthesis of

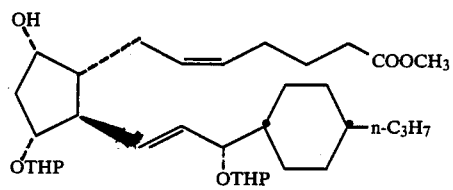

A mixture of 0.868 g of the 15-hydroxy compound (prepared in Reference Example 29), 0.149 ml of 2,3-dihydropyran, 5 ml of methylene chloride and 2 mg of p-toluenesulfonic acid was stirred for 10 minutes at room temperature. After adding several drops of triethylamine, the reaction mixture was concentrated under reduced pressure to give the 15-(tetrahydropyran-2-yloxy) compound. The obtained residue (the 15-(tetrahydropyran-2-yloxy) compound) was dissolved in 5 ml of methanol and thereto was added 0.204 g of potassium carbonate and the mixture was stirred for one hour at 40° C. to 50° C. The reaction mixture was diluted with 50 ml of diethyl ether, washed with water and a saturated aqueous solution of sodium chloride, successively, dried over anhydrous magnesium sulfate and concentrated under reduced pressure. The residue was purified by column chromatography on silica gel (methylene chloride: ethyl acetate=9:1) to give 620 mg of the title compound having the following physical data:

NMR: δ 5.60~5.18 (4H, m), 4.80~4.62 (2H, bτ×2), 4.18~3.71 (5H, m), 3.67 (3H, s), 3.58~3.30 (2H, m), 0.88 (3H, t);

IR: ν 3450, 1710 cm⁻¹.

MS: m/e 488, 404.

Reference Example 31

Synthesis of

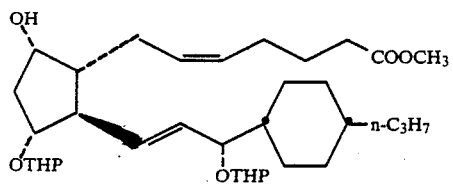

To a mixture of 0.620 g of the 9α-hydroxy compound (prepared in Reference Example 30), 0.550 g of triphenylphosphine, 79 μl of formic acid and 5 ml of dry tetrahydrofuran, was added slowly a solution of 0.330 ml of diethylazodiformate in one ml of dry tetrahydrofuran at a temperature in the vicinity of 5° C., and the mixture was stirred for one hour at the same temperature. The reaction mixture was poured into 50 ml of a saturated aqueous solution of sodium bicarbonate and extracted with ethyl acetate. The extract was washed with water and a satruated aqueous solution of sodium chloride, successively, dried over anhydrous magnesium sulfate and concentrated under reduced pressure. The residue was purified by colum chromatography on silica gel (n-hexane: ethyl acetate=7:1) to give 600 mg of the 11β-formyloxy compound.

To a solution of 600 mg of the obtained formyloxy compound in 4 ml of methanol was added 0.145 g of potassium carbonate and the mixture was stirred for 15 minutes at room temperature. The reaction mixture was diluted with 40 ml of ethyl acetate, washed with water and saturated aqueous solution of sodium chloride, successively, dried over anhydrous magnesium sulfate and concentrated under reduced pressure. The residue was purified by column chromatography on silica gel (n-hexane: ethyl acetate=4:1) to give 441 mg of the title compound having the following physical data:

NMR: δ 5.67~5.19 (4H, m), 4.82~4.59 (2H, bτ×2), 4.19~3.76 (5H, m), 3.68 (3H, s), 3.62~3.38 (2H, m), 0.89 (3H, t).

MS: m/e 488, 457.

Reference Example 32

Synthesis of

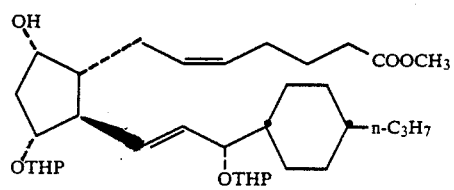

A mixture of 0.44 g of the 9β-hydroxy compound (prepared in Reference Example 31), 427 mg of tosyl chloride and 7 ml of dry pyridine was stirred for 20 hours at room temperature. The reaction mixture was diluted with 100 ml of ethyl acetate, washed with 1N hydrochloric acid, a saturated aqueous solution of sodium bicarbonate and a saturated aqueous solution of sodium bicarbonate and a saturated aqueous solution of sodium chloride, successively, dried over anhydrous magnesium sulfate and concentrated under reduced pressure. The residue was purified by column chromatography on silica gel (n-hexane: ethyl acetate=9:1→4:1) to give 460 mg of the title compound having the following physical data:

NMR: δ 7.78 (2H, d), 7.32 (2H, d), 5.60~5.10 (4H, m), 4.75~4.50 (3H, m), 4.13~3.60 (7H, m+s), 3.55~3.31 (2H, m), 2.44 (3H, s), 1.00-0.80(5H, m+t).

Reference Example 33

Synthesis of

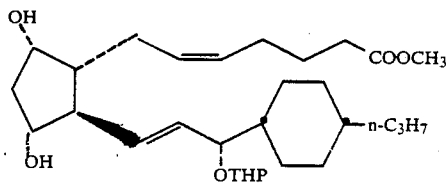

A mixture of 0.460 g of the 11,15-bis(tetrahydropyran-2-yloxy) compound (prepared in Reference Example 32), 10 mg of p-toluenesulfonic acid monohydrate and 5 ml of methanol was stirred for one hour at room temperature. After adding thereto several drops of triethylamine, the reaction mixture was concentrated under reduced pressure. The residue was purified by column chromatography on silica gel (n-hexane: ethyl acetate=1:1→1:2) to give 330 mg of the title compound having the following physical data:

NMR: δ 7.75 (2H, d), 7.32 (2H, d), 5.44 (2H, m), 5.23 (2H, m), 4.05~3.86 (2H, m), 3.66 (3H, s), 2.45 (3H, s), 2.28 (2H, t), 0.88 (3H, t).

IR: ν 3400, 3080, 3060, 3020, 1950, 1850, 1745, 1590, 1480, 1440, 1350, 1230, 1180, 1090, 975 cm$^{-1}$.

MS: m/e 404, 386.

EXAMPLE 7

Synthesis of

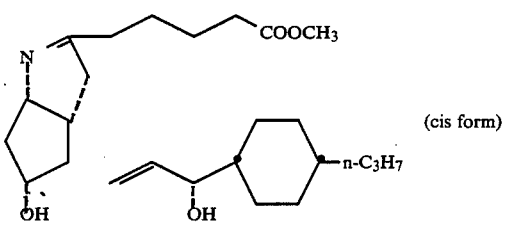

(cis form)

A mixture of 0.165 g of the 9β-tosyloxy compound (prepared in Reference Example 33), 37 mg of sodium azide and 20 ml of dry dimethyl sulfoxide was stirred for 19 hours at a temperature in the vicinity of 40° C. The reaction mixture was poured into 20 ml of ice-water and extracted with a mixture of ethyl acetate and diethyl ether (1:1). The extract was washed with a saturated aqueous solution of sodium chloride, dried over anhydrous magnesium sulfate and concentrated under reduced pressure to give 161 mg of the 9α-azido compound.

A solution of 161 mg of the obtained 9α-azido compound in 3 ml of dry toluene was stirred for 20 hours at a temperature in the vicinity of 70° C. and the reaction mixture was allowed to cool to room temperature. The reaction mixture was concentrated under reduced pressure and the residue was purified by column chromatography on silica gel (ethyl acetate→ethyl acetate: methanol=95:5) to give 87 mg of the title compound having the following physical data:

NMR: δ 5.64~5.42 (2H, m), 4.47~4.32 (1H, m), 4.05~3.77 (2H, m×2), 3.67 (3H, s), 0.90 (3H, t).

IR: ν 3350, 2900, 2850, 1730, 1630, 1430, 1370, 1230, 970 cm$^{-1}$.

MS: m/e 419(M+), 401, 388.

| HPLC: | retention time | 6.09 min; |
|---|---|---|
| | column | TSK-gel (LS-410) ® |
| | | (it is a registered Trade Mark of Toyo Jozo KK); |
| | flow rate | 0.5 ml/min; |
| | temperature | room temperature; |
| | sample size | 10 μg injection (0.5 mg/ml); |
| | mobile phase | 0.02% KH$_2$PO$_4$ in acetonitrile. |

Reference Example 34

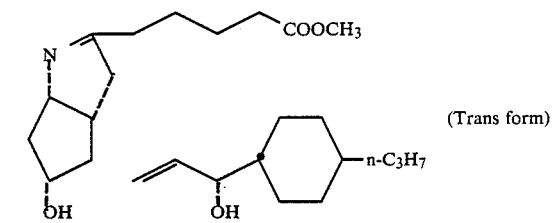

(Trans form)

By the same procedures as described in Reference Example 28 to 33 and Example 7, the title compound having the following physical data was obtained by using the phosphonate prepared in Reference Example 6 and 1α-acetoxy-2α-(6-methoxycarbonylhex-cis-2-enyl)-3β-formyl-4α-(tetrahydropyran-2-yloxy)cyclopentane.

NMR: δ 5.64–5.42(2H, m), 4.47–4.32(1H, m), 3.92–3.75(2H, m), 3.67 (3H, s), 1.05~0.90 (6H, m+t).

IR: ν 3350, 2900, 2850, 1730, 1630, 1430, 1370, 1230, 970 cm$^{-1}$.

MS: m/e 419(M+), 401, 388.

| HPLC: | retention time | 7.39 min; |
|---|---|---|
| | column | TSK-gel (LS-410) ®; |
| | | (it is a registered Trade Mark of Toyo Jozo KK); |
| | flow rate | 0.5 ml/min; |
| | temperature | room temperature; |
| | sample size | 10 μg injection (0.5 mg/ml); |
| | mobile phase | 0.02% KH$_2$PO$_4$ in acetonitrile. |

EXAMPLE 8

Synthesis of

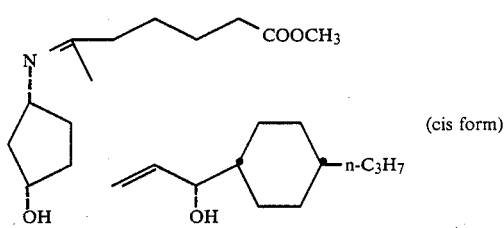

(cis form)

by another process

By the same procedure as described in Reference Example 28 to 30, Reference Example 32 and 33, and Example 7, the title compound having the same physical data as those of the product prepared in Example 7 was obtained by using the phosphonate prepared in Reference Example 7 and 1β-acetoxy-2α-(6-methoxycarbonylhex-cis-2-enyl)-3β-formyl-4α-(tetrahydropyran-2-yloxy)cyclopentane (prepared as described hereafter).

1β-acetoxy-2α-(6-methoxycarbonylhex-cis-2-enyl)-3β-formyl-4α-(tetrahydropyran-2-yloxy)cyclopentane, used as a starting material in the above procedure, was prepared as follows:

(1) Synthesis of

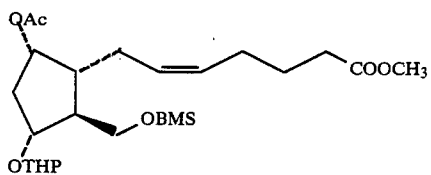

Under an atmosphere of argon, to a mixture of 20 g of 1α-acetoxy-2α-(6-methoxycarbonylhex-cis-2-enyl)-3β-hydroxymethyl-4α-(tetrahydropyran-2-yloxy)cyclopentane (prepared as described in the specification of the British Patent No. 1482928), 7 g of imidazole and 150 ml of dimethylformanide, was added all at once 9.8 g of ter-butyldimethylchlorosilane with stirring at a temperature not more than 5° C. and the mixture was stirred for one hour at room temperature. The reaction mixture was concentrated under reduced pressure and the residue was poured into 200 ml of ice-water and extracted with a mixture of diethyl ether and n-pentane (1:1). The extract was washed with a saturated aqueous solution of sodium chloride, dried over anhydrous magnesium sulfate and concentrated under reduced pressure to give 28 g of the crude title compound having the following physical data:

NMR: δ 5.45~5.30 (2H, m), 5.10~5.00 (1H, m), 4.66~4.50 (1H, m), 4.20~3.40 (8H, m), 2.05 (3H, s), 0.90 (9H, s), 0.05 (6H, s).

IR: ν 2930, 2850, 1730, 1460, 1450, 1360, 1240, 1100, 1010, 830 cm$^{-1}$.

(2) Synthesis of

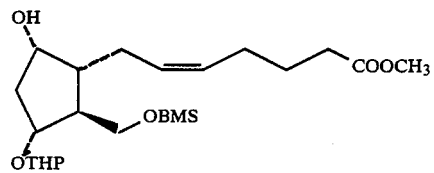

A mixture of 28 g of the 9-acetoxy compound (prepared in the above (1)), 7.17 g of potassium carbonate and 150 ml of methanol was stirred for 1.5 hours at 40° C. and the reaction mixture was diluted with diethyl ether. The ethereal solution was washed with water and a saturated aqueous solution of sodium chloride, successively, over anhydrous magnesium sulfate and concentrated under reduced pressure to give 25 g of the crude title compound having the following physical data:

TLC (n-hexane: ethyl acetate=1:1): Rf=0.65.

(3) Synthesis of

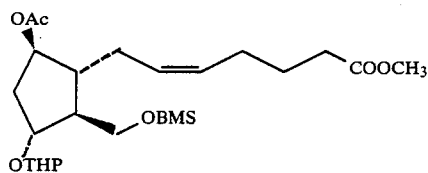

To a mixture of 25 g of the 9α-hydroxy compound (prepared in the above (2)), 27.2 g of triphenylphosphine, 5.94 ml of acetic acid and 250 ml of tetrahydrofuran, was added dropwise a solution of 16.4 ml of diethylazodiformate in 50 ml of tetrahydrofuran at 5° C. to 6° C., and the mixture was stirred for one hour at the same temperature. The reaction mixture was poured into a saturated aqueous solution of sodium bicarbonate and extracted with ethyl acetate. The extract was washed with water and a saturated aqueous solution of sodium chloride, successively, dried over anhydrous magnesium sulfate and concentrated under reduced pressure. The residue was purified by column chromatography on silica gel (n-hexane: ethyl acetate=10:1→4:1) to give 11.4 g of the title compound having the following physical data:

NMR: δ 5.45~5.30 (2H, m), 4.99~4.80 (1H, m), 4.66~4.50 (1H, m) 4.20~3.40 (8H, m), 2.05 (3H, s), 0.90 (9H, s), 0.05 (6H, s).

(4) Synthesis of

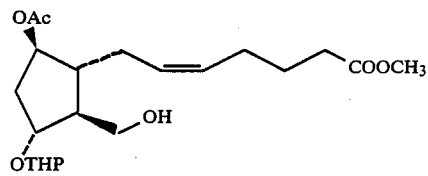

To a solution of 11.4 g of the 3-(tert-butyldimethyl-silyloxymethyl) compound (prepared in the above (3)) in 100 ml of dry tetrahydrofuran, was added 100 ml of a 1M solution of tetrabutylammonium fluoride in tetrahydrofuran and the mixture was stirred for 30 minutes at room temperature. The reaction mixture was diluted with 500 ml of ethyl acetate, washed with water and a saturated aqueous solution of sodium chloride, successively, dried over anhydrous magnesium sulfate and concentrated under reduced pressure to give 8.8 g of the crude title compound having the following physical data:

TLC (n-hexane: ethyl acetate=1:1): Rf=0.37.

(5) Synthesis of

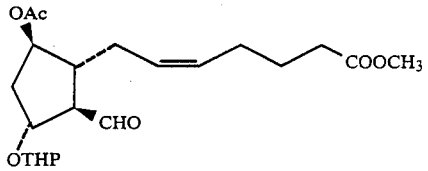

Under an atmosphere of argon, a solution of 2.67 ml of dry dimethyl sulfoxide in 5 ml of dry methylene chloride was added dropwise to a solution of 1.63 ml of oxalyl chloride in 35 ml of dry methylene chloride at −78° C., and the mixture was stirred for 30 minutes at the same temperature. To the obtained solution was added dropwise a solution of 5.0 g of the 3-hydroxymethyl compound (prepared in the above (4)) in 15 ml of methylene chloride at −78° C., and the mixture was stirred for one hour at the same temperature. After adding 10.48 ml of triethylamine thereto, the reaction mixture was stirred for one hour at −78° C., and then for 30 minutes at 0° C. The reaction mixture was poured into a mixture of 100 ml of ice-water and 50 ml of a saturated aqueous solution of sodium bicarbonate, and then extracted with diethyl ether. The extract was washed with water and a saturated aqueous solution of sodium chloride, successively, dried over anhydrous magnesium sulfate and concentrated under reduced pressure. The residue was purified by column chromatography on silica gel (n-hexane: ethyl acetate=3:1→2:1) to give 4.44 g of the title compound having the following physical data:

NMR: δ 9.72 (1H, d d), 5.55~5.30 (2H, m), 5.04~4.89 (1H, m), 4.68~4.55 (1H, m), 3.65 (3H, s), 2.03 (3H, s).

MS: m/e 365, 312, 295, 252.

Reference Example 35

Synthesis of

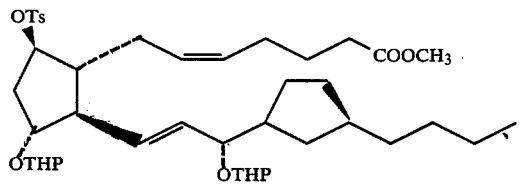

By the same procedures as described in Reference Examples 28 to 30 and 32, the title compound having the following physical data was obtained by using the phosphonate prepared in Reference Example 3 and 1β-acetoxy-2α-(6-methoxycarbonylhex-cis-2-enyl)-3β-formyl-4α-(tetrahydropyran-2-yloxy)cyclopentane prepared in Example 8.

NMR: δ 7.8 (2H, d), 7.35 (2H, d), 5.7~5.1 (4H, m), 4.70 (1H, m), 4.60 (1H, m), 3.67 (3H, s), 2.46 (3H, s), 0.90 (3H, t).

IR: ν 2950, 2860, 1740, 1600, 1440, 1370, 1020, 980 cm$^{-1}$.

MS: m/e 386, 368, 355, 342, 337, 311.

Reference Example 36

Synthesis of

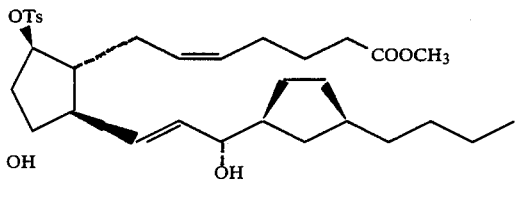

and

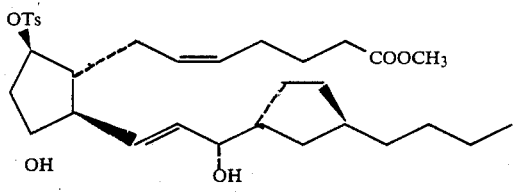

By the same procedure as described in Reference Example 33, the title compound (mixture of (16S, 18R) isomer and (16R, 18R) isomer) was obtained by using the 11,15-bis(tetrahydropyran-2-yloxy) compound prepared in Reference Example 35.

The obtained mixture was purified by chromatography on a Lobar® column (cyclohexane: ethyl acetate=1:1) to give (16S, 18R) isomer (less polar) and (16R, 18R) isomer (more polar), having the following physical data:

(a) (16S, 18R) isomer

Optical rotation: $[\alpha]_D^{20}$ +3.77° (c=0.53, chloroform).

NMR: δ 7.76 (2H, d), 7.32 (2H, d), 5.50 (2H, m), 5.25 (2H, m), 4.60 (1H, m), 3.66 (3H, s), 2.46 (3H, s), 0.86 (3H, t);

IR: ν 3400, 2960, 2940, 2870, 1740, 1605, 1440, 1360, 1180, 1100, 975 cm$^{-1}$;

MS: m/e 386, 368, 355, 342, 337.

(b) (16R, 18R) isomer

Optical rotation: $[\alpha]_D^{20}$ -1.69° (c=0.65, chloroform).

NMR: δ 7.76 (2H, d), 7.33 (2H, d), 5.6~5.0 (4H, m), 4.60 (1H, m), 3.66 (3H, s), 2.43 (3H, s). 0.86 (3H, t).

IR: ν 3400, 2960, 2930, 2860, 1740, 1605, 1440, 1360, 1180, 1100, 970 cm$^{-1}$.

MS: m/e 386, 368, 355, 342, 337.

EXAMPLE 9

Synthesis of

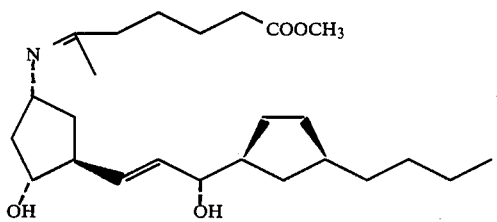

By the same procedure as described in Example 7, the title compound having the following physical data was obtained by using the 9β-tosyloxy compound ((16S, 18R) isomer) prepared in Reference Example 36.

Optical rotation: $[\alpha]_D^{20}$ +1.33° (c=0.60, chloroform).

NMR: δ 5.54 (2H, m), 4.35 (1H, m), 3.9~3.7 (2H, m), 3.76 (3H, s), 2.74~2.52 (2H, m), 0.88 (3H, t).

IR (KBr method): ν 3420, 2960, 2940, 2870, 1740, 1640, 1460, 1430, 1260, 980 cm$^{-1}$.

MS: m/e 419(M+), 401, 388, 372, 357, 346, 332, 319, 294.

EXAMPLE 10

Synthesis of

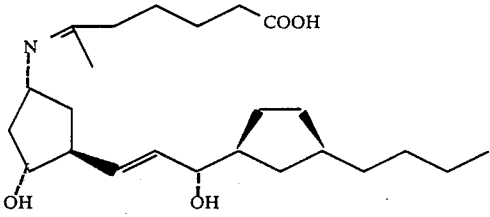

To a solution of 60 mg of the ester (prepared in Example 9) in one ml of methanol were added 0.186 ml of 1N aqueous solution of sodium hydroxide and 0.186 ml of water, and the mixture was stirred for 2.5 hours at 45° C. The reaction mixture was concentrated under reduced pressure and to the residue was added 5 ml of water and the obtained solution was washed with chloroform. To the solution was added 0.186 ml of 1N hydrochloric acid under cooling with ice and the obtained solution was concentrated under reduced pressure. The residual solid thus obtained was recrystallized from isopropanol to give 58 mg of the title compound as foamy solid having the following physical data:

Optical rotation: $[\alpha]_D^{20}$ +10.60° (c=2.65, chloroform).

NMR: δ 5.50 (2H, m), 4.44 (1H, m), 3.94~3.74 (2H, m), 0.88 (3H, t).

IR (KBr method): ν 3430, 2950, 2870, 1710, 1650, 1570, 1420, 1100, 970 cm$^{-1}$.

MS: m/e 405(M+), 387, 376, 369, 362, 344, 332, 319, 280.

Reference Example 37

Synthesis of

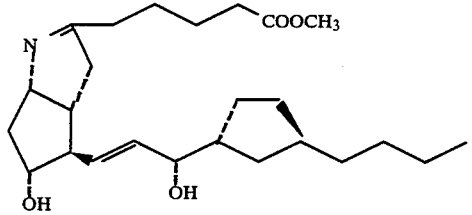

By the same procedure as described in Example 7, the title compound having the following physical data was obtained by using the 9β-tosyloxy compound ((16R, 18R) isomer) prepared in Reference Example 36.

mp: 87° C.-90° C.

Optical rotation: [α]$_D^{20}$ −2.50° (c=0.60, chloroform).

NMR: δ 5.34 (2H, m), 4.35 (1H, m), 3.92~3.72 (2H, m), 3.66 (3H, s), 2.76~2.50 (2H, m), 0.88 (3H, t).

Reference Example 38

Synthesis of

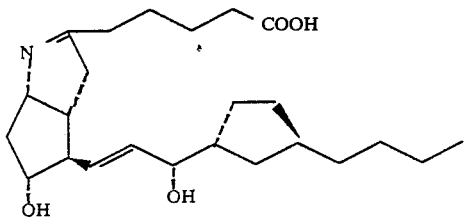

By the same procedure as described in Example 10, the title compound having the following physical data was obtained by using the ester prepared in Reference Example 37.

Optical rotation: [α]$_D^{20}$ +6.296° (c=2.70, chloroform).

NMR: δ 5.50 (2H, m), 4.43 (1H, m), 3.90~3.70 (2H, m), 0.88 (3H, t).

Reference Example 39

Synthesis of

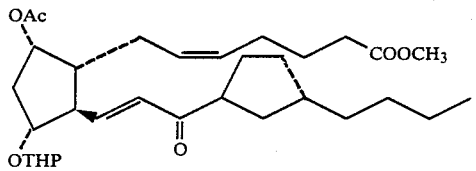

By the same procedure as described in Reference Example 28, the title compound having the following physical data was obtained by using the phosphonate prepared in Reference Example 4 and 1α-acetoxy-2α-(6-methoxycarbonylhex-cis-2-enyl)-3β-formyl-4α-(tetrahydropyran-2-yloxy)cyclopentane.

IR: ν 1730, 1690, 1660, 1620 cm$^{-1}$.

MS: m/e 546(M+), 515, 462.

Reference Example 40

Synthesis of

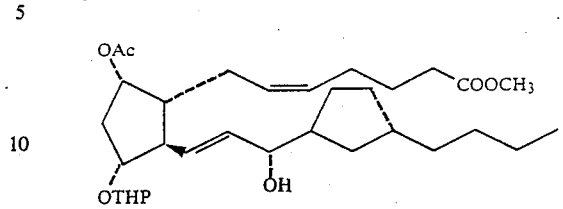

Under an atmosphere of argon, to a solution of 6.796 g of 2,6-di-tert-butyl-4-methylphenol in 30 ml of toluene was added dropwise 9.1 ml of a 1.7M solution of diisobutylaluminium hydride in toluene at −30° C. to −20° C. with stirring and the mixture was stirred for one hour at 0° C. to −10° C. After cooling the reaction mixture to −78° C., thereto was added dropwise a solution of 842 mg of the 15-oxo compound (prepared in Reference Example 39) in 20 ml of toluene and the mixture was allowed to warm gradually to 5° C. with stirring. To the reaction mixture was added 5.5 ml of water and the mixture was stirred overnight at room temperature. After adding 100 ml of ethyl acetate thereto, the mixture was filtered through a layer of celite. The filtrate was concentrated under reduced pressure and the residue was purified by column chromatography on silica gel (methylene chloride: ethyl acetate=10:1→5:1→ ethyl acetate) to give 950 mg of the title compound having the following physical data:

IR: ν 3480, 2925, 2850, 1730, 1430, 970 cm$^{-1}$.

MS: m/e 530, 517, 470, 464, 446.

Reference Example 41

Synthesis of

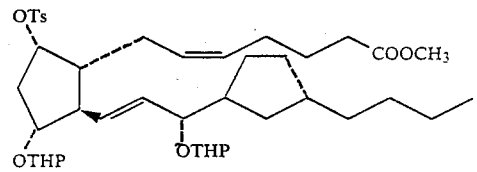

By the same procedures as described in Reference Example 30 to 32, the title compound having the following physical data was obtained by using the 15-hydroxy compound prepared in Reference Example 40.

NMR: δ 7.75 (2H, d), 7.33 (2H, d), 5.7~5.0 (4H, m), 4.8~4.3 (3H, m), 4.3~3.2 (6H, m), 3.67 (3H, s), 2.44 (3H, s).

IR: ν 1735, 1600, 1440, 1360, 1170, 980 cm$^{-1}$.

Reference Example 42

Synthesis of

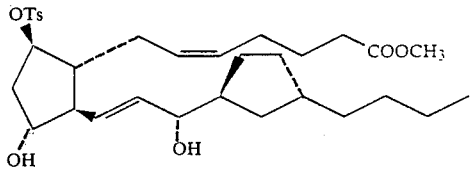

and

-continued

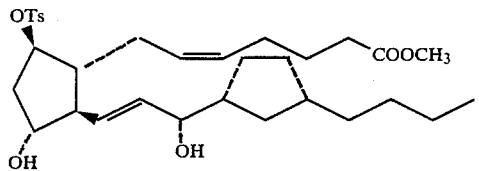

By the same procedure as described in Reference Example 33, the title compound (mixture of (16S, 18S) isomer and (16R, 18S) isomer) was obtained by using the 11,15-bis(tetrahydropyran-2-yloxy) compound prepared in Reference Example 41.

The obtained mixture was purified by chromatography on a Lobar® column (ethyl acetate: cyclohexane=2:1) to give (16S, 18S) isomer (less polar) and (16R, 18S) isomer (more polar), having the following physical data:

(a) (16S, 18S) isomer

Optical rotation: $[\alpha]_D^{20}$ −2.08° (c=1.007, chloroform).

NMR: δ 7.75 (2H, d), 7.33 (2H, d), 5.6∼5.0 (4H, m), 4.8∼4.4 (1H, m), 4.2∼3.4 (2H, m), 3.67 (3H, s), 2.45 (3H, s).

IR: ν 3400, 1740, 1600, 1440, 1360, 1180, 980 cm$^{-1}$.

MS: m/e 386, 368.

(b) (16R, 18S) isomer

Optical rotation: $[\alpha]_D^{20}$ −1.41° (c=1.061, chloroform).

NMR: δ 7.75 (2H, d), 7.33 (2H, d), 5.6∼5.0 (4H, m), 4.7∼4.4 (1H, m), 4.3∼3.3 (2H, m), 3.67 (3H, s), 2.45 (3H, s).

IR: ν 3400, 1740, 1600, 1440, 1360, 1180 cm$^{-1}$.

MS: m/e 386, 368.

EXAMPLE 11

Synthesis of

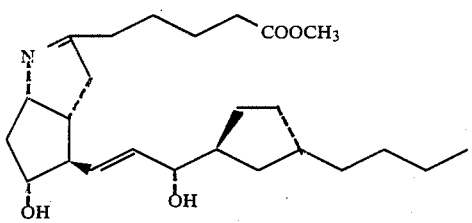

By the same procedure as described in Example 7, the title compound having the following physical data was obtained by using the 9β-tosyloxy compound ((16S, 18S) isomer) prepared in Reference Example 42.

mp: 60° C.-61° C.

Optical rotation: $[\alpha]_D^{20}$ −6.04° (c=0.513, chloroform).

NMR: δ 5.7-5.4 (2H, m), 4.5-4.28 (1H, m), 3.9-3.7 (2H, m), 3.68 (3H, s).

IR (KBr method): ν 3350, 1735, 1640, 1460, 1430, 1290 cm$^{-1}$.

MS: m/e 419(M+), 401, 388, 319.

EXAMPLE 12

Synthesis of

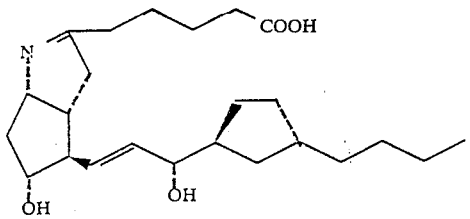

By the same procedure as described in Example 10, the title compound having the following physical data was obtained by using the ester prepared in Example 11.

Optical rotation: $[\alpha]_D^{20}$ +6.6° (c=0.559, chloroform).

NMR: δ 3.6-3.3 (2H, m), 4.6-4.3 (1H, m), 3.95-3.6 (2H, m).

IR (KBr method): ν 3450, 1700, 1640, 1090 cm$^{-1}$.

MS: m/e 405(M+), 387, 319, 280.

Reference Example 43

Synthesis of

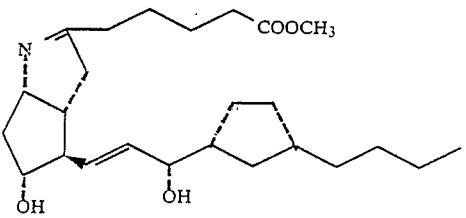

By the same procedure as described in Example 7, the title compound having the following physical data was obtained by using the 9β-tosyloxy compound ((16R, 18S) isomer) prepared in Reference Example 42.

Optical rotation: $[\alpha]_D^{20}$ −1.29° (c=0.543, chloroform).

NMR: δ 5.7∼5.4 (2H, m), 4.5∼4.2 (1H, m), 3.95∼3.7 (2H, m), 3.68 (3H, s), 1.0∼0.7 (4H, m).

Reference Example 44

Synthesis of

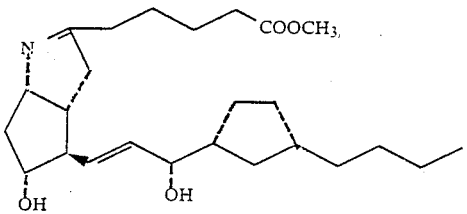

By the same procedure as described in Example 10, the title compound having the following physical data was obtained by using the ester prepared in Reference Example 43.

Optical rotation: $[\alpha]_D^{20}$ +5.6° (c=0.619, chloroform).

NMR: δ 5.7∼5.3 (2H, m), 4.5∼4.2 (1H, m), 4.0∼3.8 (2H, m), 1.0∼0.6 (4H, m).

Reference Example 45

Synthesis of

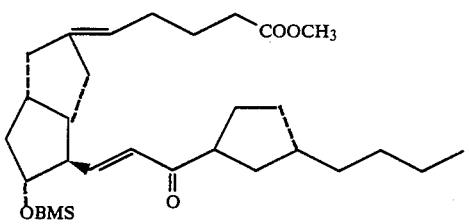

Under an atmosphere of argon, to a suspension of 0.113 g of sodium hydride (content: 64%) in 10 ml of dry tetrahydrofuran was added dropwise a solution of 0.979 g of the phosphonate (prepared in Reference Example 4) in 3 ml of dry tetrahydrofuran at room temperature, and the mixture was stirred at the same temperature till the evolution of hydrogen gas ceased. Thereto was added dropwise a solution of 1.04 g of 3-(4-methoxycarbonyl-E-butylidene)-6-syn-formyl-7-anti-(tert-butyldimethylsilyloxy)-cis-bicyclo[3.3.0]-octane (prepared as described hereafter) in 4 ml of dry tetrahydrofuran at room temperature and the mixture was stirred for one hour at the same temperature. The reaction mixture was adjusted to pH 3 to 4 by adding acetic acid and diluted with ethyl acetate. The solution was washed with water, a saturated aqueous solution of sodium bicarbonate and a saturated aqueous solution of sodium chloride, successively, dried over anhydrous magnesium sulfate and concentrated under reduced pressure. The residue was purified by column chromatography on silica gel (n-hexane: ethyl acetate=95:5) to give 1.12 g of the title compound having the following physical data:

NMR: δ 6.71 (1H, d d), 6.16 (1H, d), 5.21 (1H, m), 3.91 (1H, m), 3.66 (3H, s), 3.09 (1H, m), 0.88 (3H, m), 0.84 (9H, s), −0.02 (6H, d).

IR: ν 1738, 1694, 1668, 1627, 1250, 835, 778 cm$^{-1}$.

MS: m/e 530(M+), 515, 499, 473, 441, 398.

3-(4-methoxycarbonyl-E-butylidene)-6-syn-formyl-7-anti-(tert-butyldimethylsilyloxy)-cis-bicyclo[3.3.0]octane, used as a starting material in the above procedure, was prepared as follows:

(1) Synthesis of

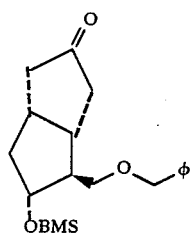

A mixture of 27 g of 6-syn-benzyloxymethyl-7-antihydroxy-cis-bicyclo[3.3.0]octan-3-one (prepared as described in the specification of the British Patent No. 2017699B and of the U.S. Pat. No. 4,479,966), 19.6 g of tert-butyldimethylchlorosilane, 13.6 g of imidazole and 150 ml of dimethylformamide, was stirred for one hour under cooling with water and then dimethylformamide was removed therefrom under reduced pressure. The residue was poured into ice-water and extracted with a mixture of n-hexane and diethyl ether (1:1). The extract was washed with water, a saturated aqueous solution of sodium bicarbonate and a saturated aqueous solution of sodium chloride, successively, dried over anhydrous magnesium sulfate and concentrated under reduced pressure. The residue was purified by column chromatography on silica gel (methylene chloride: ethyl acetate=15:1) to give 39.36 g of the title compound having the following physical data:

IR: ν 2960, 2940, 2870, 1740, 1260, 1110 cm$^{-1}$.
MS: m/e 374(M+), 359, 313.

(2) Synthesis of

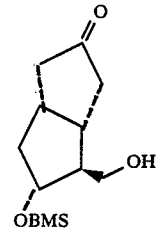

Under an atmosphere of hydrogen, a mixture of 10.17 g of the benzyloxymethyl compound (prepared in the above (1)) and 3.0 g of palladium on carbon (content: 10%) in 50 ml of a mixture of ethyl acetate and acetic acid (2:1) was stirred vigorously overnight at room temperature. The reaction mixture was filtered and the filtrate was concentrated under reduced pressure. The residue was purified by column chromatography on silica gel (n-hexane: ethyl acetate=7:1→1:1) to give 6.44 g of the title compound having the following physical data:

NMR: δ 4.07 (1H, q), 3.67 (2H, d), 1.84 (1H, m), 1.28 (1H, m), 0.88 (9H, s), 0.06 (6H, d).

IR: ν 3480, 1732, 1260, 835, 777 cm$^{-1}$.

MS: m/e 285, 269, 227, 209.

(3) Synthesis of

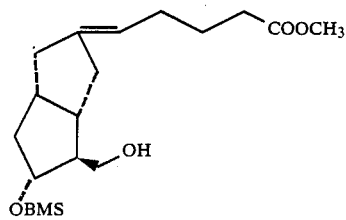

To a mixture of 5.87 g of the alcohol (prepared in the above (2)), 1.9 ml of isopropenyl methyl ether and 100 ml of methylene chloride, was added 0.20 g of camphorsulfonic acid under cooling with ice, with stirring and then the mixture was allowed to warm to room temperature. The reaction mixture was quenched by triethylamine and then diluted with diethyl ether. The ethereal layer was washed with water and a saturated aqueous solution of sodium chloride, successively, dried over anhydrous magnesium sulfate and concentrated under reduced pressure to give 6-syn-(2,4-dioxa-3,3-dimethylpentyl)-7-anti-(tert-butyldimethylsilyloxy)-cis-bicyclo[3.3.0]octan-3-one as crude product.

A mixture of 18.6 g of (4-carboxybutyl)triphenylphosphonium bromide, 210 ml of toluene and 9.4 g of potassium tert-butoxide was stirred for one hour at 80° C. and then allowed to cool to room temperature. To the obtained solution was added all at once a solution of the 3-ketone compound (prepared above) in toluene and the mixture was stirred overnight at room temperature. The reaction mixture was diluted with 300 ml of water, adjusted to pH 3 by adding oxalic acid and then extracted with diethyl ether. The extract was washed with water and a saturated aqueous solution of sodium chloride, successively, dried over anhydrous magnesium sulfate and concentrated under reduced pressure to give 3-(4-carboxy-EZ-butylidene)-6-syn-(2,4-dioxa-3,3-dimethylpentyl)-7-anti-(tert-butyldimethylsilyloxy)-cis-bicyclo[3.3.0]octane as crude product.

The mixture of the (2,4-dioxa-3,3-dimethylpentyl) compound (prepared above), 20 ml of 0.5N hydrochloric acid and 45 ml of tetrahydrofuran was stirred for 30 minutes at 0° C. and then diluted with 300 ml of diethyl ether. The ethereal layer was washed with water and a saturated aqueous solution of sodium chloride, successively, dried over anhydrous magnesium sulfate and concentrated under reduced pressure. The residue was purified by column chromatography on silica gel (n-hexane: ethyl acetate=3:1→2:3) to give 3-(4-carboxy-EZ-butylidene)-6-syn-hydroxymethyl-7-anti-(tert-butyldimethylsilyloxy)-cis-bicyclo[3.3.0]octane.

To a solution of the carboxylic acid (prepared above) in diethyl ether was added dropwise an ethereal solution of diazomethane at 0° C. till the reaction solution turned to pale yellow, and then the reaction mixture was concentrated under reduced pressure. The residue was purified by column chromatography on a Kiesel ® gel 60 ("Kiesel" is a registered Trade Mark of Merck & Co.) (n-hexane: ethyl acetate=3:1) to give 2.68 g of the title compound having the following physical data and 2.14 g of the corresponding Z-butylidene isomer.

NMR: δ 5.21 (1H, m), 3,84 (1H, m), 3.68 (2H, m), 3.66 (3H, s), 1.07 (1H, m), 0.88 (9H, s), 0.07 (6H, d).

IR: 3470, 1740, 1722 (shoulder), 1253, 837, 778 cm$^{-1}$.

MS: m/e 382(M+), 351, 325, 293, 269, 233, 201.

(4) Synthesis of

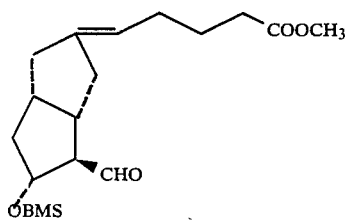

A mixture of 0.76 g of the hydroxymethyl compound (prepared in the above (3)), 1.5 g of sulfur trioxide-pyridine complex, 2.55 ml of triethylamine and 12 ml of dimethyl sulfoxide was stirred for 20 minutes at room temperature. To the reaction mixture was added a mixture of ice and a saturated aqueous solution of ammonium chloride and the mixture was extracted with diethyl ether. The extract was washed with water and a saturated aqueous solution of sodium chloride, successively, dried over anhydrous magnesium sulfate and concentrated under reduced pressure. The residue was purified by column chromatography on silica gel (n-hexane: ethyl acetate=20:1) to give 0.677 g of the title compound having the following physical data:

NMR: δ 9.70 (1H, d), 5.24 (1H, m), 4.26 (1H, m), 3.65 (3H, s), 1.34 (1H, m), 0.85 (9H, s), 0.23 (3H, d).

IR: ν 2715, 1738, 1727, 1255, 836, 777 cm$^{-1}$.

MS: m/e 380(M+), 365, 349, 323, 291, 199.

Reference Example 46

Synthesis of

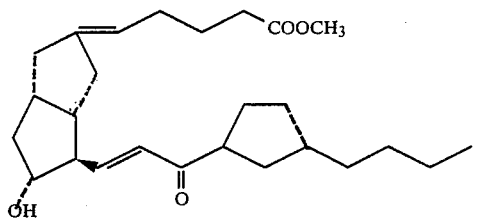

To a solution of 0.27 g of the 11-(tert-butyldimethylsilyloxy) compound (prepared in Reference Example 45) in 3 ml of acetonitrile was added two drops of 46% hydrogen fluoride per 10 minutes at room temperature with stirring and the reaction mixture was diluted with diethyl ether. The ethereal layer was washed with a saturated aqueous solution of sodium bicarbonate and a saturated aqueous solution of sodium chloride, successively, dried over anhydrous magnesium sulfate and concentrated under reduced pressure. The residue was purified by column chromatography on silica gel (n-hexane: ethyl acetate=3:1) to give 0.18 g of the title compound having the following physical data:

NMR: δ 6.76 (1H, d d), 6.21 (1H, d), 5.26 (1H, m), 3.90 (1H, m), 3.67 (3H, s), 3.12 (1H, m), 0.88 (3H, m).

IR: ν 3460, 1738, 1724 (shoulder), 1692, 1667, 1625 cm$^{-1}$.

MS: m/e 416(M+), 398, 372, 367, 245, 218.

EXAMPLE 13

Synthesis of

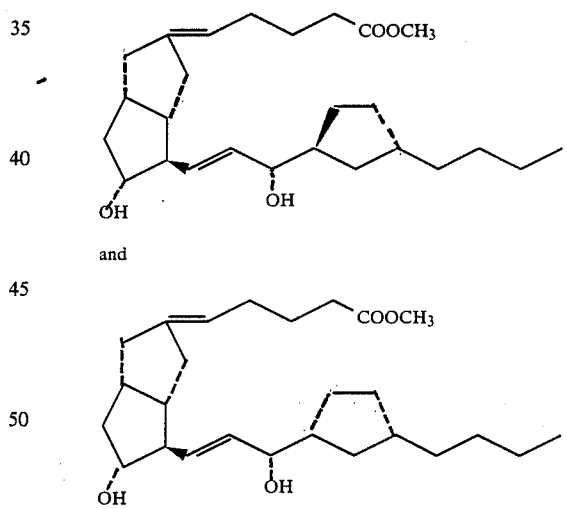

and

To a solution of 1.97 g of 2,6-di-tert-butyl-4-methylphenol in 18.5 ml of toluene was added dropwise 3.8 ml of a 1.75M solution of diisolbutylaluminium hydride in toluene under cooling with ice and the mixture was stirred for 30 minutes at the same temperature. After cooling the reaction solution to −78° C., thereto was added a solution of 0.25 g of the 15-oxo compound (prepared in Reference Example 46) in 3 ml of toluene and the reaction mixture was allowed to warm gradually to room temperature. To the reaction mixture was added 2.3 ml of water, and the mixture was stirred vigorously for 30 minutes and then filtered after adding anhydrous magnesium sulfate. The filtrate was concentrated under reduced pressure and the residue thus obtained was purified by column chromatography on silica gel (n-hexane: ethyl acetate=3:1→2:1→1:3) to give the title compound (mixture of (16S, 18S) isomer and (16R, 18S) isomer).

The mixture was purified by chromatography on a Lobar ® column (n-hexane: ethyl acetate=1:1) to give 78 mg of (16S, 18S) isomer (less polar) and 64 mg of (16R, 18S) isomer (more polar), having the following physical data:

(a) (16S, 18S) isomer
NMR: δ 5.52 (2H, m), 5.24 (1H, m), 3.82 (1H, m), 3.7 (1H, m), 3.67 (3H, s), 0.88 (3H, m).
IR (KBr method): ν 3480, 1732, 1708, 975 cm⁻¹.
MS: m/e 400, 382, 356, 232.

(b) (16R, 18S) isomer
NMR: δ 5.52 (2H, m), 5.24 (1H, m), 3.85 (1H, m), 3.73 (1H, m), 3.67 (3H, s), 0.88 (3H, m).
IR: ν 3400, 1740, 1725 (shoulder), 972 cm⁻¹.
MS: m/e 400, 382, 356, 275, 232.

EXAMPLE 14

Synthesis of

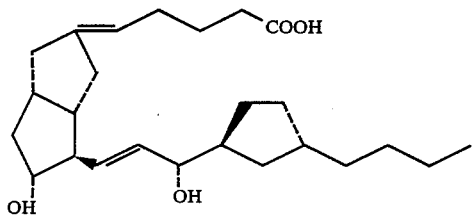

To a solution of 73 mg of the ester ((16S, 18S) isomer, prepared in Example 13) in 1.7 ml of methanol, was added 0.35 ml of 1N aqueous solution of sodium hydroxide, and the mixture was stirred overnight at room temperature. After adding 2 ml of water thereto, methanol was removed under reduced pressure. The residual solution was adjusted to pH 3 by adding 1N hydrochloric acid and then extracted with diethyl ether. The extract was washed with water and a saturated aqueous solution of sodium chloride, successively, dried over anhydrous magnesium sulfate and concentrated under reduced pressure. The residue was purified by column chromatography on silica gel (n-hexane: ethyl acetate=2:1→ethyl acetate) to give 67 mg of the title compound having the following physical data:

NMR: δ 5.48 (2H, m), 5.22 (1H, m), 3.80 (1H, m), 3.69 (1H, m), 0.88 (3H, m).
IR: ν 3500~2400, 1708, 970 cm⁻¹.
MS: m/e 386, 368, 342, 218.

Reference Example 47

Synthesis of

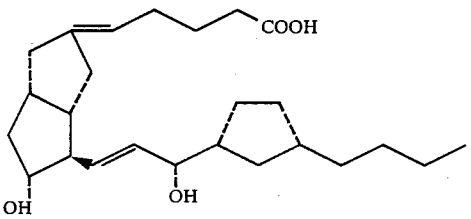

By the same procedure as described in Example 14, the title compound having the following physical data was obtained by using the ester ((16R, 18S) isomer) prepared in Example 13.

NMR: δ 5.50 (2H, m), 5.22 (1H, m), 3.83 (1H, m), 370 (1H, m), 0.88 (3H, m).
IR: ν 3600-2400, 1708, 970 cm⁻¹.
MS: m/e 386, 368, 342, 218.

Reference Example 48

Synthesis of

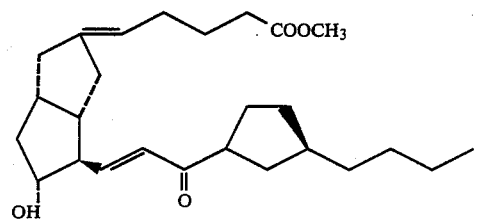

By the same procedures as described in Reference Example 45 and 46, the title compound having the following physical data was obtained by using the phosphonate prepared in Reference Example 3 and 3-(4-methoxycarbonyl-E-butylidene)-6-syn-formyl-7-anti-(tert-butyldimethylsilyloxy)-cis-bicyclo[3.3.0]octane prepared in Reference Example 45.

NMR: δ 6.76 (1H, d d), 6.21 (1H, d), 5.25 (1H, m), 3.90 (1H, m), 3.67 (3H, s), 3.12 (1H, m), 0.88 (3H, t).
IR: ν 3460, 1738, 1720 (shoulder), 1690, 1667, 1625 cm⁻¹.

EXAMPLE 15

Synthesis of

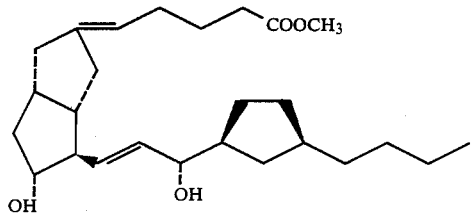

and

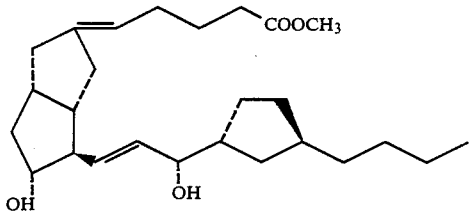

By the same procedure as described in Example 13, the title compounds, i.e. (16S, 18R) isomer (less polar) and (16R, 18R) isomer (more polar), having the following physical data, were obtained by using the 15-oxo compound prepared in Reference Example 48.

(a) (16S, 18R) isomer
NMR: δ 5.55(2H, m), 5.22(1H, m), 3.83 (1H, m), 3.70 (1H, m), 3.66 (3H, s), 0.88 (3H, t).
MS: m/e 400, 372, 369.

(b) (16R, 18R) isomer
NMR: δ 5.55 (2H, m), 5.22 (1H, m), 3.83 (1H, m), 3.70 (1H, m), 3.66 (32H, s), 0.88 (3H, t).

MS: m/e 400, 372, 369.

EXAMPLE 16

Synthesis of

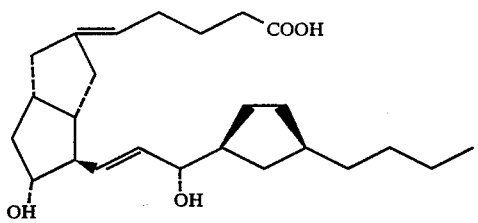

By the same procedure as described in Example 14, the title compound having the following physical data was obtained by using the ester ((16S, 18R) isomer) prepared in Example 15.

Optical rotation: $[\alpha]_D^{25}$ +82.6° (c=1.48, methanol).
NMR: δ 5.47 (2H, m), 5.20 (1H, m), 3.80 (1H, m), 3.68 (1H, m), 0.88 (3H, t).
IR: ν 3450, 2950, 2850, ~2600, 1700, 1450, 1240, 1070, 975 cm$^{-1}$.
MS: m/e 386, 368.

Reference Example 49

Synthesis of

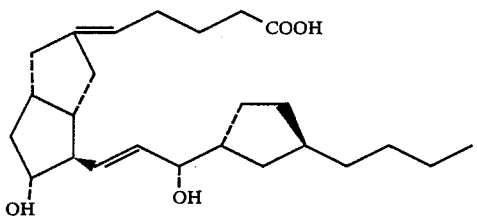

By the same procedure as described in Example 14, the title compound having the following physical data was obtained by using the ester ((16R, 18R) isomer) prepared in Example 15.

Optical rotation: $[\alpha]_D^{25}$ +71.1° (c=1.42, methanol).
NMR: δ 5.47(2H, m), 5.20(1H, m), 3.80(1H, m), 3.68(1H, m), 0.88 (3H, t).
IR: ν 3450, 2950, 2850, ~2600, 1700, 1450, 1240, 1070, 975 cm$^{-1}$.
MS: m/e 386, 368.

EXAMPLE 17

Synthesis of D-glucuronic acid salt of

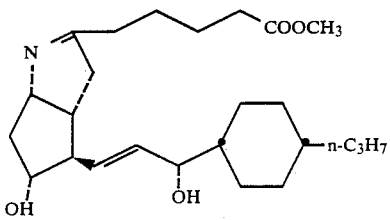

To a solution of 50 mg of 15-(cis-4-propylcyclohexyl)-16,17,18,19,20-pentanor-6,9α-nitrilo-PGI$_1$ methyl ester (prepared in Example 7 or 8) in 5 ml of ethanol, was added a solution of 25.5 mg of D-glucuronic acid in 5 ml of water at room temperature and the mixture was stirred. The reaction mixture was concentrated under reduced pressure and dried in vacuo to give 72 mg of the title compound as white powder, having the following physical data:

NMR (methanol-d$_4$ solution): δ 5.65–5.4, (2H, m), 5.18 (1H, d), 4.52 (1H, d), 4.25 (1H, d), 3.96~3.8 (1H, m), 3.72 (1H, d t), 3.68 (3H, s), 3.6~3.4 (2H, m), 2.78~2.30 (3H, m), 2.10~2.0 (1H, m), 1.75~1.10 (18H, m), 0.90 (3H, t).

IR (KBr method): ν 3350, 2900, 1725, 1670, 1590, 1420, 1400, 1080, 1040 cm$^{-1}$.

The present invention includes within its scope pharmaceutical compositions which comprise at least one PG analogue of the general formula (I), non-toxic salt thereof, non-toxic acid-addition salt thereof or cyclodextrin clathrate thereof, together with a pharmaceutical carrier or coating.

In clinical practice, the compounds of the present invention will normally be administered systemically or partially; usually by oral or parenteral (e.g. intravenous, subcutaneous, intramuscular or intradermal) administration.

Solid compositions for oral administration include compressed tablets, pills, dispersible powders and granules. In such solid compositions, one or more of the active compound(s) is, or are, admixed with at least one inert diluent such as lactose, mannitol, glucose, hydroxypropyl cellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, disintegrating agents such as cellulose calcium gluconate, stabilizing agents such as lactose, and solubilizers such as glutamic acid and asparaginic acid. The tablets or pills may, if desired, be made into enteric film-coated or gastric film-coated tablets or pills, such as sugar-coated, gelatin-coated, hydroxypropylcellulose-coated or hydroxypropylmethylcellulose phthalate-coated tablets or pills; two or more layers may be used.

The compositions for oral administration also include capsules of absorbable material such as gelatin, containing one or more of the active substances with or without the addition of diluents or excipients.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise at least one compound of the present invention.

Preparations according to the invention for parenteral administration include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, and Polysorbate 80 (registered Trade Mark). Those compositions may also include adjuvants such as preserving agents, wetting agents, emulsifying agents, dispersing agents, stabilizing agents (e.g. lactose) and solubilizers (e.g. glutamic acid and asparaginic acid). They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions include, for parenteral administration, liquids for external use, and endermic liniments such as ointments; suppositories for rectal administration; and pessaries for vaginal administration. Such compositions are prepared by known methods.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance.

The dose to be administered is determined depending upon, for example, age, body weight, symptoms, the desired therapeutic effects, the route of administration, and the duration of the treatment.

In the human adult, the doses per person are generally between 0.1 µg and 10 mg by oral administration, and between 0.01 µg and 10 mg by parenteral (preferably, intravenous or intradermal) administration for the prevention or the therapy of hypertension, disorders of the peripheral circulation, thrombosis, cardiostenosis, myocardial infarction or arteriosclerosis, and can be administered up to several times per day.

As mentioned above, the doses to be used depend on various conditions. Therefore, there may be cases in which doses greater than the ranges specified above, or lower than the ranges specified above, may be used.

The following Examples illustrate pharmaceutical compositions according to the invention.

Preparative Example 1

To a mixture of 3 mg of 15-[(1S,3R)-3-propylcyclopentyl]-16,17,18,19,20-pentanor-6-keto-$PGE_1$ methyl ester, 100 mg of magnesium stearate, 20 mg of silicon dioxide, 10 mg of talc and 200 mg of cellulose calcium gluconate (CCG), was added microcrystalline cellulose to make the total weight 10 g. The resulting mixture was mixed sufficiently to make it homogeneous, and then tabletted in conventional manner to give 100 tablets each containing 30 µg of the active ingredient.

Preparative Example 2

To a solution of 100 mg of 15-[(1S,3R)-3-propylcyclopentyl]-16,17,18,19,20-pentanor-6-keto-$PGE_1$ methyl ester in one ml of ethanol was added gradually 19.9 g of vaselium album, and then the mixture was triturated sufficiently to give 20 g of ointment containing 5 mg of the active ingredient per one g of ointment.

Preparative Example 3

One hundred mg of 15-(cis-4-propylcyclohexyl)-16,17,18,19,20-pentanor-6,9α-nitrilo-$PGI_1$ methyl ester, 70 mg of L-glutamic acid and 5 g of lactose were dissolved in 100 ml of distilled water. Thereafter, sterile filtration was performed in a conventional manner and the solution was placed, in 100 µl portions, in ampoules.

After freeze drying, the ampoules were sealed to obtain 1000 freeze dried preparations suitable for injection each containing 100 µg of the active ingredient per ampoule.

We claim:

1. A prostaglandin analogue of the general formula:

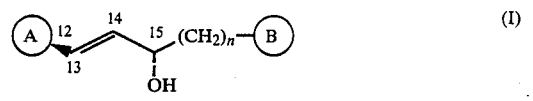

(wherein Ⓐ represents a group of the general formula

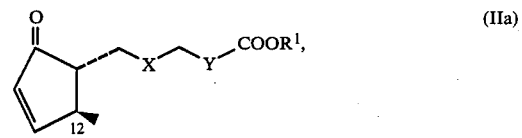

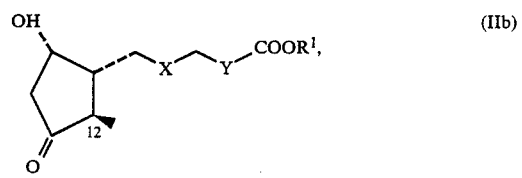

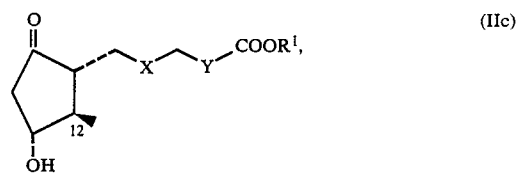

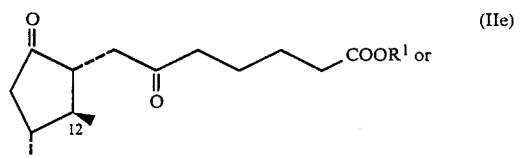

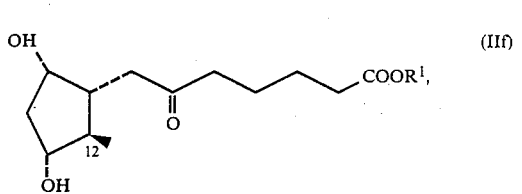

(wherein X represents a cis-vinylene group or an ethylene group, Y represents an ethylene group or a trans-vinylene group, $R^1$ represents a hydrogen atom or a straight- or branched-chain alkyl group of 1 to 4 carbon atoms, Ⓑ represents a group of the general formula:

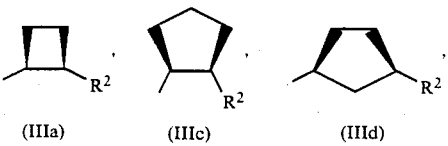

-continued

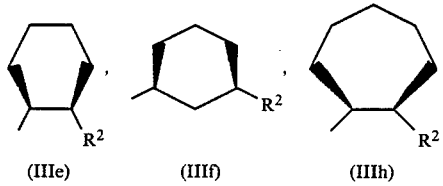

(IIIe)   (IIIf)   (IIIh)

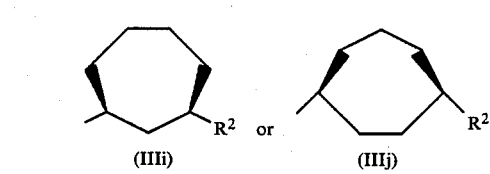

(IIIi) or (IIIj)

(wherein $R^2$ represents a straight- or branched-chain alkyl group of 1 to 8 carbon atoms), n represents zero, or an integer of 1 or 2 and the double bond between $C_{13}$ and $C_{14}$ in formula (I) is E, or a non-toxic salt thereof when $R^1$ represents a hydrogen atom, or a cyclodextrin clathrate thereof.

2. A prostaglandin analogue according to claim 1, wherein Ⓐ represents a group of the formula (IIc), (IIe) or (IIf).

3. A prostaglandin analogue according to claim 2, wherein Ⓐ represents a group of the formula (IIe).

4. A prostaglandin analogue according to claim 1, wherein $R^1$ represents a hydrogen atom or a methyl group.

5. A prostaglandin analogue according to claim 1, wherein Ⓑ represents a group of the formula (IIIc), (IIId), (IIIe) or (IIIf).

6. A prostaglandin analogue according to claim 5, wherein Ⓑ represents a group of the formula (IIId) or (IIIf).

7. A prostaglandin analogue according to claim 1, wherein the alkyl group represented by $R^2$, in the group of the formula Ⓑ, represents a straight- or branched-chain alkyl group of 1 to 4 carbon atoms.

8. A prostaglandin analogue according to claim 1, wherein n represents zero.

9. A prostaglandin analogue according to claim 1, which is one of the general formula:

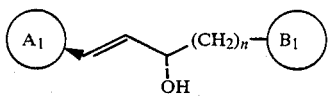 (Ia)

(wherein Ⓐ₁ represents a group of the general formula:

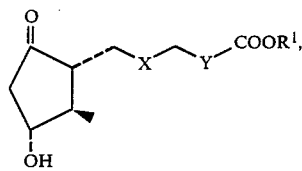

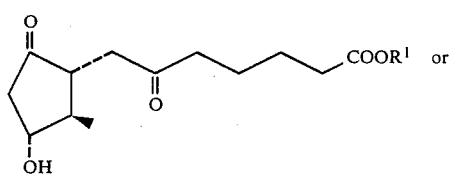 or

-continued

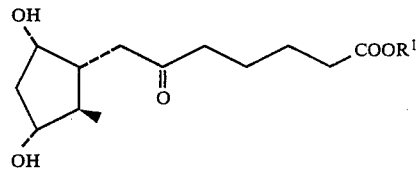 (IIf)

(wherein X represents a cis-vinylene group or an ethylene group, Y represents an ethylene group or a trans-vinylene group and $R^1$ represents a hydrogen atom or a straight- or branched-chain alkyl group of 1 to 4 carbon atoms), Ⓑ₁ represents a group of the general formula:

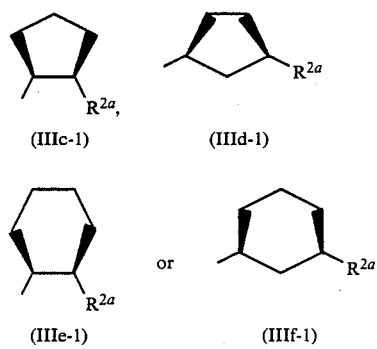

(IIIc-1)   (IIId-1)

or (IIIe-1)   (IIIf-1)

(wherein $R^{2a}$ represents a straight- or branched-chain alkyl group of 1 to 4 carbon atoms and n represents zero, 1 or 2), or non-toxic salt thereof, or cyclodextrin clathrate thereof.

10. A prostaglandin analogue which is 15-[(1S,3R)-3-propylcyclopentyl]-16,17,18,19,20-pentanor-PGF$_{2\alpha}$ or methyl ester thereof.

11. A prostaglandin analogue according to claim 1, which is one of the general formula:

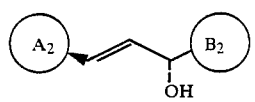 (Ib)

wherein Ⓐ₂ represents a group of the general formula:

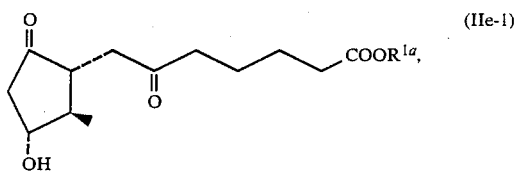 (IIe-1), (wherein X and Y are as hereinbefore defined, and $R^{1a}$ represents a hydrogen atom or a methyl group), and Ⓑ₂ represents a group of the general formula:

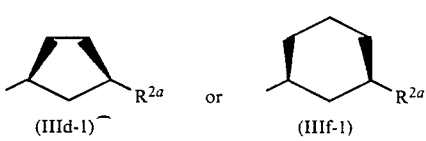

(IIId-1)   (IIIf-1)

(wherein $R^{2a}$ represents a straight- or branched-chain alkyl group of 1 to 4 carbon atoms), or non-toxic salt thereof, or cyclodextrin clathrate thereof.

12. A prostaglandin analogue according to claim 11, which is 15-[(1S,3R)-3-propylcyclopentyl]-16,17,18,19,20-pentanor-6-keto-$PGE_1$ or methyl ester thereof.

13. A prostaglandin analogue according to claim 11, which is 15-[(1S,3R)-3-butylcyclopentyl]-16,17,18,19,20-pentanor-6-keto-$PGE_1$ or methyl ester thereof.

14. A pharmaceutical composition useful in combating hypertension or inhibiting blood platelet aggregation in a patient which composition comprises as active ingredient an effective amount of at least one prostaglandin analogue of the general formula (I) depicted in claim 1, wherein the various symbols are as defined in claim 1, or a non-toxic salt thereof, or a cyclodextrin clathrate thereof, in association with a pharmaceutical carrier or coating.

15. A method of combating hypertension or of inhibiting blood platelet aggregation in a patient which comprises administering to the patient an effective amount of a prostaglandin analogue of the general formula (I) depicted in claim 1, wherein the various symbols are as defined in claim 1, or a non-toxic salt thereof, or a cyclodextrin clathrate thereof.

* * * * *